United States Patent

Kimura et al.

[11] Patent Number: 5,942,688
[45] Date of Patent: Aug. 24, 1999

[54] APPARATUS AND METHOD FOR DETECTING A MEASURABLE QUANTITY OF AN OBJECT

[75] Inventors: Tomonori Kimura; Shusou Wadaka; Koichiro Misu; Tsutomu Nagatsuka; Mitsuhiro Koike, all of Kanagawa, Japan

[73] Assignee: Mitsubishi Denki Kabushiki Kaisha, Tokyo, Japan

[21] Appl. No.: 08/937,244

[22] Filed: Sep. 8, 1997

Related U.S. Application Data

[63] Continuation of application No. 08/465,789, Jun. 6, 1995, abandoned.

[30] Foreign Application Priority Data

Nov. 18, 1994 [JP] Japan ..................................... 6-284983
Feb. 27, 1995 [JP] Japan ..................................... 7-038392

[51] Int. Cl.$^6$ .................................................. G01N 29/00
[52] U.S. Cl. ................................ 73/598; 73/600; 73/602; 73/627
[58] Field of Search ............................. 73/597, 598, 599, 73/600, 602, 628

[56] References Cited

U.S. PATENT DOCUMENTS

| | | | |
|---|---|---|---|
| 3,779,070 | 12/1973 | Cushman et al. | 73/865.5 |
| 3,852,709 | 12/1974 | Mueller | 73/603 |
| 4,141,347 | 2/1979 | Green et al. | 73/627 |
| 4,862,384 | 8/1989 | Bujard | 73/599 |
| 4,905,207 | 2/1990 | Fellinger et al. | 367/99 |
| 5,070,734 | 12/1991 | Kawabuchi et al. | 73/628 |
| 5,351,543 | 10/1994 | Migliori et al. . | |
| 5,452,611 | 9/1995 | Jones et al. . | |

FOREIGN PATENT DOCUMENTS

| | | |
|---|---|---|
| 0042288 | 12/1981 | European Pat. Off. . |
| 0 667 526 A1 | 8/1995 | European Pat. Off. . |
| 8305611 | 11/1983 | France . |
| 2-136135 | 5/1990 | Japan . |
| 4-24580 | 1/1992 | Japan . |
| 4024580 | 1/1992 | Japan . |
| 4-286952 | 10/1992 | Japan . |
| 5-123320 | 5/1993 | Japan . |
| 5-200024 | 8/1993 | Japan . |
| 0 622 999 1 | 8/1994 | Japan . |
| 6-229991 | 8/1994 | Japan . |

OTHER PUBLICATIONS

"New Nondestructive Inspection Handbook," edited by Nihon Nondestructive Inspection Association Corporation, Oct. 15, 1992, pp. 256–278, issued by Nikkan Kogyo Shinbun Company Ltd.

"Ultrasonic Defect Probing Method (revised version)," edited by the 19$^{th}$ Committee of Steel Making in Nihon Academy Promotion, Jul. 30, 1974, pp. 114–149, issued by Nikkan Kogyo Shinbun Company Ltd.

*Primary Examiner*—Hezron Williams
*Assistant Examiner*—Helen C. Kwok
*Attorney, Agent, or Firm*—Burns, Doane, Swecker & Mathis, LLP

[57] ABSTRACT

A detecting device for detecting a physical quantity of an object, which includes a transmission signals generating device for generating first and second transmission signals of different frequencies, an ultrasonic wave transmission device that is excited by the first and the second transmission signal, for transmitting ultrasonic pulses corresponding to the first and the second transmission signal to an object, and a signal processing device for carrying out a signal processing process on the first and the second echo. The signal processing process is such that it detects phases of the first and second echo corresponding to the first and second transmission signal, which are received by the ultrasonic wave receiving device. An indeterminacy integer times as large as $2\pi$ of the phase of each of the first and second echo is determined on the basis of the information of the amplitudes of the first or the second echo, and a distance from the ultrasonic wave transmission device through an object to the ultrasonic wave receiving device along an ultrasonic wave propagating path is detected on the basis of the determined phase of the first or second echo.

22 Claims, 56 Drawing Sheets

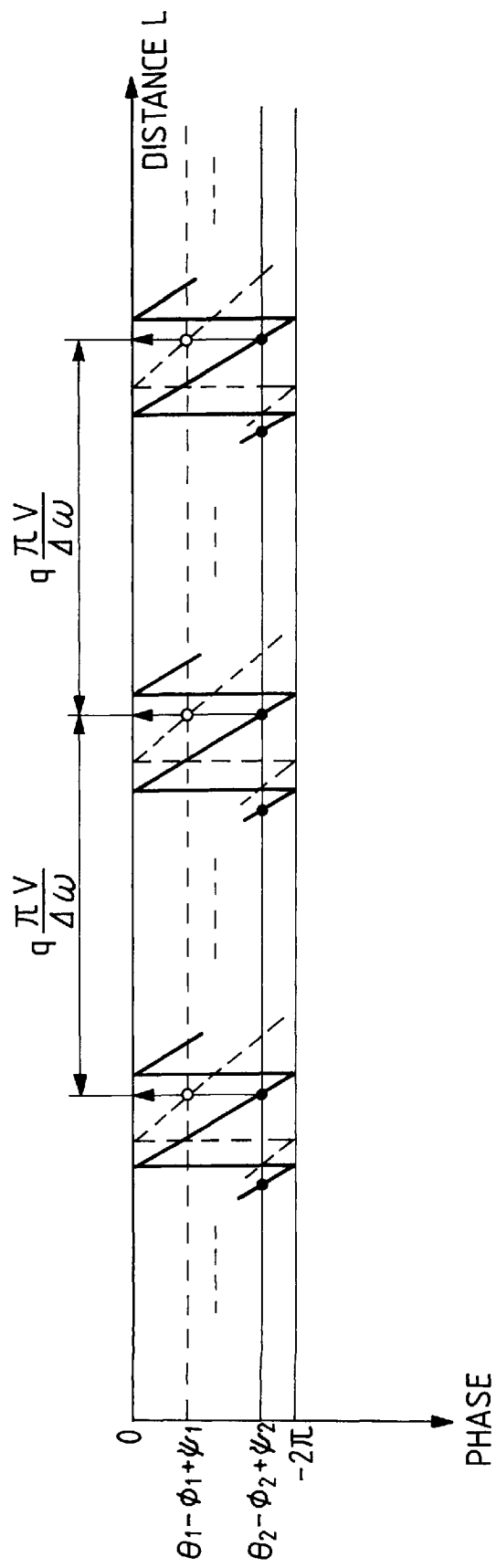

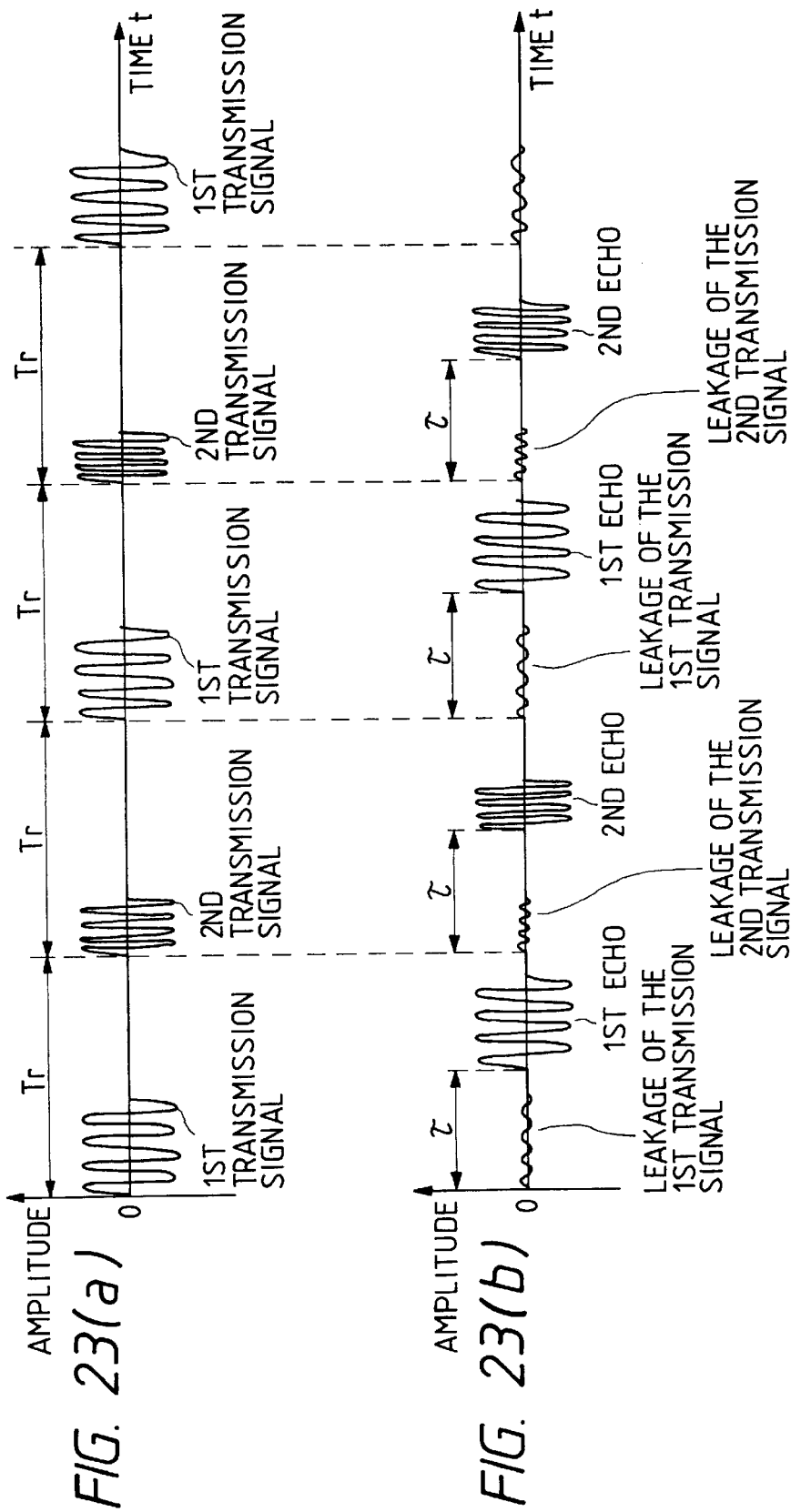

k-th 1ST ECHO (k+2)th 1ST ECHO (k+4)th 1ST ECHO

RESULT OF ADDING THE 1ST ECHOES (k+1)th 2ND ECHO
(k+3)th 2ND ECHO
(k+5)th 2ND ECHO

RESULT OF ADDING THE 2ND ECHOES

TRANSMISSION SIGNAL $S_1$

TRANSMISSION SIGNAL $S_2$

RECEIVING ECHO SIGNAL $r_1$

RECEIVING ECHO SIGNAL $r_2$

ENVELOPE OF A RECEIVING ECHO SIGNAL $r_1$

ENVELOPE OF A RECEIVING ECHO SIGNAL $r_2$

PHASE OF THE FIRST ECHO $r_1$

PHASE OF THE RECEIVING ECHO $r_2$

RELATIONSHIP BETWEEN THE ENVELOPE
AND THE PORTION IN THE RECEIVING
ECHO SIGNAL $r_1$

RELATIONSHIP BETWEEN THE
ENVELOPE AND THE PORTION IN
THE RECEIVING ECHO SIGNAL $r_2$

TRANSMISSION SIGNAL s1

TRANSMISSION SIGNAL s2

RECEIVING ECHO SIGNAL $r_1$

RECEIVING ECHO SIGNAL $r_2$

ENVELOPE OF A RECEIVING ECHO SIGNAL $r_1$

ENVELOPE OF A RECEIVING ECHO SIGNAL $r_2$

PHASE OF THE FIRST ECHO $r_1$

PHASE OF THE RECEIVING ECHO $r_2$

APPARATUS AND METHOD FOR DETECTING A MEASURABLE QUANTITY OF AN OBJECT

This application is a continuation, of application Ser. No. 08/465,789, filed Jun. 6, 1995 now abandoned.

BACKGROUND OF THE INVENTION

The present invention relates to a detecting method for detecting a physical quantity of an object under detecting on the basis of the nature of waves in a broad sense, which includes acoustic waves, ultrasonic waves and light, such as electromagnetic waves, elastic waves or the like. What are to be detected are physical quantities in a broad sense, which include physical characteristics of an object to be detected, such as a material to be detected. Specific examples of what are to be detected are:

A. Distance from a detecting device to an object to be detected, presence or absence of the detected object;
B. Shape and position of the detected object;
C. Various characteristics and a propagating speed of a medium when a wave propagates thereon or therethrough, the medium being located between a detecting device and an object to be detected:

An ultrasonic detecting method and an ultrasonic detecting device will be described by way of examples, for ease of explanation.

In the specification, a word "measurement" will frequently be used in addition to a word "detection", but the former is involved in the latter.

Of the ultrasonic detecting method and device, an ultrasonic measuring method and an ultrasonic measuring device, which use an ultrasonic wave, will first be described.

Generally, the ultrasonic detecting device means a device which projects a beam of an ultrasonic wave to an object, and receives and processes a reflected, scattered or refracted ultrasonic wave from the object, whereby detecting the object, measuring a distance from the detecting device to the object and the shape of the object, visualizing the object, or recognizes the object. The ultrasonic detecting device also means a device for measuring a sonic speed of an acoustic wave traveling in an object or an ultrasonic wave propagating medium. The object involves any object located in any medium which allows an ultrasonic wave to propagate, such as gas including air, liquid including water, sea water, or solid.

This type of a conventional ultrasonic measuring device will be described using an example in the field of ultrasonic nondestructive inspection. An ultrasonic measuring device functionally illustrated in FIG. 42 is described in "New Nondestructive Inspection Handbook" (referred to as an article A), edited by Nihon Nondestructive Inspection Association Corporation, Oct. 15, 1992, pp. 256 to 278, issued by Nikkan Kogyo Shinbun Company Ltd.

In FIG. 42 reference numeral 1 designates a pulser; 2, a receiver, 24, a timing signal generator portion; 4, a horizontal sweeper portion; 5, a display unit; 6, a probe; 7, a test piece; and 8, a defect. In the figure, the test piece 7 corresponds to an ultrasonic wave propagating medium, and the defect 8 corresponds to an object.

The operation of the ultrasonic measuring device thus constructed will be described. An impulse method is employed in the ultrasonic measuring device as shown in FIG. 42, which is used in the field of the ultrasonic nondestructive inspection. For the impulse method, reference is made to "Ultrasonic Defect Probing Method (revised edition)" (referred to as an article B), edited by the 19th Committee of Steel Making in Nihon Academy Promotion, Jul. 30, 1974, pp. 114 to 140, issued by Nikkan Kogyo Shinbun Company Ltd. The pulser 1 generates an electric pulse at the timing defined by a transmission repetitive frequency. The pulse width of the electric pulse is narrow to such an extent that it could be considered as an impulse, as shown in FIG. 43($a$). The electric pulse is applied to the probe 6 where it is converted into an ultrasonic pulse as shown in FIG. 43($b$). The ultrasonic pulse is projected to the test piece 7.

The ultrasonic pulse propagates through the test piece 7, and is reflected by the defect 8 in the test piece 7 and the bottom of the test piece 7, to thereby return to the probe 6. The probe 6 receives the returned ultrasonic pulse in the form of a reflection echo electric signal. The echo signal is amplified and rectified by the receiver 2. The output signal of the receiver 2 is transmitted to the display unit 5.

The timing signal generator portion 24 generates sync signals for controlling the operation timings of the respective circuits in the device. The horizontal sweeper portion 4 generates a time-axis (abscissa) sweep signal by using the sync signal for transmission to the display unit 5. Then, the display unit 5 displays a transmission pulse T, a reflection or defect echo F from the defect 8, and another reflection echo B from the bottom of the test piece 7, which are arrayed on the time axis, as shown in FIG. 42.

On the screen of the display unit 5, a position of the defect 8 in the test piece 7 is known by measuring a time position where the defect echo F appears. The size of the defect 8 is defined by the height of the defect echo F.

To improve the resolution in the measurement of distance to the defect 8 in the ultrasonic measuring device of this type, it is necessary to accurately measure the time position where the defect echo F appears. An extremely narrow time width of the defect echo F provides an accurate measurement of the time position. However, the actual ultrasonic pulse transmitted to the test piece 7 is such that even in the ultrasonic pulse of which the oscillation continuation time is short, the number of oscillation waves is approximately 1.5 to 3 as shown in FIG. 43($b$).

Accordingly, the time width of the defect echo F is also such a length. An oscillating waveform of the ultrasonic pulse depends largely on the characteristic of the probe 6. In the probe 6 having a narrow frequency response characteristic, the number of the oscillation waves is large, while in the probe having a broad frequency response characteristic, it is small. In other words, the oscillation continuation time is inversely proportional to the bandwidth. Even in the probe 6, currently used as a broad band-width probe, the number of oscillation waves is 1.45 to 3 waves at most, as described on page 263 in the article A. Therefore, the resolution in the distance measurement is the half of the number of oscillation waves, i.e., 0.7 to 1.5 waves, even if the fact that the ultrasonic pulse travels to and from the defect 8 is taken into consideration.

The amplitude of an envelope of the defect echo gradually increases with time, and decreases after it reaches its peak. By making use of this amplitude variation, the resolution can be improved over the above-mentioned one when the lapse of time from an instant that the envelope rises till it reaches the peak is measured or a time point where the envelope rises from zero is measured. Actually, it is difficult to exactly measure these time points, however. The reason for this is that a variation of the amplitude is gentle in the vicinity of the time point where the amplitude is peaked and the time point where it rises.

To cope with this, a possible measure is present. In this measure, a threshold value is set at a position on the amplitude envelope, where is a preset value lower than the peak value. A time point where the amplitude varying along the envelope reaches the threshold value is measured. This measure also suffers from problems in that the accuracy and stability of the measurement are not satisfactory. The reason for this is that the echo waveform varies depending on the probe used and the shape of the object 8.

In some of the ultrasonic measuring devices and the ultrasonic microscopes in the field of the ultrasonic nondestructive inspection, the probe 6 is excited by using a burst signal as shown in FIG. 44, not the impulse as shown in FIG. 43(*a*). Where the burst signal is used, the oscillation continuation time of the reflection echo signal is longer than that in the case of FIG. 43(*b*). The result is an inaccurate measurement of the time positions where the reflection echoes appear.

In this type of the ultrasonic detecting device and method, for example, the ultrasonic measuring device, the measuring accuracy is unsatisfactory in measuring a time point where a reflection echo signal is received from an object. And the resolution in the distance measurement up to the object 8 is poor. The same thing is true for a case where a refractive echo rather than a scattering echo is received from an object 8, to thereby gain information of the object. This problem arises also in the measurement for the purpose of gaining information on an object 8 by receiving and processing an echo signal as well as the measurement for the purpose of measuring a distance to an object 8. The former measurement includes the measurements for grasping a shape of an object 8, visualizing the object, and discriminating the object. This leads to poor measuring accuracy in a case where an object 8, which allows an ultrasonic wave to propagate therein, is measured in its thickness and a sonic speed of the ultrasonic wave when it propagates therein.

For the above-mentioned background reasons, the present invention is to provide a detecting method which improves the resolution, or the detection accuracy, by using a signal of a multiple of frequencies, and a detecting device for executing the detecting method. For conventional detecting devices using an ultrasonic wave signal of a multiple of frequencies, reference is made to Published Unexamined Japanese Patent Application Nos. Hei. 4-24580, 4-286952, 2-136135, 5-123320, 5-200024, and 6-229991, for example.

The ultrasonic detecting device disclosed in the publication of Hei. 4-24580 is constructed on the basis of the fact that when an ultrasonic wave propagates in an ultrasonic wave propagating medium, the frequency characteristic on its attenuation depends on the propagating path of the ultrasonic wave. Two ultrasonic wave signals of high and low frequencies are used. To detect an object, one of the ultrasonic wave signals is selected which is suitable for the detection of the object. The ultrasonic detecting device disclosed in the publication of Hei. 4-286952 is constructed so as to detect a defect 8 on the basis of the fact that when an ultrasonic wave propagating medium (insulator) suffers from a defect located near to the end face thereof, an intensity of the end face echo of the ultrasonic wave varies depending on the frequency of the ultrasonic wave. The ultrasonic detecting devices disclosed in the publication of Hei. 2-136135, 5-123320, and 5-200024 are constructed on the basis of the fact that when an ultrasonic wave propagates in an ultrasonic wave propagating medium, its attenuation depends on the frequency thereof.

The detecting device disclosed in the publication of Hei. 6-229991 uses two burst signals (transmission signals) of different frequencies. In the detecting device, the phases of two detecting signals (echo signals) of those burst signals are detected, a difference between the two phases is obtained, a frequency is produced which is defined by the difference between the two phases and the difference between the two frequencies. The resultant frequency is used for measuring a distance from the detecting device to an object. The detecting method of the publication is equivalent to the detecting method using a single burst signal of a specific frequency, which is defined by the difference between the two frequencies. In this respect, this conventional art is different from the present invention in which two signals of different frequencies are provided, a candidate is selected from the two signals, and a distance to an object to be detected is determined using the candidate.

While those conventional art disclosed in the publications of Hei. 4-24580, 4-286952, 2-136135, 5-123320, 5-200024, and 6-229991 each use two signals of different frequencies, those are different from the present invention in the objects and the constructions as will be described hereinafter.

SUMMARY OF THE INVENTION

According to the invention as set forth in claim 1 in the present patent application, there is provided a detecting method comprising:

a first transmission step for transmitting a first burst signal of a first frequency to an object to be detected;

a second transmission step for transmitting a second burst signal for transmitting a second burst signal of a second frequency, which is different from the first frequency, to the object;

a first receiving step for receiving a first reflection signal, which corresponds to the first burst signal, from the object;

a second receiving step for receiving a second reflection signal, which corresponds to the second burst signal, from the object;

a first candidate deriving step for deriving a first candidate of a physical quantity of the object by the first frequency, on the basis of the first reflection signal;

a second candidate deriving step for deriving a second candidate of a physical quantity of the object by the second frequency, on the basis of the second reflection signal; and a third candidate deriving step for deriving a third candidate of a physical quantity of the object by the first and the second frequency, on the basis of the first and the second candidate.

According to the invention as set forth in claim 13 in the present patent application, there is provided a detecting device comprising:

a first transmission means for transmitting a first burst signal of a first frequency to an object to be detected;

a second transmission means for transmitting a second burst signal for transmitting a second burst signal of a second frequency, which is different from the first frequency, to the object;

a first receiving means for receiving a first reflection signal, which corresponds to the first burst signal, from the object;

a second receiving means for receiving a second reflection signal, which corresponds to the second burst signal, from the object;

a first candidate deriving means for deriving a first candidate of a physical quantity of the object by the first frequency, on the basis of the first reflection signal;

a second candidate deriving means for deriving a second candidate of a physical quantity of the object by the second frequency, on the basis of the second reflection signal; and a third candidate deriving means for deriving a third candidate of a physical quantity of the object by the first and the second frequency, on the basis of the first and the second candidate.

In operation, each of the inventions of claims 1 and 13 transmits a first burst signal of a first frequency to an object to be detected, transmits a second burst signal for transmitting a second burst signal of a second frequency, which is different from the first frequency, to the object, receives a first reflection signal, which corresponds to the first burst signal, from the object, receives a second reflection signal, which corresponds to the second burst signal, from the object, produces a first candidate of a physical quantity of the object by the first frequency, on the basis of the first reflection signal, produces a second candidate of a physical quantity of the object by the second frequency, on the basis of the second reflection signal, and produces a third candidate of physical quantity of the object by the first and the second frequency, on the basis of the first and the second candidate.

BRIEF DESCRIPTION OF THE DRAWINGS

FIG. 4 shows an another characteristic diagram useful in explaining the signal processing procedure in the first embodiment.

FIGS. 23(a) and 23(b) show waveform diagrams for explaining the operation of the twelfth embodiment.

DETAILED DESCRIPTION OF THE PREFERRED EMBODIMENTS

First Embodiment

An ultrasonic distance measuring device incorporating the present invention, which is the first embodiment of the present invention, will be described with reference to FIGS. 1 to 5.

Figure 1:
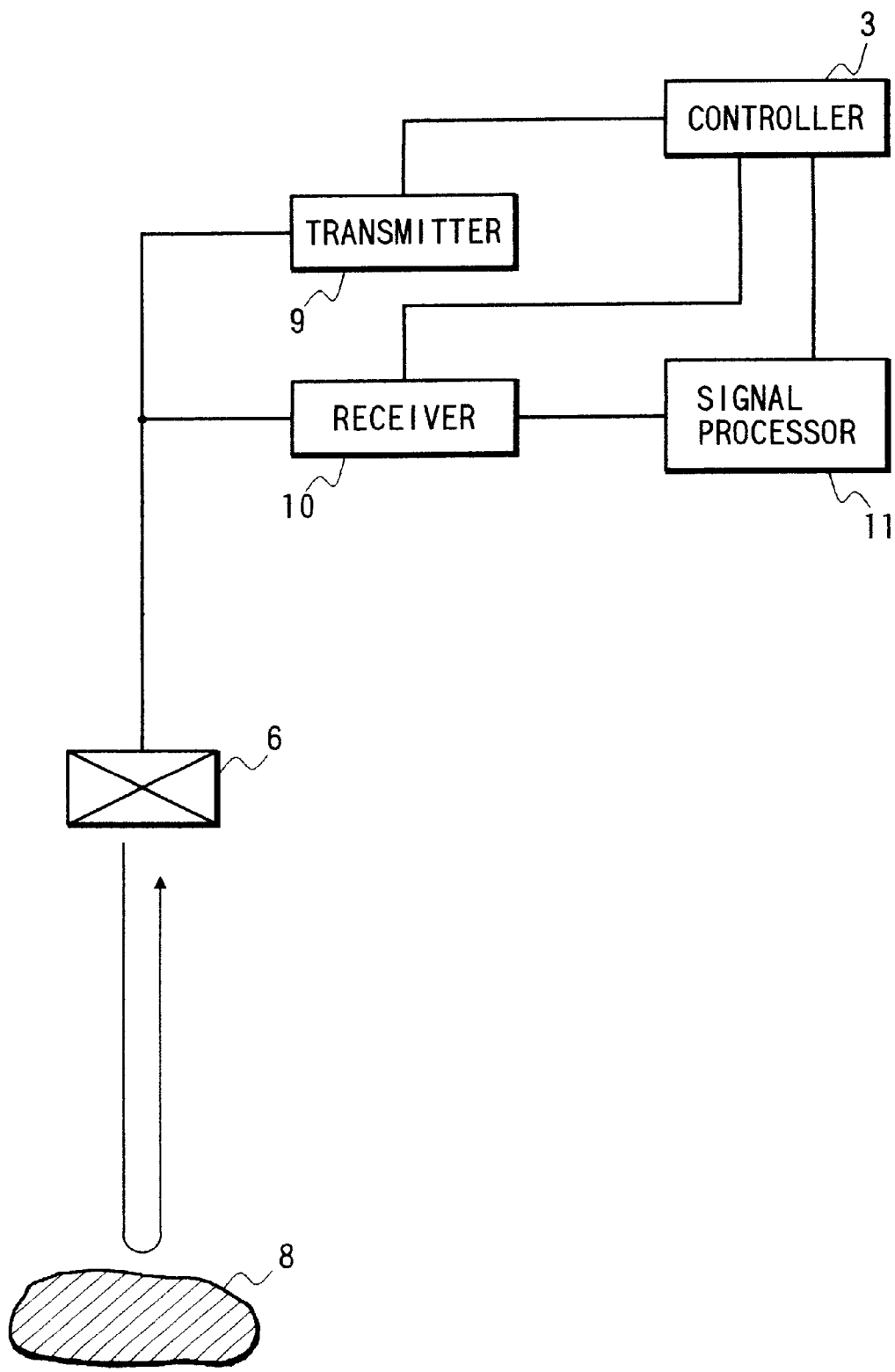
FIG. 1 shows a block diagram showing an ultrasonic distance measuring device according to a first embodiment of the present invention.

FIG. 1 is a block diagram showing an ultrasonic distance measuring device according to the first embodiment of the present invention. In the figure, reference numeral 6 designates a probe; 8, an object to be detected; 9, a transmitter; 10, a receiver; 3, a controller portion; and 11, a signal processor portion. In the specification, the object 8 is present in an ultrasonic wave propagating medium, viz., in the air, in the water, or in a solid. The probe 6 is connected to the transmitter 9 and the receiver portion 10. The receiver portion 10 is connected to the signal processor portion 11. The controller portion 3 is connected to the transmitter 9, the receiver portion 10, and the signal processor portion 11.

The signal processor portion 11 contains a memory therein (not shown), which stores various results of computing operations by the signal processor portion 11 and input signals received by the signal processor portion 11.

The controller portion 3 receives a signal representative of a processing status from the signal processor portion 11, and sends control signals to the transmitter 9, the receiver portion 10, and the signal processor portion 11 for controlling them.

Figure 2:
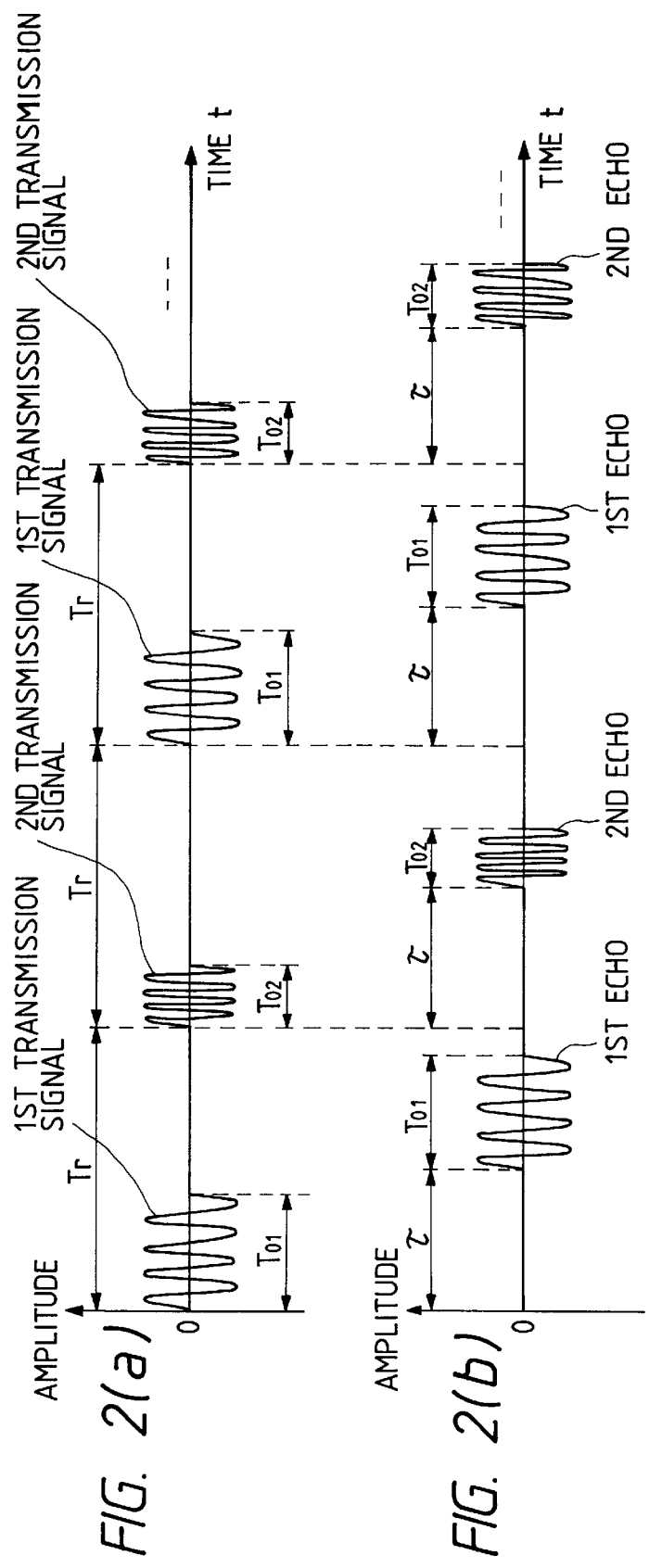
FIGS. 2(a) and 2(b) show waveform diagrams useful in explaining the operation of the ultrasonic distance measuring device of the first embodiment.

FIG. 2 is a waveform diagram useful in explaining the operation of the ultrasonic distance measuring device shown in FIG. 1. FIG. 2(a) is a waveform diagram showing a transmission signal, which is generated by the transmitter 9 to excite the probe 6. FIG. 2(b) is a waveform diagram showing a reflection echo from the object 8.

Figure 3:
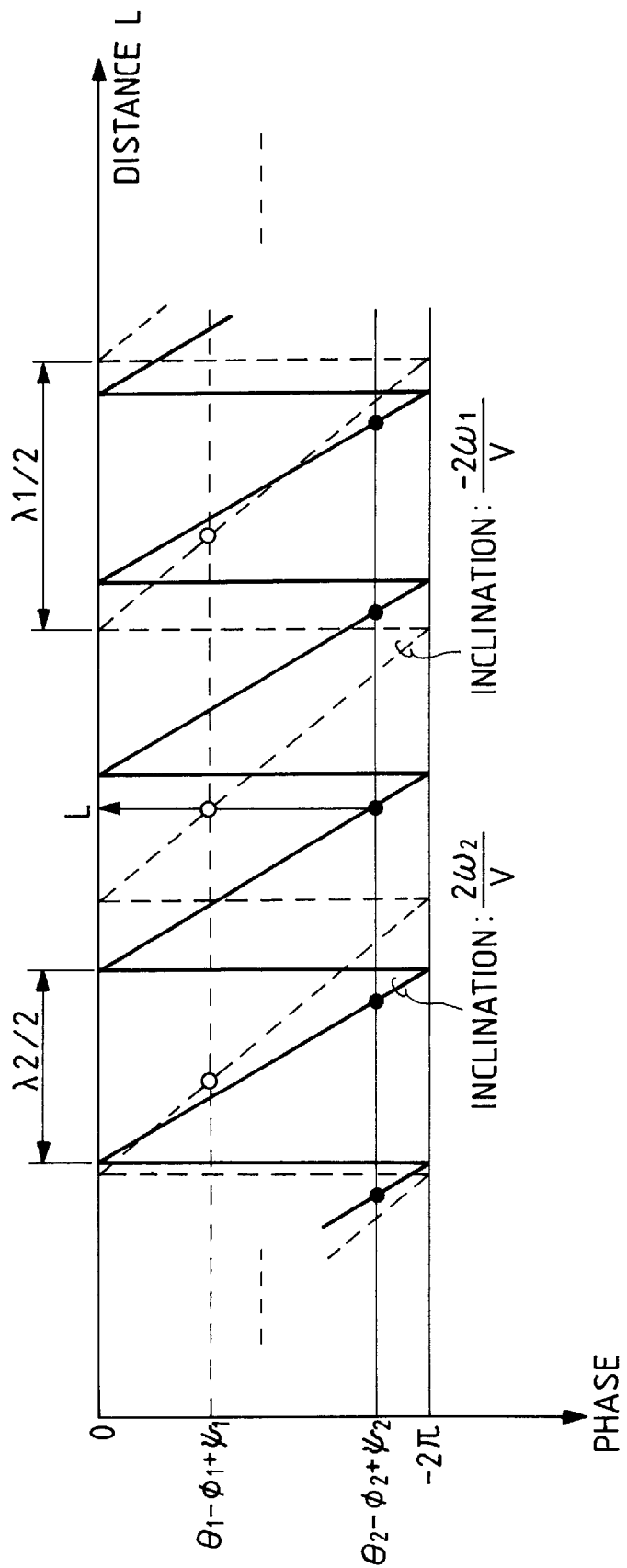
FIG. 3 shows a characteristic diagram useful in explaining a signal processing procedure in the first embodiment.

FIGS. 3 and 4 are characteristic diagrams useful in explaining signal processings in the signal processor portion 11.

FIG. 5 is a waveform diagram used for explaining a signal processing in the signal processor portion 11.

The operation of the first embodiment will be described. A transmission signal shown in FIG. 2(a) is generated by the transmitter 9. The transmission signal consists of a burst signal of the carrier angular frequency ω1 and another burst signal of the carrier angular frequency ω2. The two burst signals are alternately repeated at the transmission repetitive periods Tr. The frequencies corresponding to the angular frequencies ω1 and ω2 are denoted as f1 and f2.

In the present embodiment, the angular frequency ω1 is selected to be smaller than the angular frequency ω2. The relationship between these frequencies is not limited to this, but any other frequency relationship is allowed if these frequencies are not equal.

In the specification, the burst signal involves any type of signals of which the duration is finite. Signals having waveforms as shown in FIGS. 5(b) and 5(c), FIGS. 11(a) and 11(b), and FIGS. 13(c) and 13(d), which are to be described later, are also involved in the burst signal.

The probe 6 is excited by the transmission signal shown in FIG. 2(a), to thereby emit an ultrasonic pulse signal toward an object 8. The waveform of the ultrasonic pulse signal is different from the waveform of the transmission signal shown in FIG. 2(a) since the frequency band width of the probe 6 is finite. We will proceed with the description on the assumption that the band width of the probe 6 is sufficiently broad and hence the waveform of the ultrasonic pulse is approximate to that of the transmission signal, for ease of explanation. It is assumed further that the waveform of an echo, which is received in the form of an electrical signal by the probe 6, is also approximate to that of the ultrasonic pulse emitted by the probe 6.

The ultrasonic pulse reflected by the object 8 is received by the probe 6. The received echo signal, as shown in FIG. 2(b), consists of a burst signal of the carrier angular frequency $\omega_1$ and another burst signal of the carrier angular frequency $\omega_2$. The two burst signals are alternately repeated at the transmission repetitive periods. In the figure, $\tau$ indicates a time taken for the ultrasonic pulse, which is emitted from the probe 6, to travel to and from the object 8. The echo signal is amplified by the receiver portion 10, and then transmitted to the signal processor portion 11. The controller portion 3 is provided for controlling the operation of the respective circuitry portions in the ultrasonic distance measuring device.

During the transmission repetitive period at which the burst signal of the carrier angular frequency $\omega_1$ is transmitted, a transmission signal expressed by $s_1(t)$ is given by the following equation (1)

$$s_1(t) = \sin(\omega_1 t + \phi 1), \quad 0 \leq t \leq T_{01}, \tag{1}$$
$$= 0, \quad t > T_{01}$$

where t: Time $\phi_1$: Fixed phase $T_{01}$: Duration of the burst signal of the carrier angular frequency $\omega_1$ In the present embodiment, the amplitude of the burst signal is selected to be 1, for simplicity. If so selected, the generality will be kept in the description to follow. In the waveform illustrated in FIG. 2(a), the phase $\phi_1$ is zero (0); however, it may be set to a preset value under control by a signal from the controller portion 3. Generally, there is no reason to set the phase $\phi_1$ to zero. The transmission signal $s_1(t)$ will be referred to as a first transmission signal.

The received echo signal, expressed by $\gamma_1(t)$, is given by the following equation (2)

$$\gamma_1(t) = A(\omega_1)\sin(\omega_1 t + \phi 1 - 2L\omega_1 / V), \tag{2}$$
$$\tau \leq t \leq \tau + T_{01},$$
$$= 0, \quad 0 \leq t < \tau \text{ and } t > \tau + T_{01}$$

where $A(\omega_1)$: constant, which depends on the frequency.

L: distance when the ultrasonic pulse travels from the probe 6 to the object 8

V: sonic speed of the ultrasonic wave when it travels in the ultrasonic wave propagating medium The received echo $\gamma_1(t)$ will be referred to as a first echo.

The signal processor portion 11 produces two reference signals $u_{1s}(t)$ and $u_{1c}(t)$ expressed by the following equations (3.a) and (3.b)

$$u_{1s}(t)=\sin(\omega_1 t+\psi_1) \tag{3.a}$$

$$u_{1c}(t)=\cos(\omega_1 t+\psi_1) \tag{3.b}$$

where $\psi_1$: fixed phase.

The fixed phase $\psi_1$ is set to a preset value under control by a signal from the controller portion 3. The reference signals $u_{1s}(t)$ and $u_{1c}(t)$ will be referred to as a first reference signal of the first echo and a second reference signal of the first echo, respectively.

In the signal processor portion 11, the first echo $\gamma1(t)$ is multiplied by the first reference signal $u_{1s}(t)$ of the first echo. The result of the multiplication is $$\gamma 1(t) \cdot u_{1s}(t) = [A(\omega_1)/2]\cos(\phi_1 - 2L\omega_1 / V - \psi_1) - \tag{4}$$
$$[A(\omega_1)/2]\cos(2\omega_1 t + \phi_1 - 2L\omega_1 / V + \psi_1),$$
$$\text{for } \tau \leq t \leq \tau + T_{01},$$
$$= 0$$
$$\text{for } 0 \leq t < \tau, \text{ and } t > \tau + T_{01}$$

The frequency components present near the angular frequency $2\omega_1$ are filtered out by a filter. The signal $g_1(t)$ outputted from the filter corresponds to the first term in the right side of the equation (4).

In the range of $\tau \leq t \leq \tau + T_{01}$, $$g_1(t)=[A(\omega_1)/2] \cos(\phi_1-2L\omega_1/V-\psi_1) \tag{5}$$

When $0 \leq t < \tau$ and $t > \tau + T_{01}$, the output of the filter is zero (0), viz., $g_1(t)=0 (0 \leq t < \tau$ and $t > \tau + T_{01})$.

Similarly, the signal processor portion multiplies the first echo $\gamma_1(t)$ by the second reference signal $u_{1c}(t)$ of the first echo. The frequency components near the angular frequency $2\omega 1$ are filtered out by the filter. The signal outputted from the filter is denoted as $h_1(t)$. When $\tau \leq t \leq \tau + T_{01}$, the output signal $h_1(t)$ is given by $$h_1(t)=[A(\omega_1)/2] \sin(\phi_1-2L\omega_1/V-\psi_1) \tag{6}$$

When $0 \leq t < \tau$ and $t > \tau + T_{01}$, the filter output $h_1(t)$ is zero (0), viz., $h_1(t)=0 (0 \leq t < \tau$ and $t > \tau + T_{01})$.

An envelope of the first echo and a phase thereof are computed by using the filter output signals $g_1(t)$ and $h_1(t)$. The envelope is computed in the following way. $g_1(t)$ is squared, and $h_1(t)$ is squared. The results of squaring those filter output signals are added together. The result of the addition is doubled. Thereafter, the result is raised to the ½th power. Consequently, when $\tau \leq t \leq \tau + T_{01}$, an envelope having a value of $A(\omega 1)$ is obtained, and when $0 \leq t < \tau$ and $t > \tau + T_{01}$, an envelope having a value of zero is obtained.

The phase can be obtained by a simple trigonometrical function since the sine component and cosine component are obtained from $g_1(t)$ and $h_1(t)$. The resultant phase $\theta_1$ is given by $$\theta_1=-2L\omega_1/V+\phi_1-\psi_1+2n\pi \tag{7}$$

where n: integer.

During the transmission repetitive period at which the burst signal of the angular frequency $\omega_2$ is transmitted, the received echo signal is similarly processed by the signal processor portion 11. If a time origin is shifted by the quantity of the transmission repetitive period T$\gamma$, the generality will not be lost in the description. Hence, the time origin is set at a time point where the transmission signal of the angular frequency $\omega_2$ is generated. The transmission signal is denoted as $s_2(t)$; the fixed phase, as $\phi_2$; and the echo, as $\gamma_2(t)$. The transmission signal $s_2(t)$ and the echo $\gamma_2(t)$ will be referred to as a second transmission signal and a second echo, respectively. The transmission signal $s_2(t)$ and the second echo $\gamma_2(t)$ are expressed by the right sides of the equations (1) and (2) in which $\omega_1$ is replaced by $\omega_2$, $\phi_1$ is replaced by $\phi_2$, and $T_{01}$ is replaced by $T_{02}$.

The signal processor portion 11 generates two reference signals, which are formed by replacing $\omega_1$ by $\omega_2$ and $\psi_1$ (fixed phase) by $\psi_2$ in the right sides of the equations (3.a) and (3.b). These reference signals are expressed by $u_{2s}(t)$ and $u_{2c}(t)$, respectively. The reference signals $u_{2s}(t)$ and $u_{2c}(t)$ will be referred to as a first reference signal and a second reference signal, respectively.

In the signal processor portion 11, the second echo $\gamma_2(t)$ is multiplied by the first reference signal $u_{2s}(t)$ of the second echo, the second echo $\gamma_2(t)$ is multiplied by the second reference signal $u_{2c}(t)$ of the second echo, and the frequency components present near the angular frequency $2\omega_2$ are filtered out. As a result, signals are formed which have each a value of 0 in the time ranges of $0 \leq t < \tau$ and $t > \tau + T_{02}$, and which have values given by the right sides of the equations (5) and (6) in which $\omega_1$ is replaced by $\omega_2$, $\phi_1$ is replaced by $\phi_2$, and $\psi_1$ is replaced by $\psi_2$. These signals are expressed by $g_2(t)$ and $h_2(t)$, respectively.

The computing operations to obtain an envelope and a phase of the second echo are performed using the results $g_2(t)$ and $h_2(t)$ of the computing operations as in the case of the first echo.

The result of the computing operation provides an envelope which has a value of $A(\omega_2)$ when $\tau \leq t \leq \tau + T_{02}$, and zero when $0 \leq t < \tau$ and $t > \tau + T_{02}$.

The resultant phase $\theta_2$ is given by the following (8)

$$\theta_2 = -2L\omega_2/V + \phi_2 - \psi_2 + 2m\pi \quad (8)$$

where m is an integer.

In the equations (7) and (8), the fixed phases $\phi_1$, $\psi_1$, $\phi_2$, and $\psi_2$ are already known. However, the integers n and m are unknown. If the integers n and m are known, $\omega_1$ and $\omega_2$ are known. Therefore, if sonic speed V is already known, distance L can be computed using the measured phases $\theta_1$ and $\theta_2$ by the equation (7) or (8).

In other words, actual distance L is computed by using distance $L_1$ based on the measured phase $\theta_1$ (L given by the equation (7)) and distance $L_2$ based on the measured phase $\theta_2$ (L given by the equation (8)).

A signal processing procedure to set up the integers n and m that is carried out in the signal processor portion 11 will be described. FIG. 3 is a characteristic diagram useful in explaining this signal processing procedure. In FIG. 3, the abscissa represents distance L and the ordinate represents phase. In the figure, straight lines inclined at $-2\omega_1/V$ are indicated by bold dotted lines. These lines are based on the first echo. When L=0, those lines pass through the origin. These straight lines are depicted such that when a value of $-2\omega_1 L/V$ exceeds $-2\pi$, the lines are translated along the ordinate so that the value falls certainly within the range between 0 and $-2\pi$. For this reason, those lines are depicted in the form of a triangular characteristic curve. The period of the triangular characteristic curve is expressed by $\lambda_1/2$ where $\lambda_1$ indicates one wavelength of the angular frequency $\omega_1$ in an ultrasonic wave propagating medium.

In FIG. 3, straight lines inclined at $-2\omega_2/V$ are indicated by bold solid lines. These lines are based on the second echo. These straight lines are depicted such that when a value of $-2\omega_2 L/V$ exceeds $-2\pi$, the lines are translated so that the value falls certainly within the range between 0 and $-2\pi$. The period of the triangular characteristic curve is expressed by $\lambda_2/2$ where $\lambda_2$ indicates one wavelength of the angular frequency $\omega_2$ in an ultrasonic wave propagating medium.

As described above, a value of $\theta_1 - \phi_1 + \psi_1$ is known from the result of the signal processing by the signal processor portion 11. A horizontal straight line crossing this value is indicated by a thin dotted line in FIG. 3. Points where the thin dotted line crosses the bold dotted lines are marked with white circles. A plural number of the points of the intersection exist. In the equation (7), the fact that the integer n is unknown indicates the fact that the point of the intersection that is true is unknown.

Similarly, a horizontal straight line crossing a value of $\theta_2 - \phi_2 + \psi_2$ which is obtained by the signal processor portion 11, is indicated by a thin solid line. Points where the thin solid line crosses the bold solid lines are marked with black circles. These points of the intersection are also plural in number. In the equation (8), the fact that the integer m is unknown indicates the fact that the point of the intersection that is true is unknown.

The white circles defined by $\theta_1 - \phi_1 + \psi_1$ and the black circles defined by $\theta_2 - \phi_2 + \psi_2$ are periodically present along the abscissa; however, the period of the white circles is different from that of the black circles.

Distance L from the probe 6 to the object 8 is invariable, not depending on the frequency, as a matter of course. Therefore, at the position corresponding to the distanced L from the probe 6 to the object 8 on the abscissa in FIG. 3, a position on the abscissa, which corresponds to the white circle obtained from the value of $\theta_1 - \phi_1 + \psi_1$, ought to be coincident with a position on the abscissa, which corresponds to the white circle obtained from the value of $\theta_2 - \phi_2 + \psi_2$.

When a black circle and a white circle of which the positions corresponding to those obtained from the values of $\theta_1 - \phi_1 + \psi_1$ and $\theta_2 - \phi_2 + \psi_2$ are coincident with each other on the abscissa (this combination of the black and white circles will be referred to as a specific circle combination) are selected from among those black and white circles, each of the values of the combination of the black and white circles on the abscissa indicates a distance L to be measured.

In FIG. 3, the specific circle combination is the combination of the black and white circles, which lie on a line with an arrow. The value indicated by the arrow head indicates the measured distance L.

An accuracy of the distance thus measured is determined by a measuring accuracy of the phase, as seen from the above description, and is extremely high. In this case, the resolution is smaller than one wavelength.

In the instance shown in FIG. 3, only one combination of the black and white circles of which the positions on the abscissa are coincident with each other is present, but where the abscissa is further longer, a plural number of the combinations of the black and white circles are possibly present. FIG. 4 is a characteristic diagram which is similar to that of FIG. 3, but has a longer abscissa than the latter. Also in FIG. 4, the combinations of the black and white circles lying on the lines with heads each correspond to that combination, as in the case of FIG. 3. As shown, a plural number of the specific circle combinations periodically appear.

The period at which the specific circle combinations appear is integer times the quantity of $\pi V/\Delta\omega$ where $\Delta\omega$ is a difference between the angular frequencies $\omega_1$ and $\omega_2$. In FIG. 4, the period is expressed by $q\pi V/\Delta\omega$ where q is an integer. The period is also equal to be integer times the quantity of $\lambda_1 \cdot \lambda_2/(2(\lambda_1 - \lambda_2))$ where $\lambda_1$ and $\lambda_2$ are wavelengths and the former is longer than the latter. In an example where $\lambda_1=3$ mm and $\lambda_2=2.8$ mm, the period is 21 mm. In another example where $\lambda_1=7.1$ mm and $\lambda_2=4.0$ mm, the period is 142 mm. As seen from these figures, the value of the period is satisfactorily larger than that of the wavelength.

Therefore, of those period, a period containing a measured distance must be specified in another method. If it is specified, by detecting the specific circle combination, viz., the combination of a black circle and a white circle of which the positions are coincident with each other on the abscissa, a true distance L can be obtained from the value of the black circle or the white circle on the abscissa.

A method for specifying the measured-distance contained period will be described. As referred to above, the specific circle combinations appear at the periods of $q\pi V/\Delta\omega$. If the order of the value of a distance to be measured is already known and the value of $q\pi V/\Delta\omega$ is distinguishable where the distance is expressed in the order of the value, it is easy to select a candidate for the measuring value, or a true value from among those candidates of the distance, while taking into consideration the order of the value of the measured distance. In this case, a process to accurately specify the measured-distance contained period as will be described later may be omitted.

As already referred to in connection with the numerical examples, the period at which the specific circle combinations appear is satisfactorily longer than the wavelength. This fact implies that it is easy to specify the measured-distance contained period.

The process for specifying the measured-distance contained period is performed by making use of information on the amplitude of the echo and its envelope. The period specifying process will be described in detail with reference to FIG. 5. FIGS. 5(a) to 5(d) are waveform diagrams for explaining the procedure to specify the measured-distance contained period. In those figures, the diagrams depicted in the lower part show the waveforms representative of amplitude variations of received echo signals appearing at the output the receiver portion 10 and the waveform of an envelope (FIG. 5(d)) produced by the signal processor portion 11 after it processes the received echo signal in the above-mentioned signal processing manner. The abscissa of those diagrams represents distance, while the ordinate represents the amplitude of each of those signals. The distance represented by the abscissa, when it is divided by sonic speed V, indicates time. When the echo and envelope are directly observed by an oscilloscope, this time corresponds to the half of the actual time represented by the abscissa on the oscilloscope screen. In the diagrams in the upper part in FIGS. 5(a) to 5(d), the abscissa represents distance, and the ordinate represents nothing in particular. In those upper diagrams, a mark "X" indicates a position where the arrow head of each line with the arrow comes in contact with the abscissa (distance L) in FIG. 4. In other words, "X" indicates the positions on the abscissa, which correspond to the specific circle combinations appear at the periods each of which is integer times the quantity of $\pi V/\Delta\omega$.

Figure 5A:
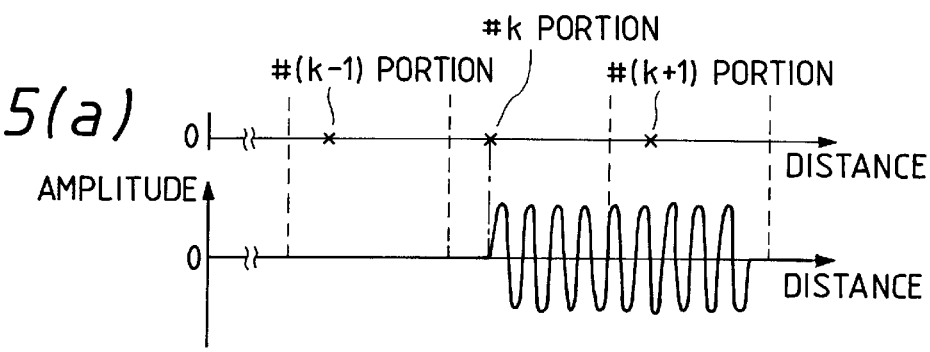
FIGS. 5(a) to 5(d) show waveform diagrams useful in explaining the signal processing procedure in the first embodiment.

FIG. 5(a) shows a process for specifying the measured-distance contained period by making use of information on the rising part of a waveform representative of an amplitude variation of the echo signal. In FIG. 5(a), what we want to know is which of the positions indicated by "X", which appear at the periods each of which is integer times as large as the quantity of $\pi V/\Delta\omega$, is true. In FIG. 5(a), a segmental portion of the k-th period, which is counted from the origin along the abscissa, is referred to as a # k-th portion where k is a natural number. The rising part of the waveform of the echo signal, depicted in the lower part in FIG. 5(a) is present in the # k-th portion. Therefore, it can be determined that the position indicated by X in the # k-th portion is true.

Either of the first echo or the second echo may be used for determining the true position. The echo which is easier to find the rising part is preferably selected. The same thing is true for the cases of FIGS. 5(b) to 5(d).

Figure 5B:
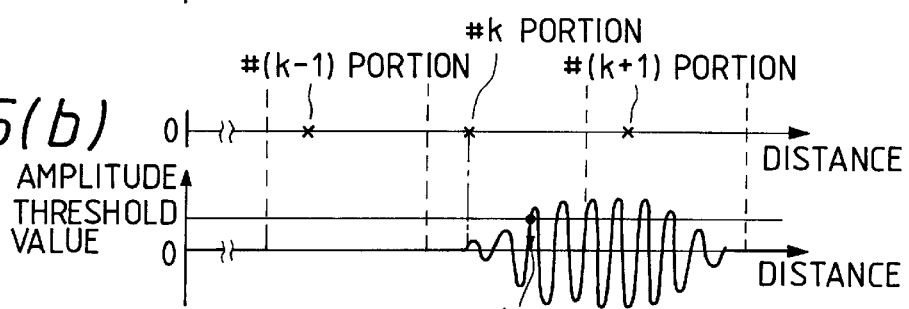

FIG. 5(b) is a diagram showing the waveform of an echo signal of which the rising part is gentle, the waveform being depicted in the same coordinate system as that in FIG. 5(a). Actually, the following echo signals are frequently experienced: an echo signal of a waveform that is gentle in the rising and falling parts thereof as shown in FIG. 5(b), and an echo signal (not shown) of which the envelope amplitude is large in the rising and falling parts but is small in the mid part between them. Such a deformation of the waveform (waveform deformation) of the echo signal, when compared with the waveform of the transmission signal, is due to the fact that the frequency band-width of the probe 6 is finite and that an attenuation of the ultrasonic wave in the ultrasonic wave propagating medium has a frequency dependency. When a probe or the ultrasonic wave propagating medium is changed to another, the waveform deformation becomes quite different on use conditions. In this case, the waveform deformation reaches to such an extent that the original waveform is lost.

The conventional art handles the echo signal of such a waveform such that a threshold value is set at the rising part, and a position of an object 8 is obtained by measuring a time point where a curve of an amplitude variation of an echo signal crosses the threshold value. In the case of FIG. 5(b), the conventional art mistakenly understands that a position denoted as Lo is a correct position of the object. Further, when the waveform deformation greatly varies on use conditions, it is difficult to select a position on the waveform at which the threshold value is to be set. In the conventional art in which a threshold value is provisionally set for measurement, the measurement results show that further improvement is required for accuracy and reliability.

On the other hand, in the first embodiment, information on the rising part of the echo signal is used only for determining the portion containing the true X mark. In FIG. 5(b), the waveform of the echo signal rises at a position near the position indicated by X in the # k-th portion. In the # (k+1)th portion, the echo signal continues but does not rise near the X position. In the # (k−1)th portion, the echo signal is not yet received near the X position. In the first embodiment, noting this fact, a threshold value is set at a position, which is a preset value lower than the peak value of the amplitude of the echo signal. A time point where the amplitude variation curve crosses the threshold value is detected (the time point is expressed in terms of distance in FIG. 5(b)). The detected time point is a distance denoted as Lo. This distance is located within the # k-th portion. Hence, the mark X in the # k-th portion is true.

As described above, even when the rising time of the echo signal is approximately detected, the process to specify the measured-distance contained period normally operates by the approximate rising time detected. Accordingly, even when the waveform deformation of the echo signal is great to such an extent that it is impossible to accurately detect a rising time of the echo signal, the specifying process can accurately specify the measured-distance contained period. This fact implies that the specifying process of the present embodiment is superior to the conventional one in the accuracy and reliability of the measurement.

Figure 5C:
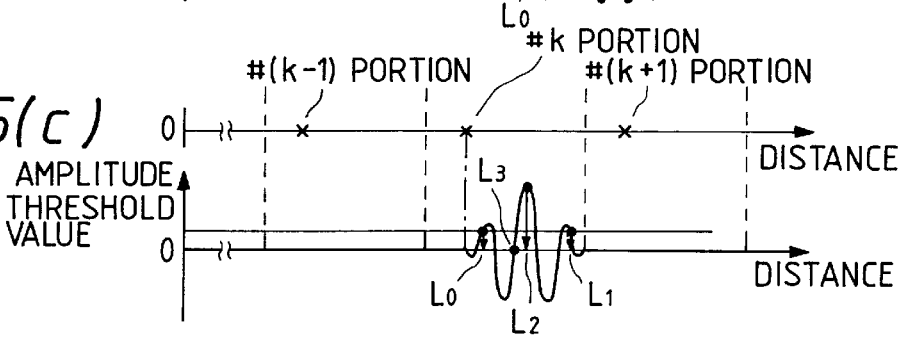

FIG. 5(c) is a diagram showing the waveform of an echo signal of which the pulse width is shorter than the period of $q\pi V/\Delta\omega$ (q:integer), the waveform being depicted in the same coordinate system as that in FIG. 5(b). As shown in FIG. 5(c), the pulse width of a transmission signal is selected such that the pulse width of the echo is shorter than the period. If the pulse width is so selected, various types of information other than the rising part of the echo waveform that is described referring to FIG. 5(b) may be used for specifying the measured-distance contained period. These types of information are, for example, information on a time point where the amplitude of the echo is peaked, information on a time point where the amplitude variation curve crosses a zero point, and information of time of the rising part of the echo waveform. Any or a combination of those types of information may be used for specifying the measured-distance contained period. When those types of information are combined, the result of determining the true position of the mark X is more accurate.

The case of FIG. 5(c) will further be described in detail. The following distances, which correspond to various points on an amplitude variation curve of the echo in the rising and falling parts thereof, as shown in FIG. 5(c), are measured: distance Lo and L1 corresponding to points where the amplitude curve crosses the threshold value, distance L2 corresponding to a point where the amplitude is peaked, and distance L3 corresponding to a point where the amplitude variation curve crosses a zero point immediately before the amplitude is peaked. Since these distances are all within the # k-th portion, the true position of X can be determined by using any or a combination of the distances. In a case where some of the distances are out of the # k-th portion, the true position can synthetically be determined by additionally using a majority-decision process.

The values of the detected distances used for determining the true position may be approximate, not exactly, as in the case of FIG. 5(b) where information on the rising part of the amplitude variation curve is used.

A plural number of points where the curve of the echo crosses the zero point are present. Those zero-crossing points including a zero-crossing point immediately before the echo amplitude is peaked may be used for the true position determination process.

Figure 5D:
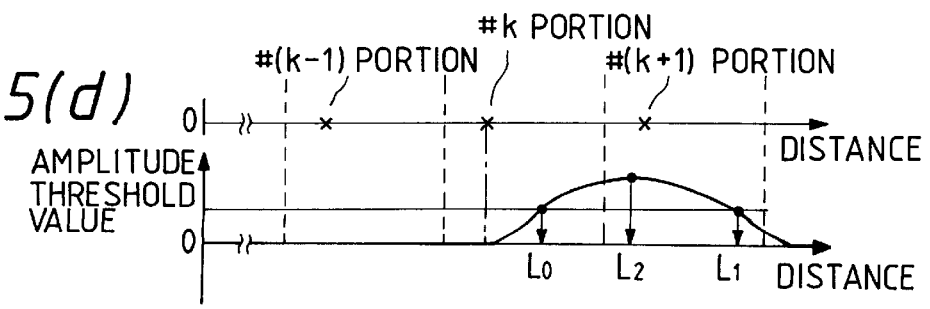

FIG. 5(d) is a waveform diagram for explaining the true-position determining process by information on the envelope of the echo, the waveform being depicted in the same coordinates system as in FIGS. 5(a) to 5(c). As shown, an envelope of an echo signal is depicted in FIG. 5(d), while the waveforms each representative of an amplitude variation of the echo signal are depicted in FIGS. 5(a) to 5(c). As in the case using information on the amplitude of the echo, a threshold value is set, and distances Lo and L1 corresponding to points where a curve of the envelope crosses the line representative of the threshold value in the rising part and the falling part of the envelope curve, and distance L2 corresponding to a point where the envelope curve is peaked are detected for the true position determination process. Also in this case, the value of each detected distance may be approximate.

An overall operation for a signal processing procedure of the ultrasonic distance measuring device, which has been described with reference to FIGS. 1 to 5, will be described with reference to FIGS. 6 to 8.

Figure 6:
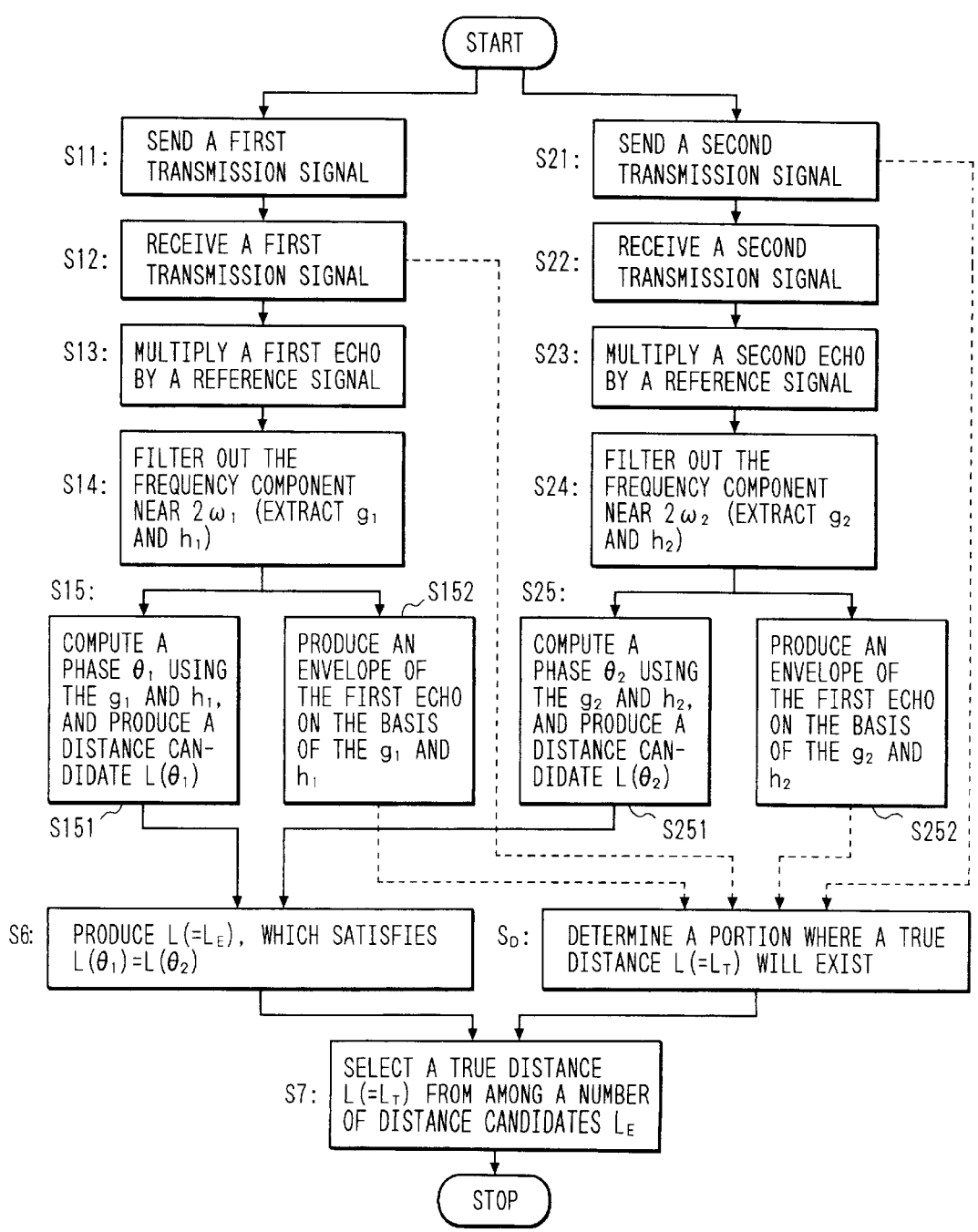
FIG. 6 shows a flowchart showing a first signal processing procedure in the first embodiment.

A flowchart shown in FIG. 6 shows an overall operation for a signal processing procedure of the ultrasonic distance measuring device. The signal processing procedures of the cases of FIGS. 5(a) to 5(d) are all contained in the flowchart.

A signal processing procedure for the first transmission signal, which consists of steps S11 to S15, will first be described.

In the step S11, a first transmission signal $S_1$ of the angular frequency $\omega_1$ is transmitted.

In the step S12, a first echo $\gamma_1(t)$, or the first receiving signal, is received.

In a step S13, the first echo signal is multiplied by the reference signal, and in a step S14, the frequency components near the angular frequency $2\omega_1$, are filtered out by a filter, so that the $g_1$ and $h_1$ are extracted.

In a step S15, exactly in a step S151, a phase $\theta_1$ is computed using the $g_1$ and $h_1$, and a distance candidate $L(\theta_1)$ by the first echo is produced on the basis of the phase $\theta_1$. In a step S152, an envelope of the first echo is produced on the basis of the $g_1$ and $h_1$.

A sequence of the procedural operations of the steps S13, S14 and S15(S151 and S152) is executed in the signal processor portion 11.

The signal processing procedure of a second transmission signal $S_2$ of the angular frequency $\omega_2$ is executed in steps S21 to S25 as in the steps S11 to S15.

Of the numeral 11 attached to S of the step S11, the first number 1 indicates the first signal, and the second number 1 indicates the order of the steps. The same thing is true for S12 to S15, and S21 to S25.

In a step S6, L $(=L_E)$, which satisfies $L(\theta_1)=L(\theta_2)$, is produced on the basis of the distance candidate $L(\theta_1)$ by the first echo, which is based on the phase $\theta_1$, viz., $\theta_1-\phi_1+\psi_1$, and the distance candidate $L(\theta_2)$ by the second echo, which is based on the phase $\theta_2$, viz., $\theta_2-\phi_2+\psi_2$. In other words, a point where the positions of a white circle and a black circle are coincident with each other (this point will be referred to as a coincident point) is obtained.

In a step $S_D$, a portion where a distance candidate corresponding to a true distance will exist is determined on the basis of any of the first echo, the second echo, the envelope of the first echo, and the envelope of the second echo, to thereby obtain the candidate-contained portion. That is, the # 5th portion is obtained.

In a step S7, the coincident point in the candidate-contained portion is selected from among a plural number of the coincident points, and this selected point is produced as a true distance.

In FIG. 6, four input lines are connected to the square block of the step $S_D$ for determining the candidate-contained portion. These input lines are indicated by dotted lines. This means that at least one input line is required. This is equivalent to the connection of an OR gate to the input of the square block of the step $S_D$.

Various timings to execute the step $S_D$ for determining the candidate-contained portion may selectively be used after the signal necessary for the determining operation is obtained, while the relationship of them with the timings to execute the operation of the step S7 is taken into consideration.

In the signal processing procedure of FIG. 6, concurrent operation of the step S6 and the step $S_D$ is allowed. Accordingly, the determining operation may be completed till the result of the computing operation in the step S6 is outputted. Then, the step S7 may be executed immediately after the computing operation of the step S6 is completed.

Generally, the computing time in the step S6 is larger than that in the step $S_D$.

The steps S6, S7, and $S_D$, like the steps S13 to S15 and the steps S23 to S25, are executed in the signal processor portion 11 shown in FIG. 3. The signal processor portion 11 may be realized by a computer operating under control of a program. If required, it may also be realized by hardware units for the respective steps.

In the signal processing procedure shown in FIG. 6, the final step denoted as STOP means that when the true distance is produced in the step S7, the overall measuring operation including the computing operation in the step S6 is properly stopped.

Accordingly, the operations of the steps S151, S152, and S6, particularly the step S6, are continued till the true distance is produced in the step S7. In this sense, a signal indicating that the true distance $L_T$ is produced in the step S7 functions as a computing-operation stop signal in the step S6.

The echo signal and the envelope of the echo signal are both used for determining the candidate-contained portion in the step $S_D$ in FIG. 6. In the latter case using the envelope, the envelope is formed in a manner that the echo signal is multiplied by the reference signal, and the high frequency components (including noise) of the resultant product are removed. In determining the candidate-contained portion, it is preferable to use the envelope than the amplitude since the former is superior to the latter in S/N performance.

The former case using the echo signal does not need the steps S152 and S252 for forming the envelope. Accordingly, the total computing time of the former case is shorter than that of the latter case.

Figure 7:
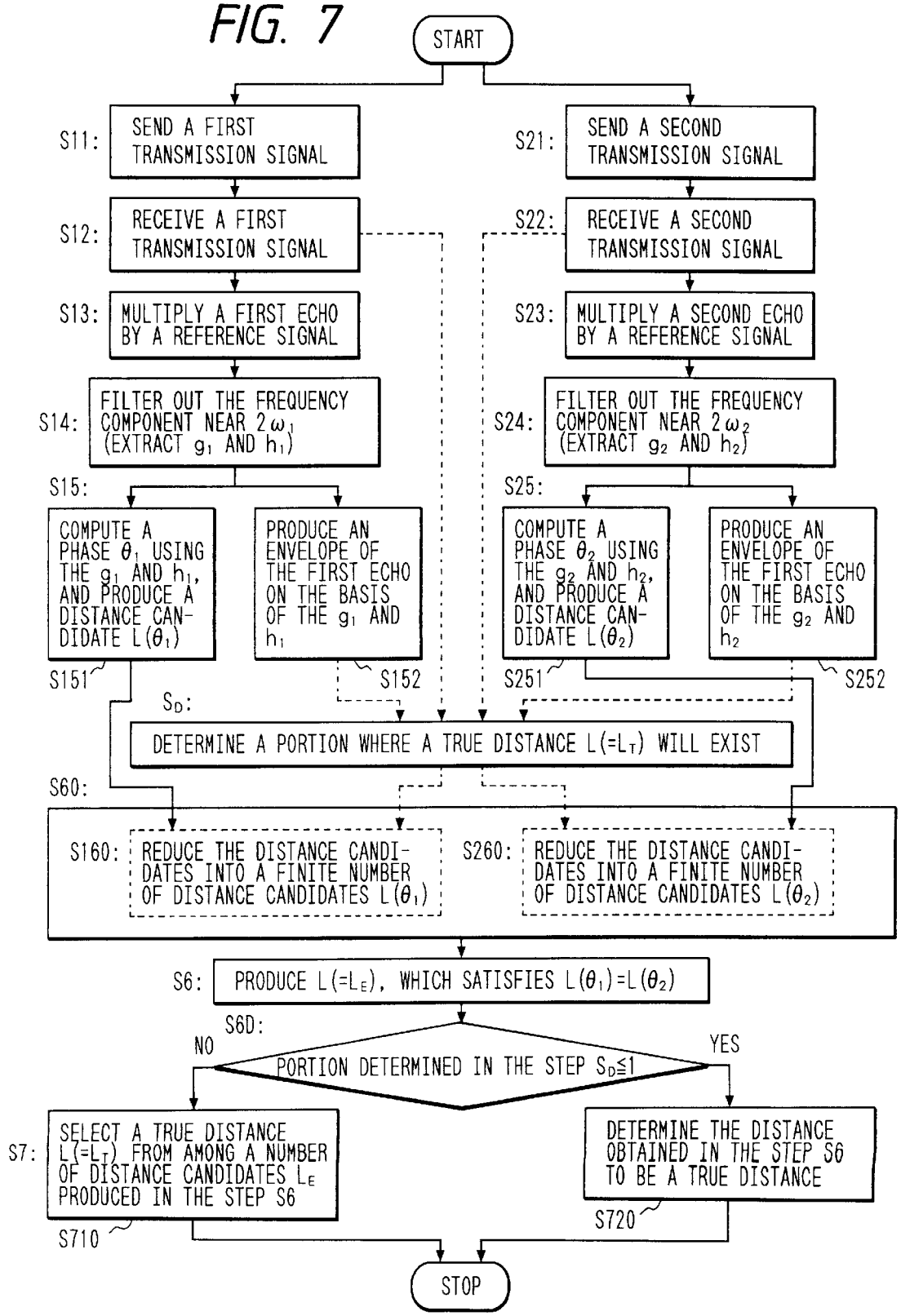
FIG. 7 shows a flowchart showing a second signal processing procedure in the first embodiment.
Figure 8:
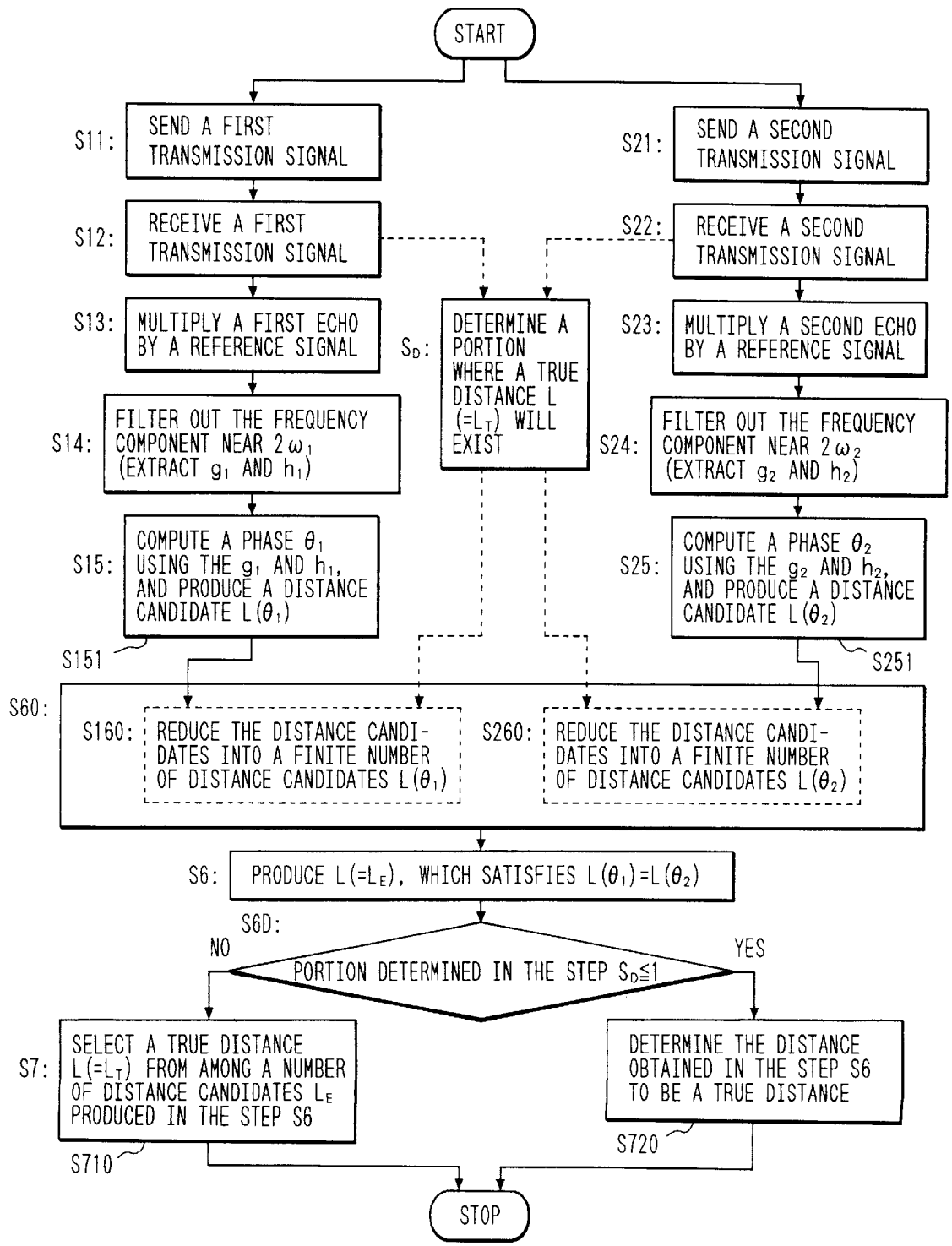
FIG. 8 shows a flowchart showing a third signal processing procedure in the first embodiment.

In FIGS. 7 and 8, the distance candidates $L(\theta_1)$ and $L(\theta_2)$ are reduced into a finite number of distance candidates in steps S160 and S260. Broken lines are used for indicating the connection of the determination results by the step $S_D$ for determining the candidate-contained portion to the steps S160 and S260. Broken lines are also used for depicting the square blocks of the steps S160 and S260. Accordingly, one of the steps S160 and S260 may be omitted as described referring to FIG. 6.

Another signal processing procedure will be described with reference to FIG. 7.

The signal processing procedure subsequent to the step S15 in the flowchart of FIG. 7 is different from that in the flowchart of FIG. 6. The difference of the signal processing procedure follows.

A step S60 contains the steps S160 and S260. The step S160 reduces the number of the distance candidates $L(\theta_1)$ and $L(\theta_2)$ by the first echo, which is produced from the step S151, on the basis of the determination result made by the step $S_D$. In other words, the distance candidates $L(\theta_1)$ and $L(\theta_2)$ are previously limited in number.

Also in the step S260, the distance candidates $L(\theta_2)$ is previously limited in number.

In a step S6, the distance candidates $L(\theta_1)=L(\theta_2)$, or distances $L_E$, are selected from among the limited number of distance candidates.

A step $S_{6D}$ checks as to whether or not the number of the candidate-contained portions determined in the step $S_D$ is 1. If it is 1, the distance obtained in the step S6 is determined to be a true distance (step S720). If it is not 1, a computing operation to select a true distance from among those $L_E$, which are obtained in the step S6 (step S710).

Generally, an infinite number of the combinations of the distance candidates $L(\theta_1)=L(\theta_2)$ are present in the distance candidates $L(\theta_1)$ and $L(\theta_2)$ in the steps S151 and S152. Therefore, the computing operation of selecting the combinations of the distance candidates $L(\theta_1)=L(\theta_2)$ continues unless it is not stopped by a related program, for example. In the procedure of FIG. 7, time for the computing operation is reduced since the number of the distance candidates is reduced to a finite number in the step S60.

The candidate-contained portion determining step $S_D$, the steps S11 to S152, and the steps S21 to S252 in the signal processing procedure in FIG. 7 are the same those in FIG. 6.

In a signal processing procedure of FIG. 8, the process of the step $S_D$ is executed using the first echo signal or the second echo signal. In this case, the steps S152 and S252 for forming the envelopes may be omitted.

The reference signals used in the steps S13 and S23 in FIGS. 6 to 8 are formed in advance corresponding to the first transmission signal $S_1(t)$ and the second transmission signal $S_2(t)$, and stored in a memory located inside or outside the signal processor portion 11, for example. Alternatively, the reference signals may be generated by the signal processor portion 11 when these are required.

2nd Embodiment

Figure 9:
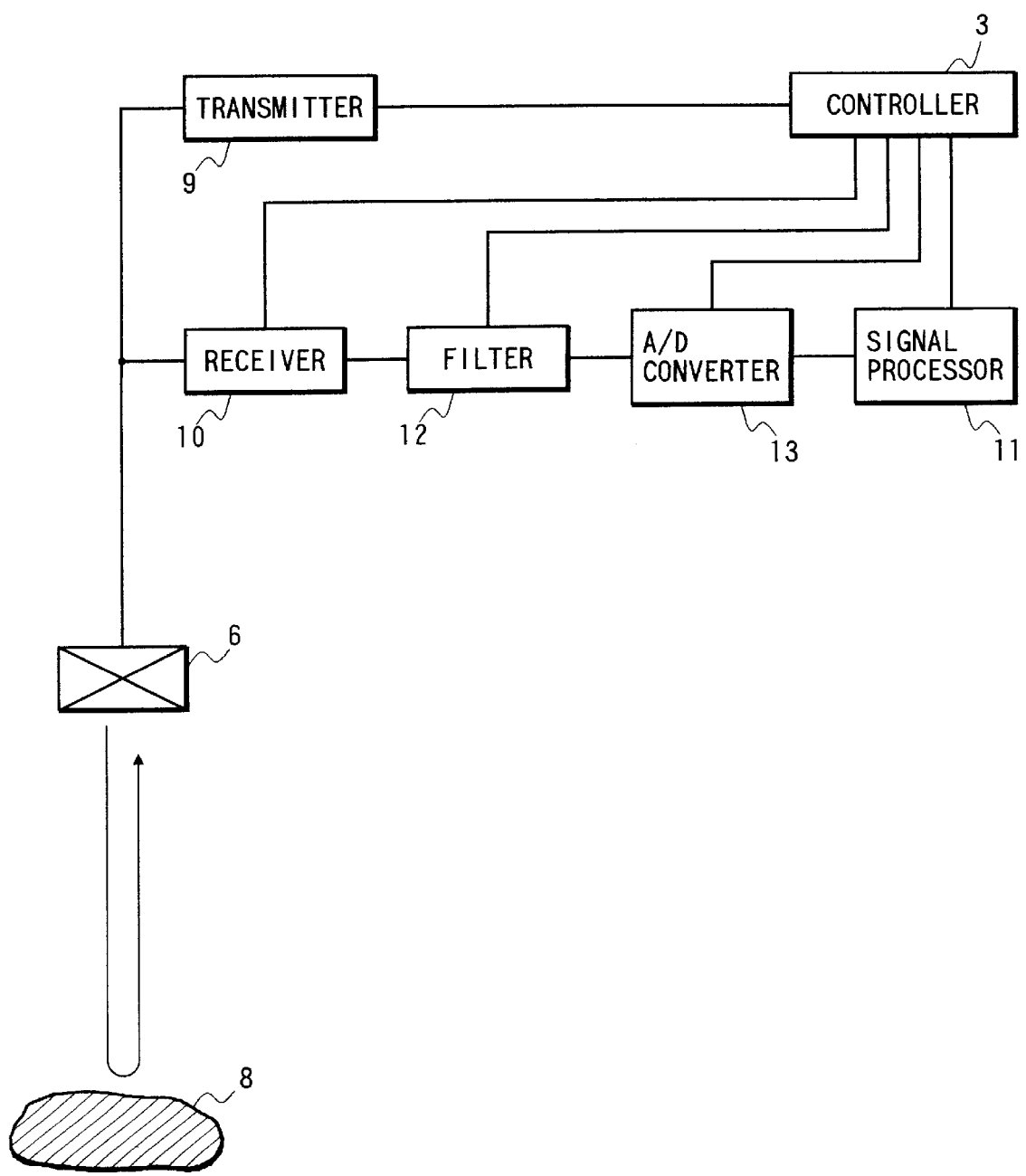
FIG. 9 shows a block diagram showing the arrangement of an ultrasonic distance measuring device according to a second embodiment of the present invention.

The second embodiment of the present invention will be described with reference to FIG. 9. FIG. 9 is a block diagram showing the arrangement of an ultrasonic distance measuring device according to the second embodiment of the present invention. In FIG. 9, reference numeral 12 designates a filter portion, and numeral 13 indicates an A/D convertor portion. The filter portion 12 and the A/D convertor portion 13 are disposed between the receiver portion 10 and the signal processor portion 11. The input terminal and the output terminal of the filter portion 12 are respectively connected to the output terminal of the receiver portion 10 and the input terminal of the A/D convertor portion 13. The output terminal of the A/D convertor portion 13 is connected to the signal processor portion 11. The filter portion 12 and the A/D convertor portion 13 are both connected to the controller portion 3. The remaining construction of the second embodiment is the same as that of the first embodiment.

The operation of the second embodiment will be described. In the second embodiment, as in the first embodiment, the first and the second transmission signal are transmitted to the probe 6. The first and the second echo received by the probe 6 are amplified by the receiver portion 10. The first and the second echo signal, after passing through the receiver portion 10, are inputted to the filter portion 12. The filter portion 12 is a filter of the band-pass type, which allows given frequency components near to the angular frequencies $\omega_1$ and $\omega_2$ to pass therethrough. The frequency characteristic of the filter portion 12 may be selected for the first or second echo signal by a control signal from the controller portion 3. Where the frequency difference of the first and the second echo signal is small, the same filter or the same frequency characteristic may be used for both the echo signals. The first and the second echo signal, after passing through the filter portion 12, are A/D converted by the A/D convertor portion 13, and then transmitted to the signal processor portion 11. The signal processor portion 11 generates the first and the second reference signal of the first echo signal, and the first and the second reference signal of the second echo signal in the form of digital signals, and executes the signal processing procedure through the digital computing operations, which is described in connection with the equation (4) and the subsequent ones in the first embodiment, thereby to obtain distance L.

The effects of the second embodiment and the operation thereof causing the effects will be described. The output signal of the amplifier of the receiver portion 10 suffers from a drift. The drift gradually varies with time, and hence contains a DC component and low frequency components. The output signal of the power amplifier in the transmitter portion 9 leaks into the receiver portion 10. By the called run-on by the amplifier of the transmitter portion 9, the low frequency components containing the DC component are superposed on the received signal.

If the first embodiment is executed in a state that the low frequency components containing the DC component are superposed on the received signal, there is a possibility that the results of detecting the phases and the envelopes of the echoes are deviated from the proper ones and then contains errors. To cope with this, the filter portion 12 located after the receiver portion 10 filters out the unnecessary DC component and the low frequency components. Thus, the second embodiment protects the result of the measurement from those unnecessary components.

In the second embodiment, as the durations of the first and the second transmission signal are longer, the spectra of these signals are narrower. Accordingly, by increasing the durations of the first and the second transmission signal, and narrowing the band-width of the filter, S/N ratios of the first and the second echo signal are improved inversely proportional to the band-width. This is one of the great differences of the second embodiment device from the conventional one. In the conventional device, to improve the S/N ratio, the amplitude of the transmission signal must be set large. However, the circuit elements of the ultrasonic distance measuring device have the limited breakdown voltage performances. In this respect, there is a limit in improving the S/N ratio performance. On the other hand, in the second embodiment, the S/N ratio can be improved by increasing the durations of the first and the second transmission signal, not the amplitudes of the signals. Accordingly, a more circuit design freedom is secured in selecting the circuit elements, for example.

In the second embodiment, the signal processing procedure described in the first embodiment is applied to the first and the second echo signal, to thereby obtain a desired distance through the digital computing operations. Therefore, the detection results are accurate and good in reproducibility. Further, the signal processing process is more flexibly carried out. For example, in a case where the unnecessary frequency components are imperfectly filtered out by the filter, the remaining components may be removed by a digital processing. Other signal processing processes as will be described in other embodiments of the present invention may be used.

3rd Embodiment

Figure 10:
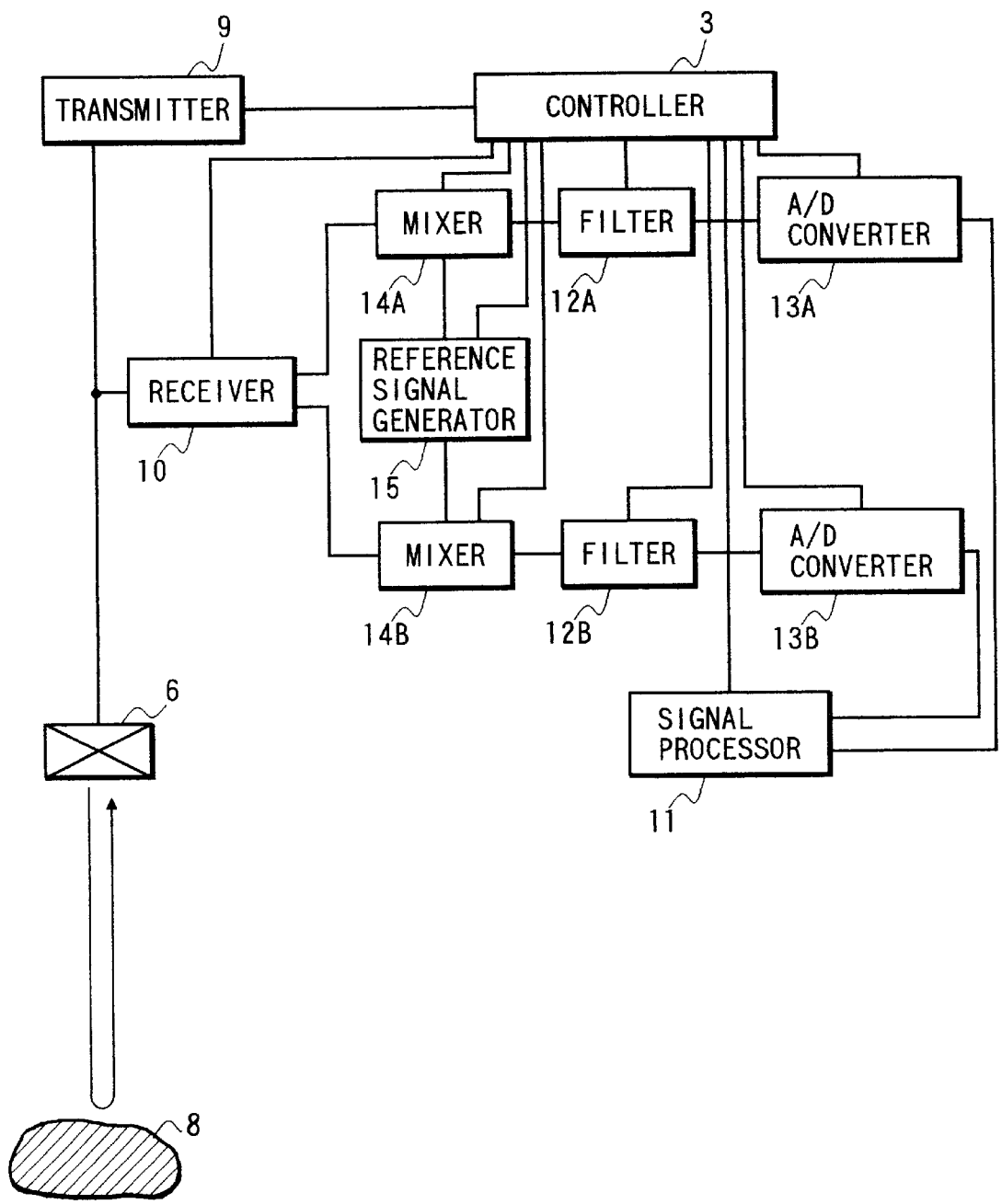
FIG. 10 shows a block diagram showing the arrangement of an ultrasonic distance measuring device according to a third embodiment of the present invention.

A third embodiment of the present invention will be described with reference to FIG. 10. FIG. 10 is a block diagram showing an arrangement of an ultrasonic distance measuring device according to the third embodiment of the present invention. In FIG. 10, reference numerals 14A and 14B designate mixers and numeral 15 designates a reference signal generator portion. 12A and 12B designate filter portions, and 13A and 13B, A/D convertor portions.

In FIG. 10, the receiver portion 10 has two output terminals (referred to the first and the second output terminal of the receiver portion 10). The first and the second output terminal of the receiver portion 10 are connected to the mixer portions 14A and 14B, respectively. The output terminals of the A/D convertor portions 13A and 13B are connected to the signal processor portion 11, respectively. The output terminals of the mixer portions 14A and 14B are connected to the input terminals of the filter portions 12A and 12B, respectively. The output terminals of the filter portions 12A and 12B are connected to the input terminals of the A/D convertor portions 13A and 13B, respectively. The output terminals of the A/D convertor portions 13A and 13B are connected together to the signal processor portion 11.

The reference signal generator portion 15, the mixer portions 14A and 14B, the filter portions 12A and 12B, and the A/D convertor portions 13A and 13B are connected to the controller portion 3. The remaining construction of the third embodiment is the same as of the first embodiment.

The operation of the third embodiment will be described. In the third embodiment, as in the first embodiment, the first and the second transmission signal are transmitted to the probe 6, and the first and the second echo signal received by the probe 6 are amplified in the receiver portion 10. The signal appearing at the first output terminal of the receiver portion 10 is the same as the signal at the second output terminal thereof if the same signal is inputted to the receiver portion 10.

The first echo signal will be described. The first echo signal is amplified by the receiver portion 10, and the amplified one is outputted from the first and the second output terminal of the receiver portion 10, which in turn are transferred to the mixer portions 14A and 14B.

The reference signal generator portion 15 operates in synchronism with the timing of generating the first transmission signal, to thereby produce a first reference signal of the first echo signal and a second reference signal of the first echo signal through the first and the second output terminal thereof. These reference signals are in turn applied to the mixer portions 14A and 14B.

The first echo signal is multiplied by the first and the second reference signal in the mixer portions 14A and 14B. The output signals of the mixer portions are transferred to the filter portions 12A and 12B, respectively. The filter portions 12A and 12B, which are of the low-pass type, filter out the component of the angular frequency $2\omega_1$.

The output signals of the filter portions 12A and 12B are transmitted to the A/D convertors 13A and 13B, respectively. The A/D convertors 13A and 13B convert these signals into digital signals, which in turn are transferred to the signal processor portion 11. These signals received by the signal processor portion 11 correspond to the digitized signals of $g_1(t)$ and $h_1(t)$, which are expressed by the equations (5) and (6) in the first embodiment.

During the transmission repetitive period where the second echo signal is received, the second echo signal is amplified by the receiver portion 10, the amplified echo signal is outputted from the first and the second output terminal of the receiver portion 10. Those output signals are transmitted to the mixer portions 14A and 14B. The reference signal generator portion 15 operates in synchronism with the timing of generating the second transmission signal, to thereby produce a first reference signal of the second echo signal and a second reference signal of the second echo signal through the first and the second output terminal thereof. These first and second reference signals are applied to the mixer portions 14A and 14B, respectively.

The second echo signal is multiplied by the first and the second reference signal of the second echo signals in the mixer portions 14A and 14B. The output signals of the mixer portions are transferred to the filter portions 12A and 12B, respectively. The filter portions 12A and 12B, which are of the low-pass type, filter out the component of the angular frequency $2\omega_1$ during the transmission repetitive period where the second echo signal is received.

The output signals of the filter portions 12A and 12B are transmitted to the A/D convertors 13A and 13B, respectively. The A/D convertors 13A and 13B convert these signals into digital signals, which in turn are transferred to the signal processor portion 11. These signals received by the signal processor portion 11 correspond to the digitized signals of $g_2(t)$ and $h_2(t)$ in the first embodiment.

The signal processor portion 11 executes the signal processing procedure through the digital computing operations, which is described in connection with the equation (5) and the subsequent ones in the first embodiment, thereby to obtain distance L.

The useful effects of the third embodiment and the operation thereof causing the effects will be described. In the third embodiment, the multiplying operations necessary for the signal processing procedure of the first and the second echo signal are carried out in the mixer portions 14A and 14B. The output signals of the mixer portions pass through the filter portions 12A and 12B, and are converted into digital signals by the A/D convertors 13A and 13B. It is noted that the multiplying operations are carried out by the mixer portions 14A and 14B, not the mixer portions 14A and 14B. Therefore, the computing process in the signal processor portion 11 is correspondingly simplified, so that the device operation speed is increased. Further, low frequency operating A/D convertors may be used for the A/D convertors 13A and 13B. This brings about reduction of the device cost. The third embodiment is useful when it is applied to the device using an ultrasonic wave at the frequency of several tens MHz or more, and of several hundreds MHz to 1 GHz frequently used by the ultrasonic microscope.

In the third embodiment above mentioned, the reference signal generator portion 15 generates the first and the second reference signal of the first echo signal and outputs these signals through the first and the second output terminal thereof. The first and the second reference signal of the second echo signal are also outputted through the first and the second output terminal of the reference signal generator portion 15. The reference signal generator portion 15 may have the following construction.

The reference signal generator portion 15 generates a first reference signal of the first echo signal and outputs it through the first output terminal thereof. The first reference signal of the first echo signal is applied to a 90° phase shifter, and inverted in phase or multiplied by −1, to thereby form a second reference signal of the first echo signal. The reference signal generator portion 15 produces the second reference signal through the second output terminal thereof. Similarly, the reference signal generator portion 15 generates a first reference signal of the second echo signal and outputs it through the first output terminal thereof. The first reference signal of the first echo signal is applied to a 90° phase shifter, and inverted in phase or multiplied by −1, to thereby form a second reference signal of the second echo signal. The reference signal generator portion 15 produces the second reference signal through the second output terminal thereof. Since the frequencies of the reference signals of the first echo signal are different from those of the reference signals of the second echo signal, the 90° phase shifters each are designed so as to be able to delay the phase of the reference signal by 90° irrespective of the difference of the frequencies of the reference signals. The reference signal generator portion 15, when incorporated into the ultrasonic distance measuring device, may have the useful effects comparable with those achieved by the third embodiment.

In the reference signal generator portion 15, after the reference signal is phase shifted by the 90° phase shifter, it is inverted in phase or multiplied by −1. The reason for this is that sin (θ−90°)=−cos(θ) and the signal of the right side of this equation is different by 180° from the second reference signal of each of the first and the second echo signal.

Although not illustrated, the third embodiment may be modified such that filter portions 12 as used in the second embodiment are respectively inserted between the receiver portion 10 and the mixer portion 14A and between the receiver portion 10 and the mixer portion 14B. The so modified third embodiment can achieve the useful effects as of the second embodiment.

4th Embodiment

The fourth embodiment of the present invention will be described. In the first to third embodiments, when the first echo signal is multiplied by the first and the second reference signal of the first echo signal, the frequency of each of those reference signals is set to be equal to the carrier frequency of the first echo signal or the carrier frequency of the first transmission signal. Similarly, when the second echo signal is multiplied by the first and the second reference signal of the second echo signal, the frequency of each of those reference signals is set to be equal to the carrier frequency of the second echo signal or the carrier frequency of the second transmission signal. The multiplication operation causes the frequency components near to the DC component and the frequency components near to the frequency two times as high as the carrier frequency. The frequency components near to the DC component are extracted by the filter portion 12 or 12A and 12B. The information on the phase and the envelope of the first and the second echo signal are produced on the basis of the DC component and its near frequency components.

Not only the amplifier of the receiver portion 10 but also the circuit elements of the mixer portions 14A and 14B in the third embodiment suffer from drift gradually varying with time. Further, there is the problem of superposing of the low frequency components including the DC component on the receiving signal by leakage thereof from the transmitter portion 9 to the receiver portion 10. The fourth embodiment of the present invention is directed to eliminate measuring errors caused by those problems.

The fourth embodiment is different from the first to third embodiments in that the frequency of each reference signal is different from the carrier frequency of the echo signal or the transmission signal.

The construction of the fourth embodiment is substantially the same as that of the third embodiment.

The operation of the fourth embodiment will be described. In the fourth embodiment, the first transmission signal $S_1$ at the angular frequency $\omega_1$ is transmitted to the probe, and a first echo $\gamma_1(t)$, which corresponds to the first transmission signal, is received. During the transmission repetitive period where the first echo $\gamma_1(t)$ is received, the reference signal generator portion 15 generates a first reference signal $u'_{1s}(t)$ and a second reference signal $u'_{1c}(t)$, which are to be multiplied by the first echo $\gamma_1(t)$. These reference signals are given by the following equations (9.a) and (9.b)

$$u'_{1s}(t)=\sin((\omega_1+\Delta\Omega_1)t+\psi_1) \qquad (9.a)$$

$$u'_{1c}(t)=\cos((\omega_1+\Delta\Omega_1)t+\psi_1) \qquad (9.b)$$

where $\Delta\Omega_1$ is a fixed angular frequency. These reference signals $u'_{1s}(t)$ and $u'_{1c}(t)$ will be referred to as third and reference signals of the first echo signal.

When the reference signals $u'_{1s}(t)$ and $u'_{1c}(t)$ are mixed with the first echo signal in the mixer portions 14A and 14B, the frequency component near the angular frequency $\Delta\Omega_1$ and the frequency component near the angular frequency $(2\omega_2+\Delta\Omega_1)$ are produced. Of these frequency components, the frequency component near the angular frequency $\Delta\Omega_1$ is extracted by the filter portions 12A and 12B. Accordingly, the frequency band of each of the band-pass filter portions 12A and 12B is set to the frequency region near the angular frequency $\Delta\Omega_1$. The frequency components near the DC component and the angular frequency $(2\omega_2+\Delta\Omega_1)$ are blocked by the filter portions.

The output signals $g'_1(t)$ and $h'_1(t)$ of the filter portions 12A and 12B are given by the following equations (10.a) and (10.b) within the range of $\tau \leq t \leq \tau+T_{01}$ $$g'_1(t)=[A(\omega_1)/2]\cos(\Delta\Omega_1 t+\phi_1-2L\omega_1/V-\psi_1) \qquad (10.a)$$

$$h'_1(t)=[A(\omega_1)/2]\sin(\Delta\Omega_1 t+\phi_1-2L\omega_1/V-\psi_1) \qquad (10.b)$$

Within the ranges of $0 \leq t < \tau$, and $t > \tau+T_{01}$, the output signals $g'_1(t)$ and $h'_1(t)$ are zero (0), viz., $g'_1(t)=h'_1(t)=0$ ($0 \leq t < \tau$, and $t > \tau+T_{01}$).

These output signals $g'_1(t)$ and $h'_1(t)$ are converted into digital signals by the A/D convertors 13A and 13B, which are in turn transmitted to the signal processor portion 11.

In the signal processor portion 11, the following signal processing procedure is carried out through the digital computing operation. The signal processor portion 11 generates a signal (expressed by $x_1(t)$ given by the following equation (11) while assuming that $g'_1(t)$ is a real part and $h'_1(t)$ is an imaginary part.

$$x_1(t) = g'_1(t) + jh'_1(t) \quad (11)$$

where j is an imaginary number equal to the number obtained by rasing (−1) to the ½th power.
In the range of $\tau \leq t \leq \tau + T_{01}$, $x_1(t)$ is given by the following equation (12)

$$x_1(t) = [A(\omega_1)/2]\exp(j(\Delta\Omega_1 t + \phi_1 - 2L\omega_1/V - \psi_1)) \quad (12)$$

Within the ranges of $0 \leq t < \tau$, and $t > \tau + T_{01}$, $x_1(t) = 0$.
Further, the signal processor portion 11 generates a reference signal $y_1(t)$ given by the following equation (13)

$$y_1(t) = \exp(-j(\Delta\Omega_1 t + \delta_1)) \quad (13)$$

where $\delta_1$ is a fixed phase. If $\delta_1 = 0$, generality will be kept in the description. Hence, description will be given on the assumption that $\delta_1 = 0$. The reference signal $y_1(t)$ will be referred to as a fifth reference signal of the first echo signal.

Then, $x_1(t)$ is multiplied by $y_1(t)$. The result of the multiplication is an imaginary number. A phase term and an amplitude term corresponding to the envelope are extracted from the multiplication result. As a result, the envelope in the first embodiment and a phase $\theta_1$ corresponding to the equation (7) are obtained for the first echo signal.

The second transmission signal $S_2$ at the angular frequency $\omega_1$ is transmitted to the probe. During the transmission repetitive period where the second echo $\gamma_2(t)$ corresponding to the transmission signal is received, the reference signal generator portion 15 generates the first and the second reference signal $u_{2s}(t)$ and $u_{2c}(t)$ of the second echo signal, which are to be multiplied by the second echo $\gamma_2(t)$ and expressed by the equations (9.a) and (9.b) in which $\omega_1$ is replaced by $\omega_2$, $\Delta\Omega_1$ by $\Delta\Omega_2$, and $\psi_1$ by $\psi_2$. The reference signals $u_{2s}(t)$ and $u_{2c}(t)$ will be referred to as third and fourth reference signals of the second echo signal. The second echo signal is mixed with the third and the fourth reference signals in the mixer portions 14A and 14B. $\Delta\Omega_2$ may be equal to $\Delta\Omega_1$.

The frequency band of each of the band-pass filter portions 12A and 12B is set to the frequency region near the angular frequency $\Delta\Omega_2$. The frequency components near the DC component and the angular frequency $(2\omega_2 + \Delta\Omega_1)$ are blocked by the filter portions. The output signals $g'_2(t)$ and $h'_2(t)$ of the filter portions 12A and 12B are given by the equations (10.a) and (10.b) in which $\omega_1$ is replaced by $\omega_2$, $\Delta\Omega_1$, by $\Delta\Omega_2$, $\psi_1$ by $\Omega_2$, and $\phi_1$ by $\phi_2$, within the range of $\tau \leq t \leq \tau + T_{02}$. Within the ranges of $0 \leq t < \tau$, and $t > \tau + T_{02}$, $g'_2(t) = h'_2(t) = 0$.

The output signals $g'_2(t)$ and $h'_2(t)$ are converted into digital signals by the A/D convertors 13A and 13B, and the digital signals are transmitted to the signal processor portion 11.

The signal processor portion 11 generates a signal (expressed by $x_2(t)$, while assuming that $g'_2(t)$ is a real part and $h'_2(t)$ is an imaginary part, and a reference signal (expressed by $y_2(t)$). The reference signal $y_2(t)$ will be referred to as a fifth reference signal of the second echo signal.

$x_2(t)$ is given by the equation (11) in which $g'_1(t)$ is replaced by $g'_2(t)$, and $h'_1(t)$ by $h'_2(t)$. $y_2(t)$ and $x_2(t)$ within the range of $\tau \leq t \leq \tau + T_{02}$ are expressed by the equations (13) and (12) in which $\omega_1$ is replaced by $\omega_2$, $\Delta\Omega_1$, by $\Delta\Omega_2$, $\psi_1$ by $\psi_2$, $\phi_1$ by $\phi_2$, and $\delta_1$ by $\delta_2$.
$\delta_2 = 1$, as in the case of $\delta_1$.
Within the ranges of $0 \leq t < \tau$, and $t > \tau + T_{02}$, $x_2(t) = 0$.

In the signal processor portion 11, for the second echo, the envelope in the first embodiment and a phase $\theta_2$ corresponding to the equation (8) are obtained by the complex multiplication of $x_2(t)$ and $y_2(t)$ as in the previous case.

In this way, the phases $\theta_1$ and $\theta_2$, and the envelope for the first and the second echo signal have been obtained. Now, an intended distance is obtained by the signal processing procedure as of the first embodiment, on the basis of those results.

The useful effects of the fourth embodiment and the operation thereof causing the effects will be described. In the present embodiment, the angular frequency of the third and fourth reference signals of the first echo is shifted from the angular frequency of the first echo by $\Delta\Omega_1$, the frequency of the third and the fourth reference signal of the second echo is also shifted from the angular frequency of the second echo by $\Delta\Omega_2$. The frequency components near the angular frequencies $\Delta\Omega_1$ and $\Delta\Omega_2$ are extracted by the filter portions 12A and 12B. Therefore, drift of the amplifiers contained in the transmitter portion 9 and the receiver portion 10, drift of the circuit elements contained in the mixer portions 14A and 14B, and the unnecessary low frequency components including the DC component superposed on the receiving signal by leakage thereof from the transmitter portion 9 to the receiver portion 10, can be filtered out by the filter portions 12A and 12B. Therefore, there is eliminated an adverse effect of the unnecessary frequency components upon the measuring results.

5th Embodiment

The fifth embodiment of the present invention will be described. The arrangement of an ultrasonic distance measuring device according to the third embodiment, which is substantially the same as that described referring to FIG. 7 in the third embodiment, will first be described, and then the arrangement of an ultrasonic distance measuring device, which is substantially the same as that described referring to FIG. 6 in the second embodiment, will then be described.

In the present embodiment, a distance from the probe to an object is measured using the information of a phase and an amplitude of an echo or a phase and an envelope of an echo. Accordingly, if the measurement of the information suffers from an error, the resultant distance also contains an error.

In the fifth embodiment, in the device arrangement shown in FIG. 9 or 10, the frequency response characteristics of all of the components, portions, and parts, which form the device, such as the probe 6, transmitter portion 9, receiver portion 10, filter portions 12A and 12B, mixer portions 14A and 14B, A/D convertor portion 13, 13A and 13B, connectors, cables, and the like, are measured in advance. After correction of the phases and the amplitudes in those frequency response characteristics of those components, portions and parts on the basis of the results of the measurements, the information of the phase and the amplitude or the phase and the envelope, which are used for the distance measurement, are obtained.

The case of the arrangement described in FIG. 7 will be described in detail. The frequency response characteristics of the components, portions, and parts making up the ultrasonic distance measuring device, for the frequency to be used, are individually measured.

A method of correcting the fixed phase delay by the components, portions, and parts on the basis of the measuring results will be described. The fixed phase delays by the components, portions, and parts are obtained using the results of measuring the frequency response characteristics. The total fixed-phase delay is obtained by adding the fixed phase delays in the direction of a signal flow.

The word "signal flow direction" means the direction in which a signal flows from the transmitter portion 9 to the probe 6, and from the probe 6 to the signal processor portion 11 by way of a route of the first output terminal of the receiver portion 10, mixer portion 14A, filter portion 12A, and the A/D convertor portion 13A. This signal path will be called a first signal path.

It is noted that two signals, i.e., an outgoing signal for transmission and an incoming signal for reception pass through the probe 6 in the process of obtaining the total fixed-phase delay. The phase delay takes place in both the outgoing signal and the incoming signal. Because of this, in the process of adding together the fixed phase delays, the fixed-phase delays of the outgoing signal and the incoming signal must be added together.

In the arrangement of the ultrasonic distance measuring device, there is another signal flow or path. In this signal path, a signal flows from the transmitter portion 9 to the probe 6, and from the probe 6 to the signal processor portion 11 by way of a route of the second output terminal of the receiver portion 10, mixer portion 14B, filter portion 12B, and the A/D convertor portion 13B. This signal path will be called a second signal path.

The total fixed-phase delay as the sum of the fixed-phase delays by the respective components, portions, and parts when the first transmission signal of the angular frequency flows through the first signal path, is denoted as $\Delta\theta_{11}$. The total fixed-phase delay as the sum of the fixed-phase delays by the respective components, portions, and parts when it flows through the second signal path, is denoted as $\Delta\theta_{12}$.

At this time, the reference signal generator portion 15 generates the first reference signal of the first echo of which the fixed-phase $\psi_1$ is delayed $\Delta\theta_{11}$. In other words, the first reference signal of which the fixed phase is $(\psi_1-\Delta\theta_{11})$ is generated. Similarly, the fixed phase $\psi_1$ of the second reference signal of the first echo generated is delayed $\Delta\theta_{12}$. As a result, the total fixed-phase delays of the signal along the first and the second signal path cancel out before the signal reaches the signal processor portion 11.

Similarly, the total fixed-phase delay as the sum of the fixed-phase delays by the respective components, portions, and parts when the second transmission signal of the angular frequency flows through the first signal path, is denoted as $\Delta\theta_{21}$. The total fixed-phase delay as the sum of the fixed-phase delays by the respective components, portions, and parts when it flows through the second signal path, is denoted as $\Delta\theta_{22}$. The fixed phase $\psi_2$ of the first and the second reference signal of the first echo, generated by the reference signal generator portion 15, is delayed $\Delta\theta_{21}$ and $\Delta\theta_{22}$. As a result, the total fixed-phase delays of the signal along the first and the second signal path cancel out before the signal reaches the signal processor portion 11.

The total fixed-phase delays of the signal by the respective components, portions, and parts are corrected in this way before the signal reaches the signal processor portion 11.

The amplitude characteristics in the frequency response characteristics of the respective components, portions, and parts, which form the ultrasonic distance measuring device, are corrected in the following manner. An overall amplitude characteristic, which results from contemplating overall the amplitude characteristics of the respective components, portions, and parts of the device at the carrier frequency of the first transmission signal when the signal flows through the first signal path, is denoted as $A_{11}$. The overall amplitude characteristic along the second signal path is denoted as $A_{12}$.

The overall amplitude characteristics at the carrier frequency of the second transmission signal when the signal flows through the first and second signal path, are denoted as $A_{21}$ and $A_{22}$, respectively.

If there is no difference among the overall amplitude characteristics $A_{11}$, $A_{12}$, $A_{21}$ and $A_{22}$, no problem arises. However, problem arises if there is a difference among those characteristics. Then, this will be described using a case where the overall amplitude characteristic $A_{11}$ is 1.

The amplitudes of the reference signals of the first and the second echo, generated by the reference signal generator portion 15, are as follows: the amplitude of the first reference signal of the first echo is "1", and the amplitude of the second reference signal of the first echo and the first and the second reference signal of the second echo are $1/A_{12}$, $1/A_{21}$, and $1/A_{22}$, respectively. Thus, the overall amplitude characteristics of the frequency response characteristics of the respective components, portions, and parts of the device are corrected before the signal reaches the signal processor portion 11.

Description of the fifth embodiment of the present invention has been made using the third embodiment. A case where the fifth embodiment is applied to the fourth embodiment will be described. In this case, the amplitudes and the phases of the third and the fourth reference signal of the first echo are set in the procedure of setting the amplitudes and the phases of the first and the second reference signal of the first echo. Similarly, the amplitudes and the phases of the third and the fourth reference signal of the second echo are set in the procedure of setting the amplitudes and the phases of the first and the second reference signal of the second echo. With the setting of the amplitudes and the phases of the reference signals, the total fixed-phase delay and the overall amplitude characteristic (referred to as an overall frequency response characteristic) of the respective components, portions, and parts of the device are corrected before the signal reaches the signal processor portion 11.

The case where the fifth embodiment is applied to the arrangement of FIG. 9 will be described. The case of the arrangement of FIG. 10 in which two signal paths are present between the receiver portion 10 and the signal processor portion 11 is described above. In the case of FIG. 9 to be described hereinafter, one signal path is present between the receiver portion 10 and the signal processor portion 11. When the fifth embodiment is applied to the FIG. 9 case, it is modified in the following way.

As shown, the arrangement of FIG. 9 contains one signal flow path. The signal path ranges from the transmitter portion 9 to the probe 6, and from the probe 6 to the signal processor portion 11 by way of the route of the receiver portion 10, filter portion 12, and the A/D convertor portion 13.

The frequency response characteristics of the respective components, portions, and parts of the device are first measured. The fixed-phase delays by the respective components, portions, and parts of the device are measured at the carrier frequency of the first and the second transmission signal when the signals flow through the signal path, and those are summed. The total fixed-phase delays as the result of the additions are denoted as $\Delta\theta_1$ and $\Delta\theta_2$, respectively. The fixed phase $\psi_1$ of the first and the second reference signal of the first echo, generated by the signal processor portion 11, is delayed by $\Delta\theta_1$. Similarly, the fixed phase $\psi_1$ of the first and the second reference signal of the second echo is delayed by $\Delta\theta_2$. With this, the total fixed-phase delays by the respective components, portions, and parts of the device are corrected.

For the correction of the amplitude in the frequency response characteristics of the respective components, portions, and parts of the device, the overall amplitude characteristics, which results from contemplating overall the amplitude characteristics of the respective components, portions, and parts of the device at the carrier frequencies of the first and the second transmission signal when the signals flow through the signal path, are obtained. The resultant overall amplitude characteristics are denoted as $A_1$ and $A_2$, respectively. It is assumed that the overall amplitude characteristic $A_1$ is "1" for easy of explanation. The first and the second reference signal of the first echo, which have the amplitude of "1", and the first and the second reference signal of the second echo, which have the amplitude of $1/A_2$, are generated by the signal processor portion 11. As a result, the overall amplitude characteristics of the frequency response characteristics of the respective components, portions, and parts of the device are corrected.

The procedure of the second embodiment, not the process where the phases and the amplitudes of the reference signals are set as mentioned above, may be used for the correction of the overall amplitude characteristics for the case based on one signal path. In this case, the phases and the envelopes of the first and the second echo or the phases and the amplitudes thereof are obtained. $\Delta\theta_1$ is added to the obtained phase $\Delta\theta_1$, and $\Delta\theta_2$ is added to the obtained phase $\Delta\theta_2$. The amplitude of the second echo or the amplitude of the envelope is multiplied by $1/A_2$.

The above-mentioned correction method is based on the results of individually measuring the frequency response characteristics of the respective components, portions, and parts of the device. In the case based on one signal path, the following correction method may be used.

The phases and the envelopes or the phases and the amplitudes of the first and the second echo are obtained in the procedure of the second embodiment. In this case, a reference reflecting surface is used in place of an object 8. A distance between the probe 6 and the reference reflecting surface is already known. Since the distance to the reference reflecting surface is known, the phase term corresponding to the distance can be calculated. The phase term is subtracted from the obtained phase in the procedure of the second embodiment. The phase obtained by removing the fixed phases of the transmission signal and the reference signal from the phase resulting from the subtraction is the total fixed-phase delay of the respective components, portions, and parts of the device.

Only for the first echo, since L is already known, $\Delta\theta_1$ is obtained using the equating $$\theta_1 = -2L\omega_1/V - \Delta\theta_1 + \phi_1 - \psi_1 + 2n\pi$$

$\Delta\theta_1$ indicates the total fixed-phase delay of the respective components, portions, and parts of the device along the signal path.

Also for the second echo, the total fixed-phase delay $\Delta\theta_2$ can be calculated by using the related equation which corresponds to the above equation where the suffix "1" is replaced by "2", and n is replaced by m.

For the overall amplitude characteristics of the respective components, portions, and parts of the device, $A_1/A_2$ is obtained by calculating the ratio of the amplitudes of the first and the second echo or the ratio of the amplitudes of the envelopes thereof. Accordingly, the value of $A_2$ is obtained when $A_1$ is 1.

Thus, the overall frequency response characteristics of the respective components, portions, and parts of the device are obtained in the above-mentioned procedure. Then, the correction can be made on the basis of these results in the signal processor portion 11 as in the case of the above-mentioned correction.

As described above, in the fifth embodiment, the amplitudes and the phases of the first and the second reference signal of the first echo, which are generated by the reference signal generator portion 15, and the amplitudes and the phases of the first and the second reference signal of the second echo are set on the basis of the measurement results of the overall frequency response characteristics of the respective components, portions, and parts of the device. The difference between the overall amplitude characteristics in the overall frequency characteristics of the respective components, portions, and parts of the device, and the signal corrected in the total fixed-phase delay are transmitted to the signal processor portion 11. As a result, the accuracy of the distance measurement is improved.

The amplitudes and the phases of the third and the fourth reference signal of the first echo, which are generated by the reference signal generator portion 15, and the amplitudes and the phases of the third and the fourth reference signal of the second echo are set on the basis of the measurement results of the overall frequency response characteristics of the respective components, portions, and parts of the device. The difference between the overall amplitude characteristics in the overall frequency characteristics of the respective components, portions, and parts of the device, and the signal corrected in the total fixed-phase delay are transmitted to the signal processor portion 11. As a result, similar useful effects are achieved.

In the case based on one signal path, the amplitudes and the phases of the first and the second reference signal of the first echo, which are generated by the reference signal generator portion 15, and the amplitudes and the phases of the first and the second reference signal of the second echo are set on the basis of the measurement results of the overall frequency response characteristics of the respective components, portions, and parts of the device. The difference between the overall amplitude characteristics in the overall frequency characteristics of the respective components, portions, and parts of the device, and the signal corrected in the total fixed-phase delay are transmitted to the signal processor portion 11. As a result, similar useful effects are achieved.

Also in the case based on one signal path, in the signal processor portion 11, the phases and the envelopes or the phases and the amplitudes of the first and the second echo are obtained in the same procedure of the second embodiment. Thereafter, for the obtained phases, the total fixed-phase delays in the overall frequency response characteristics of the respective components, portions, and parts of the device are corrected, and for the obtained amplitudes or the envelopes, the overall amplitude characteristics of the respective components, portions, and parts of the device are corrected. The result is the achievement of similar useful effects.

The phases and the envelopes or the phases and the amplitudes of the first and the second echo are obtained in the procedure of the second embodiment, using the reference reflecting surface, which is separated from the object 8 an already known distance. The phase component corresponding to the distance and the fixed phase components of the transmission signal and the reference signal are subtracted from the obtained phase. The total fixed-phase delay of the respective components, portions, and parts of the device is obtained from the remaining phase. The overall amplitude characteristic of the respective components, portions, and parts of the device is obtained from the amplitude of the echo or the amplitude of the envelope thereof. The correction is carried out using the total phase delay and the overall amplitude characteristic in the signal processor portion 11. Accordingly, similar useful effects are achieved.

Let us compare the correction method using the reference reflecting surface with the correction method based on the results of individually measuring the characteristics of the respective components, portions, and parts of the device. In the latter method, when the characteristic measurements contain errors, the errors are accumulated, so that the resultant correction value is deviated from the true one. The former method is free from such measurement errors, thereby securing a high accuracy of the measurement.

6th Embodiment

The 6th embodiment of the present invention will be described with reference to FIGS. 11, 12, and 13. The arrangement of the ultrasonic distance measuring device according to the 6th embodiment of the present invention is the same as that of the first embodiment. FIGS. 8(a) and 8(b) are waveforms of transmission signals, FIG. 9 is a characteristic diagram showing the frequency response characteristic of the probe 6, and FIGS. 13(a) to 13(d) are waveform diagrams showing echoes.

Figure 11A:
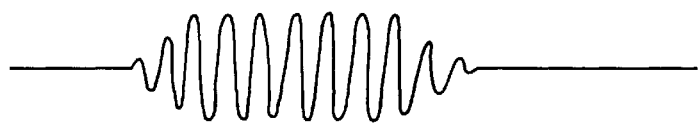
FIGS. 11(a) and 11(b) show waveform diagrams for explaining the operation of an ultrasonic distance measuring device according to a sixth embodiment of the present invention.
Figure 11B:
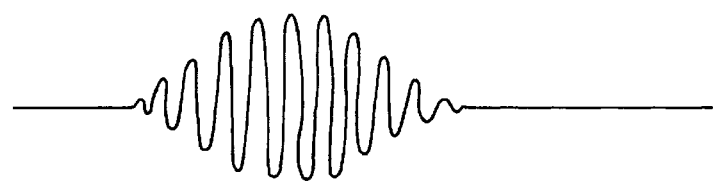

The operation of the 6th embodiment of the present invention will be described. In the first embodiment, the envelope of a transmission signal has a rectangular waveform as described by the equation (1). On the other hand, in the sixth embodiment, a first transmission signal of the carrier frequency f1 and a second transmission signal of the carrier frequency f2, which are generated by the transmitter portion 9, have the following envelope waveforms. The envelope of the first transmission signal gently varies in the rising and the falling part thereof, as shown in FIGS. 11(a) and 11(b). The signal processing procedures for the first and the second echo are the same as those of the first embodiment.

Figure 12:
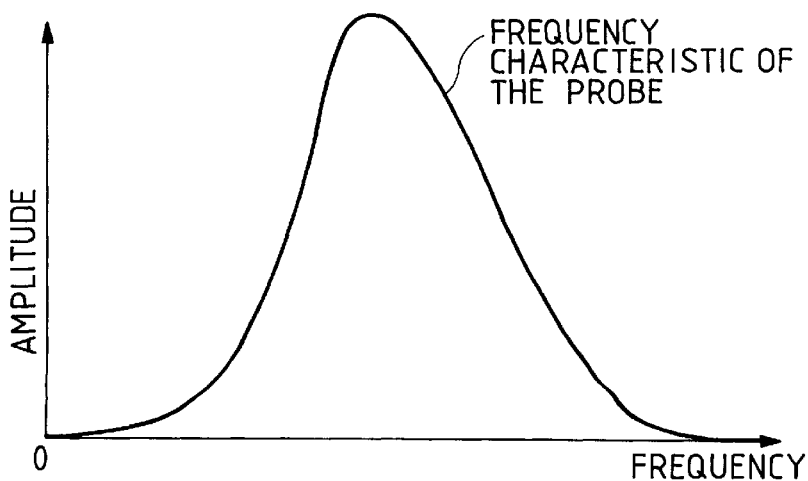
FIG. 12 shows a characteristic diagram for explaining the operation of an ultrasonic distance measuring device according to the sixth embodiment.
Figure 13A:
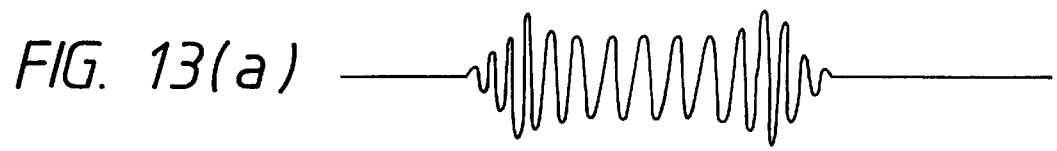
FIGS. 13(a) to 13(d) show another waveform diagrams for explaining the operation of an ultrasonic distance measuring device according to the sixth embodiment.
Figure 13B:
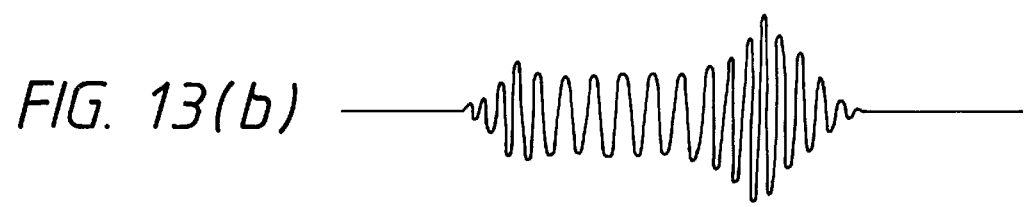
Figure 13C:
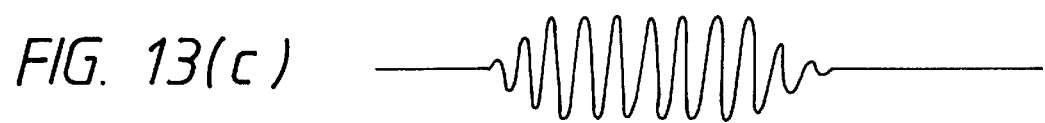
Figure 13D:
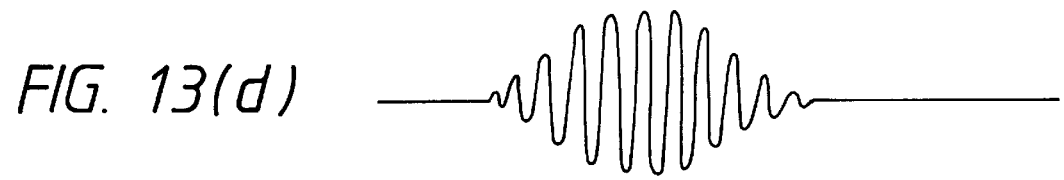

As shown in FIG. 12, the frequency band width of the probe 6 is finite. When the transmission signal of which the envelope waveform is rectangular is used, the envelope waveform of the echo is not rectangular as shown in FIGS. 13(a) and 13(b). The envelope greatly varies particularly in the rising and the falling part thereof. Further, the frequency is shifted from the carrier frequency of the transmission signal in the rising and the falling parts thereof. Therefore, a phase, which is obtained from the rising part or the falling part cut out of the envelope waveform in the procedure of the first embodiment, is different from a phase obtained from the middle part cut out of the envelope waveform in a similar procedure. The middle part of the envelope waveform is configured substantially flat, and the value of the obtained phase is approximate to a true value.

For this reason, it is necessary to additionally use a procedure to detect the phase from the middle part of the envelope waveform, not from the rising and the falling part thereof. When the transmission signals of the waveforms as shown in FIGS. 11(a) and 11(b) are used, the adverse effect by the finite band width of the probe 6 is reduced since the frequency bands of those transmission signals are narrow when compared with the transmission signals of which the envelope waveforms are rectangular. Further, the waveforms of the echoes corresponding to the transmission signals gently vary in the rising and the falling part thereof, and resemble the waveforms of the transmission signals. The frequencies of the echoes in the rising and the falling part are substantially equal to the carrier frequency. The difference between the phase obtained from the rising part or the falling part cut out of the envelope waveform and the phase from the middle part similarly cut out thereof is much smaller than that in the above-mentioned case. In other words, the phases of those parts of the envelope waveform are substantially equal to one another. Therefore, there is no need of the procedure to cut the middle part out of the envelope waveform.

As described above, the sixth embodiment uses the first and the second transmission signal of which the envelopes vary gently in the rising and the falling part, so that there is no need of the procedure to cut the middle part out of the waveform of each of the first and the second echo. This advantage is very useful in the measurement under the condition of a narrow frequency band or where only the probe of a narrow band width is available.

7th Embodiment

Figure 14:
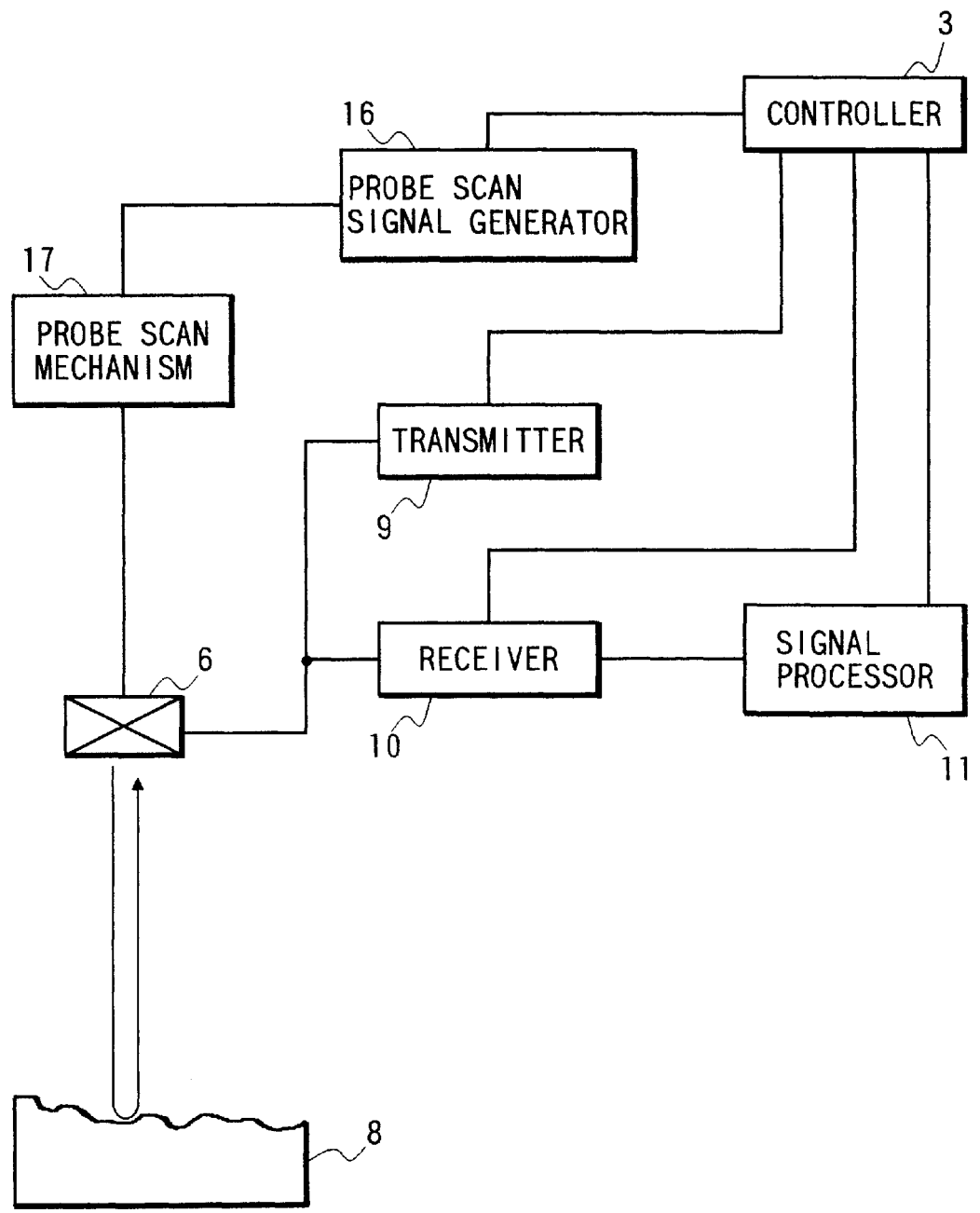
FIG. 14 shows a block diagram showing the arrangement of an ultrasonic distance measuring device according to a seventh embodiment of the present invention.

The seventh embodiment of the present invention will be described with reference to FIG. 14. FIG. 14 shows in block form the arrangement of an ultrasonic distance measuring device according to the present invention. In the figure, reference numeral 16 designates a probe scan signal generator; and 17, a probe scan mechanism. The probe scan signal generator 16 is connected to a controller portion 3 and the probe scan mechanism 17. The probe scan mechanism 17 is a mechanism for mechanically driving the probe 6 for scan. The remaining arrangement of the ultrasonic distance measuring device is the same as the corresponding one of the first embodiment.

The operation of the seventh embodiment will be described. In this embodiment, in response to a signal from the controller portion 3, the probe scan signal generator 16 generates a probe scan signal for transmission to the probe scan mechanism 17. The probe scan mechanism 17 spatially moves the probe 6 for scan. To be more specific, after a distance measurement is carried out at a point in a space in the procedure of the first embodiment by using the probe is completed, the probe is moved to another point and another distance measurement is carried out in a similar procedure. This process is repeated over a desired spatial area. In this way, the object is scanned with the probe 6 thus moved.

The ultrasonic distance measuring device thus arranged is capable of measuring a shape of an object 8. The direction of the scanning movement by the probe 6 is not limited to the direction of the movement of the probe 6 along the surface of the object 8. The movement of the probe 6 may take any direction, which depends on a shape of the object 8.

The scanning movement of the probe 6 means a mechanical or geometrical movement of the probe relative to the object 8. As a matter of course, the mechanical or geometrical movement of the probe may be replaced by an electrical or signal processing scan, which uses a plural number of probes 6. In this case, the scan is based on the array and the scan, which are similar to those of the phased array radar and the phased array antenna.

In the instance of the embodiment, the probe 6 is moved for scan. If required, the probe 6 is fixed, while the object 8 is movable. In this case, an object scan signal generator and an object scan mechanism, which correspond respectively to the probe scan signal generator 16 and the probe scan mechanism 17, are set on the object 8.

In the seventh embodiment, a probe of the type in which ultrasonic beams are condensed may be used for the probe 6. When such a probe is used, the bearing resolution is improved.

8th Embodiment

Figure 15:
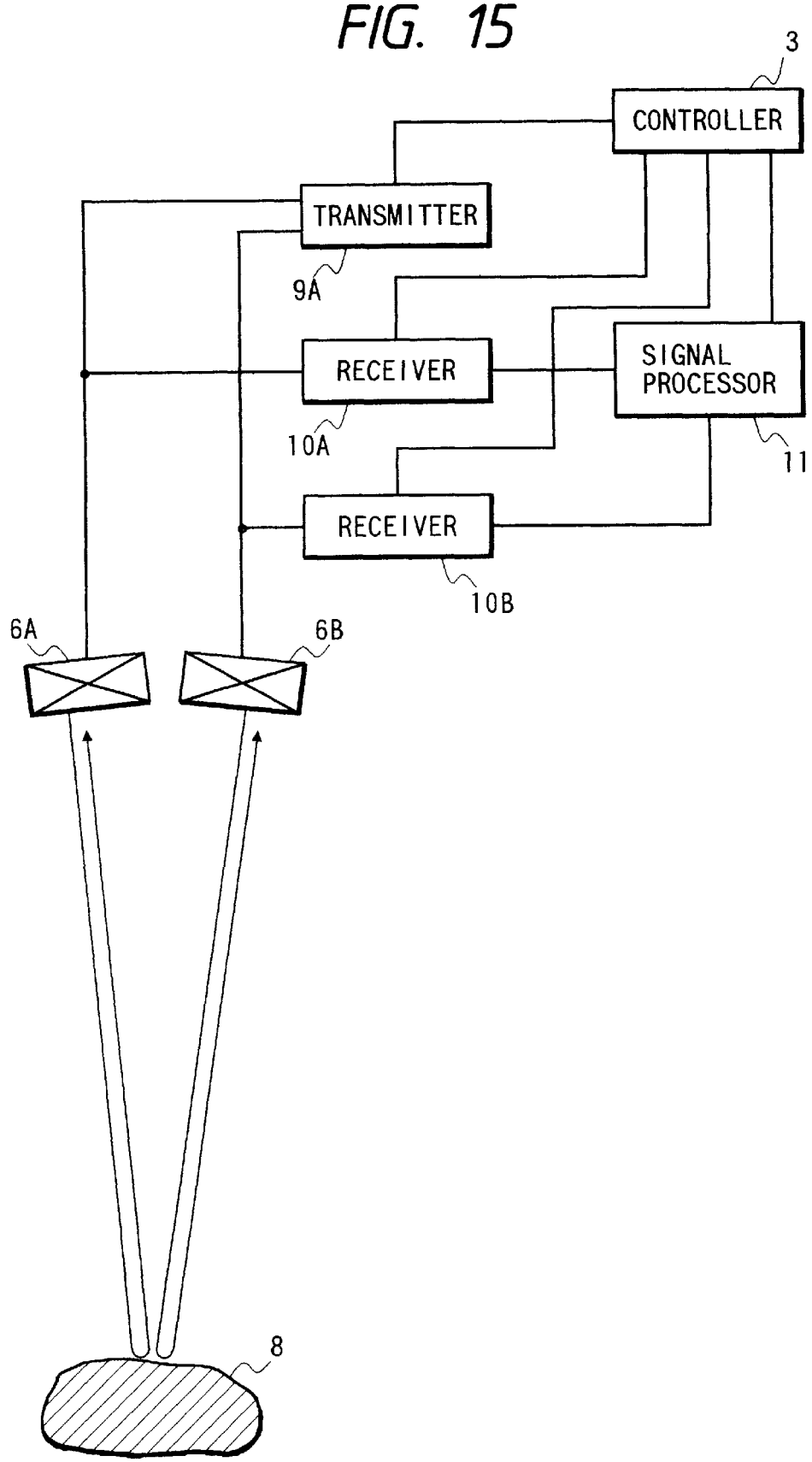
FIG. 15 shows a block diagram showing the arrangement of an ultrasonic distance measuring device according to an eighth embodiment of the present invention.
Figure 16A:
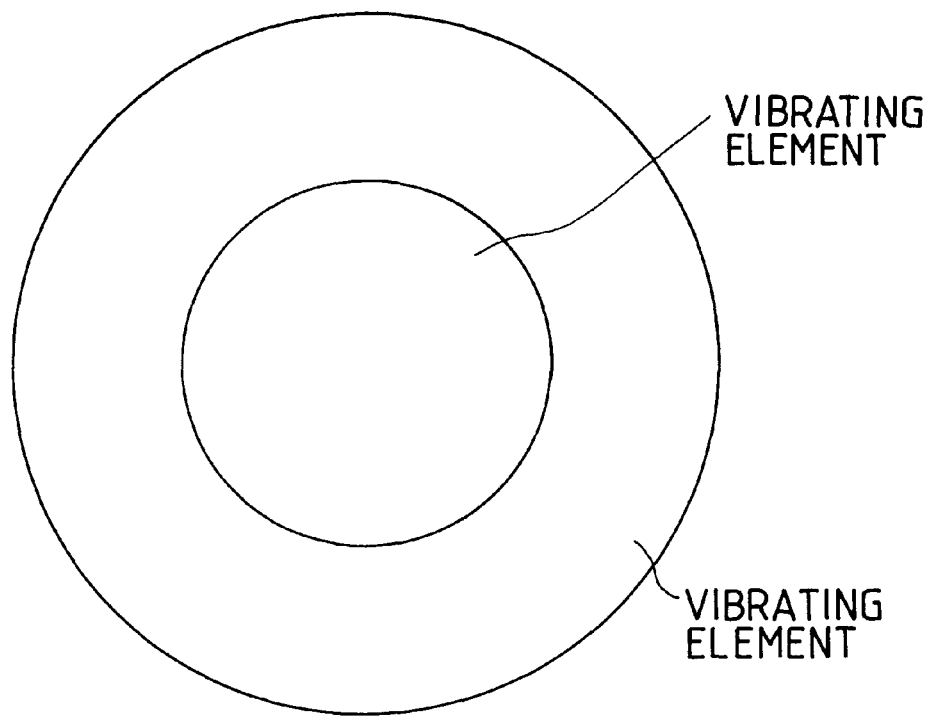
FIGS. 16(a) and 16(b) show diagrams showing the construction of the eighth embodiment of the present invention.
Figure 16B:
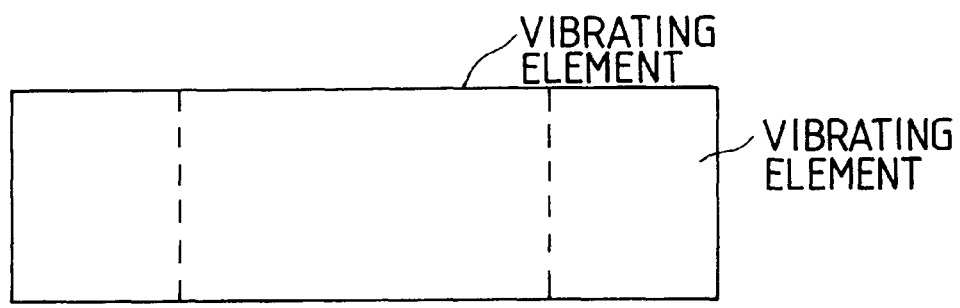

The eighth embodiment of the present invention will be described with reference to FIGS. 15 and 16. FIG. 15 illustrates in block form the arrangement of an ultrasonic distance measuring device according to the eighth embodiment of the present invention. FIG. 16 is a diagram showing the construction of a probe 6.

As shown in FIG. 15, the ultrasonic distance measuring device is provided with two separate probes 6A and 6B. Two separate receives 10A and 10B are used in the device. A transmitter portion 9 has two output terminals, i.e., first and second output terminals. The first and the second output terminal of the transmitter portion 9 are connected to the probes 6A and 6B, respectively. The probes 6A and 6B are connected to the input terminals of receiver portions 10A and 10B, respectively. The output terminals of the receiver portions 10A and 10B are connected to a signal processor portion 11. A controller portion 3 is connected to both the receiver portions 10A and 10B.

The operation of the eighth embodiment will be described. In this embodiment, the transmitter portion 9 produces a first transmission signal at the transmission repetitive period Tτ, and sends it to the probe 6A through the first output terminal thereof. The transmitter portion 9 also produces a second transmission signal at the transmission repetitive period Tτ, and sends it to the probe 6B through the second output terminal thereof. The first and the second transmission signal are generated at the same time point.

In response to the first and the second transmission signal, the probes 6A and 6B emit ultrasonic pulses corresponding to these transmission signals at the same time. The ultrasonic pulses emitted toward an object are reflected by the object, and the reflected ultrasonic pulses as first and second echoes are received by the probes 6A and 6B. The first and the second echo, received by the probes, are transferred to the receiver portions 10A and 10B, respectively. In the receiver portions 10A and 10B, these echo signals are amplified and transferred to the signal processor portion 11. Where the difference between the propagating paths of the two ultrasonic pulses, which correspond to the first and the second transmission signal, is negligible, the first nd the second echo signal are processed in the signal processor portion 11 as in the first embodiment, so that a distance from the probe 6A or 6B to the object 8 is computed in the same procedure as of the first embodiment.

The eighth embodiment measures a desired distance during one transmission repetitive period Tτ. Therefore, the distance measuring time is the half of that of the first embodiment.

In the instance of the eighth embodiment, the receiving period (time interval) of the first echo is equal to that of the second echo. The receiving periods of the first and the second echo may be different from each other if a ratio of these periods has a predetermined value or a predetermined relationship is present between them. In this case, the signal processing subsequent to the reception of the first and the second echo is properly carried out in the signal processor portion 11, while the predetermined ratio or relationship is taken into consideration.

To be more specific, the receiver portions 10A and 10B are followed by frequency dividers, respectively. A frequency dividing ratio of the frequency divider in association with the receiver portion 10A and the frequency divider in association with the receiver portion 10B is determined on the basis of a distance $L_A$ from the receiver portion 10A and a distance $L_B$ from the receiver portion 10B. The output signals of the frequency dividers are inputted to the signal processor portion 11. The signal processor portion 11 processes the output signals on the basis of the frequency dividing ratio.

The control may be carried out at the stage of reception or subsequent to the reception as just mentioned, while the control is carried out in the stage of transmission in the description of the eighth embodiment.

In the device of FIG. 15, two probes 6A and 6B are separately used. A single probe 6 constructed as illustrated in FIG. 15 may be used in place of the two separate probes. As shown, a probe 6 is constructed with two vibrating elements, which are coaxially arrayed and operate independently. One of the vibrating element is connected to the first output terminal of the transmitter portion 9 and the receiver portion 10A, while the other is connected to the second output terminal of the transmitter portion 9 and the receiver portion 10B. With this construction, the main beams of ultrasonic waves, emitted from the two vibrating elements, travel in the direction along the center axis of the probe 6. Accordingly, the main beams are directed to a point on the object 8. On the other hand, in the FIG. 15 device, the two probes 6A and 6B must be slanted toward a point on the object 8. Use of the probe thus constructed lessens such a limit on the relative positional relationship of the object 8 and the probe 6 that the difference between the propagating paths of the two ultrasonic pulses, which correspond to the first and the second transmission signal, must be negligible.

If the probe 6 shown in FIG. 16 is used, the probe scan mechanism for moving the probe 6 for scan that is referred to in the seventh embodiment, may be simplified. Where the transmitting and receiving ultrasonic beams of the converging type are formed by using the two vibrating elements curved in shape, an advantage of the improved bearing resolution is additionally created.

In the instance of the eighth embodiment, a single transmitter portion 9 is used and it has the two output terminals. In an alternative, two transmitter portions 9 are used in association with the probes 6A and 6B, respectively. The transmitter portions 9 produce first and second transmission signals at the transmission repetitive periods Tτ independently but synchronously for transmission to the probes 6A and 6B, respectively.

9th Embodiment

Figure 17:
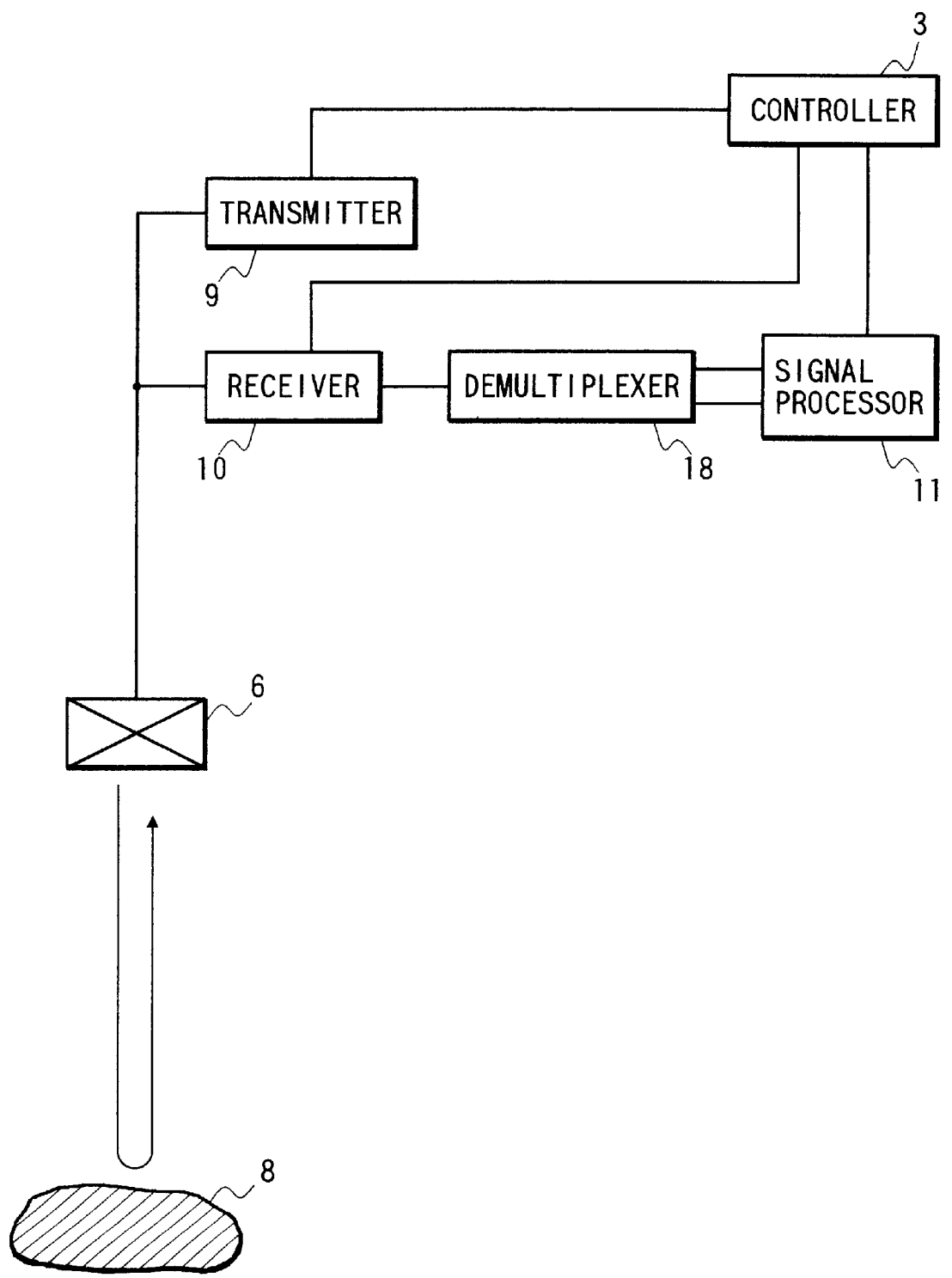
FIG. 17 shows a block diagram showing the arrangement of an ultrasonic distance measuring device according to a ninth embodiment of the present invention.

The sixth embodiment of an ultrasonic distance measuring device according to the present invention will be described with reference to FIG. 17. FIG. 17 is a block diagram showing the arrangement of an ultrasonic distance measuring device according to a ninth embodiment of the present invention. In the figure, reference numeral 18 designates a demultiplexer portion inserted between the receiver portion 10 and the signal processor portion 11. The input terminal of the demultiplexer portion 18 is connected to the output terminal of the receiver portion 10. The demultiplexer portion 18 has two output terminals, i.e., first and second output terminals. The first and the second output terminals of the demultiplexer portion 18 are connected to the signal processor portion 11. The remaining arrangement of the ninth embodiment is substantially the same as that of the first embodiment.

The operation of the ninth embodiment will be described. In the ninth embodiment, the transmitter portion 9 repetitively produces a transmission signal, which is the sum of a first transmission signal $S_1(t)$ of the angular frequency $\omega_1$ and a second transmission signal $S_2$ of the angular frequency $\omega_2$, viz., $S_1(t)+S_2(t)$, at the transmission repetitive periods $T\tau$. The transmission signal $S_1(t)+S_2(t)$ is transmitted to the probe 6. Accordingly, an echo received by the probe is also the sum of a first echo $\gamma_1(t)$ and a second echo $\gamma_2(t)$.

The received signal is amplified and then is demultiplexed into a first echo $\gamma_1(t)$ and a second echo $\gamma_2(t)$ by the demultiplexer portion 18 by making use of the difference of the carrier frequencies of the first and the second echo. The resultant echoes $\gamma_1(t)$ and $\gamma_2(t)$ are transmitted to the signal processor portion 11, independently. The signal processor portion 11 processes these echo signals in the signal processing procedure that is described in the first embodiment, and determines a distance from the probe to the object on the basis of the signal processing results.

The ninth embodiment measures a desired distance during one transmission repetitive period $T\tau$. Therefore, the distance measuring time is the half of that of the first embodiment.

In a modification of the ninth embodiment, the demultiplexer portion 18 demultiplexes the echo received by the probe 6 into a first and a second echo, then these echo signals are applied to two receiver portions 10A and 10B, and applied to the signal processor portion 11.

Where two input signals that are added together are processed by one amplifier, a cross modulation tends to occur. In other words, the nonlinearity of the amplifier and the related circuitry, which are contained in the receiver portion 10, causes the sum and difference of the two different carrier frequencies of the first and the second echo signals, and harmonics. In the modification, the echo signals are processed by the two separate receiver portions 10A and 10B. Therefore, the alternative is free from such unwanted frequency components.

In another modification of the ninth embodiment, two transmitter portions 9 are used. The transmitter portions 9 produce first and second transmission signals independently. A multiplexer for multiplexing the first and the second transmission signal is used. The first and the second transmission signal are transmitted to the multiplexer, and the multiplexed transmission signal is transmitted to the probe 6.

In the second modification using the two transmitter portions 9 and the multiplexer, the amplifiers at the last stage in the transmitter portions 9 are separately provided. Therefore, the second modification is free from the cross modulation, which tends to occur when the two input signals, added together, are amplified by a single amplifier as by the amplifier in the receiving side.

10th Embodiment

Figure 18:
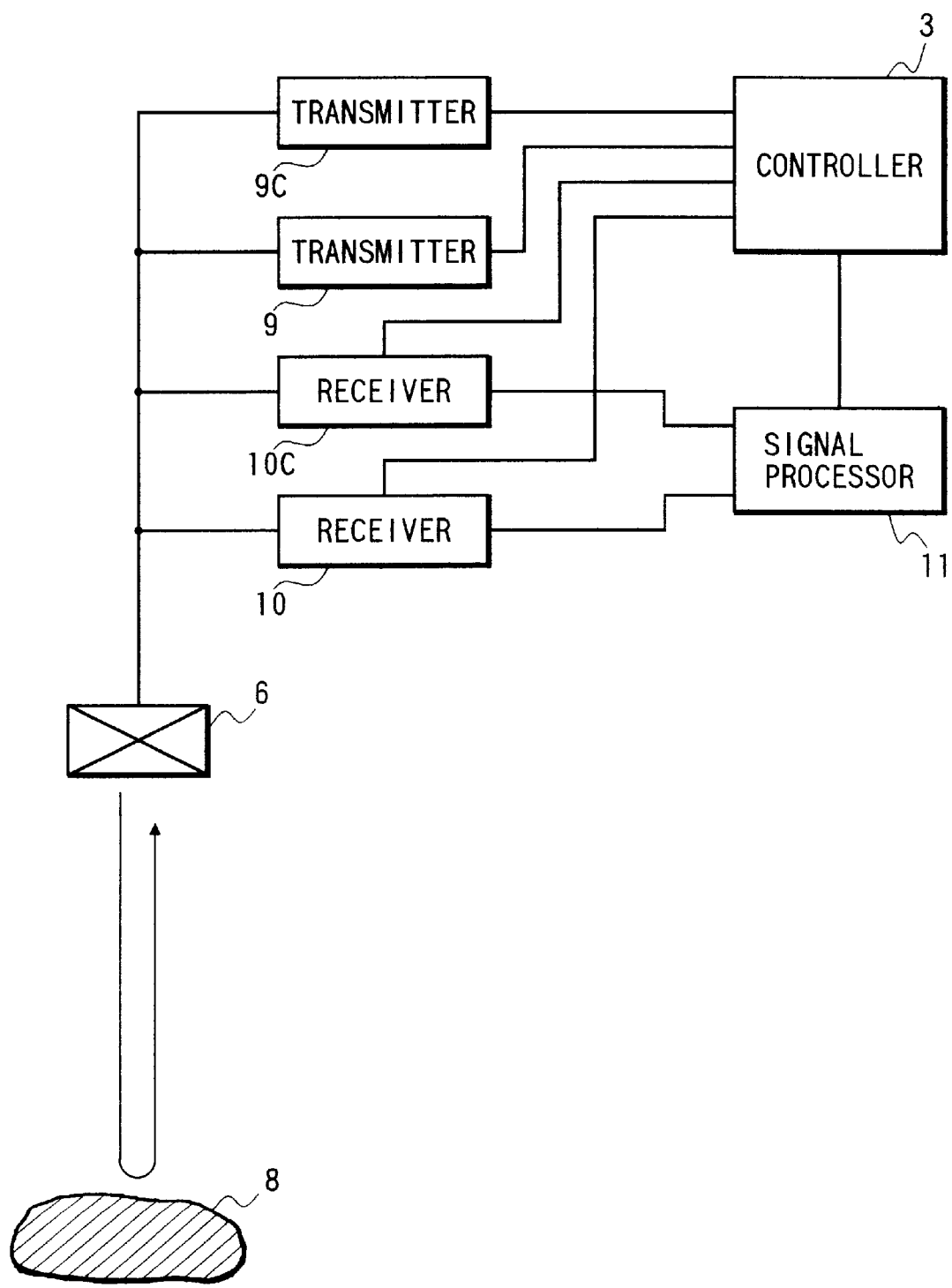
FIG. 18 shows a block diagram showing the arrangement of an ultrasonic distance measuring device according to a tenth embodiment of the present invention.
Figure 19:
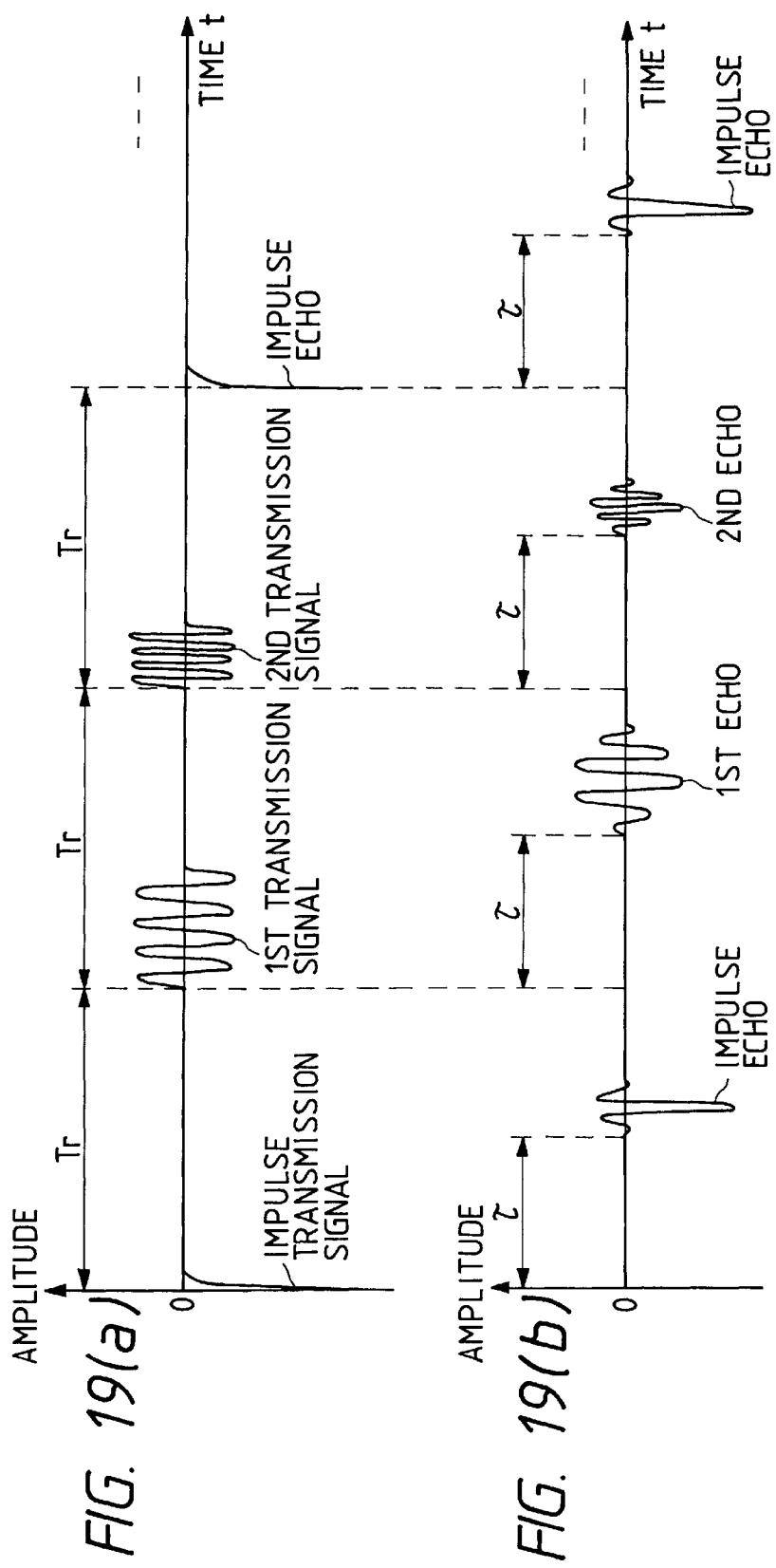
FIGS. 19(a) and 19(b) show waveform diagrams for explaining the operation of an ultrasonic distance measuring device according to the tenth embodiment.

The tenth embodiment of an ultrasonic distance measuring device according to the present invention is characterized in that an impulse echo, not the first and the second echo, is used in the step $S_D$ for determining the candidate-contained portion. The tenth embodiment of the present invention will be described with reference to FIGS. 18 and 19. FIG. 18 is a block diagram showing the arrangement of an ultrasonic distance measuring device according to the tenth embodiment of the present invention. FIGS. 19(a) and 19(b) are a waveform diagram showing a repetitive transmission of a transmission signal and a waveform diagram showing the reception of an echo.

In FIG. 18, reference numeral 9C designates a transmitter portion for generating a pulsative transmission signal as in the conventional art. Numeral 10c designates a receiver portion. The transmitter portion 9C is connected to the probe 6 and the input terminal of the receiver portion 10C is also connected to the probe 6. The output terminal of the receiver portion 10C is connected to the signal processor portion 11. The transmitter portion 9C and the receiver portion 10C are both connected to the controller portion 3. The remaining arrangement of the tenth embodiment is substantially the same as that of the first embodiment.

The operation of the tenth embodiment will be described. A pulsative transmission signal is generated by the transmitter portion 9C and transmitted to the probe 6. An echo is amplified by the receiver portion 10C, and transmitted to the signal processor portion 11. The pulse width of the echo is short as of the conventional one. The signal processor portion 11 obtains the amplitude or envelope of the short echo as in the previous case, and determines the # k-th portion in the first embodiment using the information of the envelope as in the procedure of the first embodiment. The above operation is carried out at the timings, which are different from the timings of the operations of the transmitter portion 9 and the receiver portion 10.

The transmitter portion 9 and the receiver portion 10 are operated as in the first embodiment, and the signal processor portion 11 carries out the same signal processing procedure as of the first embodiment. The information on the amplitude or envelope of the echo, which are used for determining the # k-th portion are obtained from the echo formed by operating the transmitter portion 9C and the receiver portion 10C.

Figure 20:
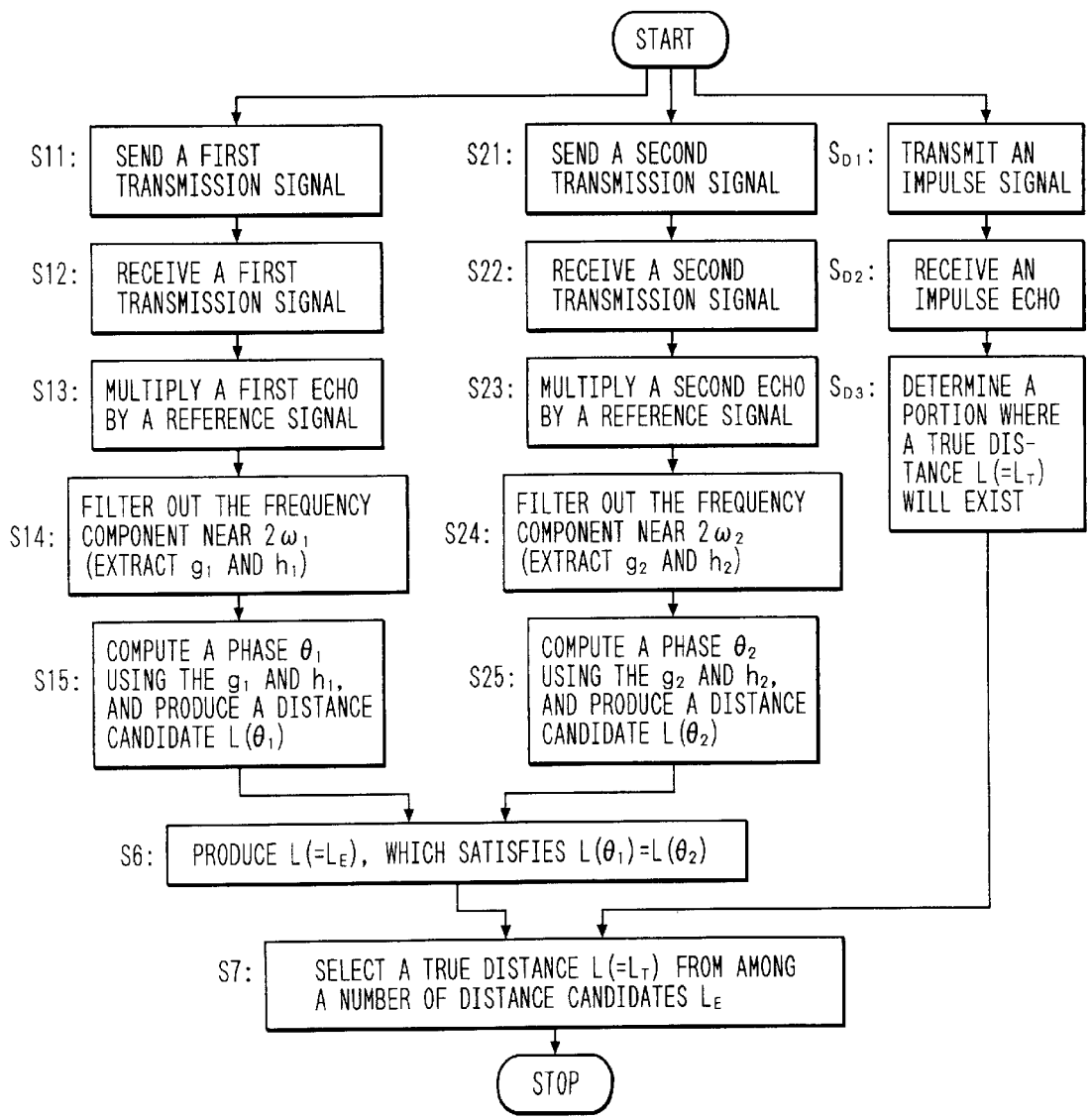
FIG. 20 shows a flowchart showing a first signal processing procedure in the tenth embodiment.

A procedure for signal processing in the present embodiment will be described with reference to FIGS. 20 and 21. In the flowchart of FIG. 20, a step $S_{D3}$ is used for the candidate-contained portion determining step $S_D$ in the flowchart of FIG. 6. An impulse signal transmission $S_{D1}$ and an impulse receiving step $S_{D2}$ are provided upstream of the step $S_{D3}$. The determination result from the candidate-contained portion determining step $S_{D3}$ is used by a step S7.

Figure 21:
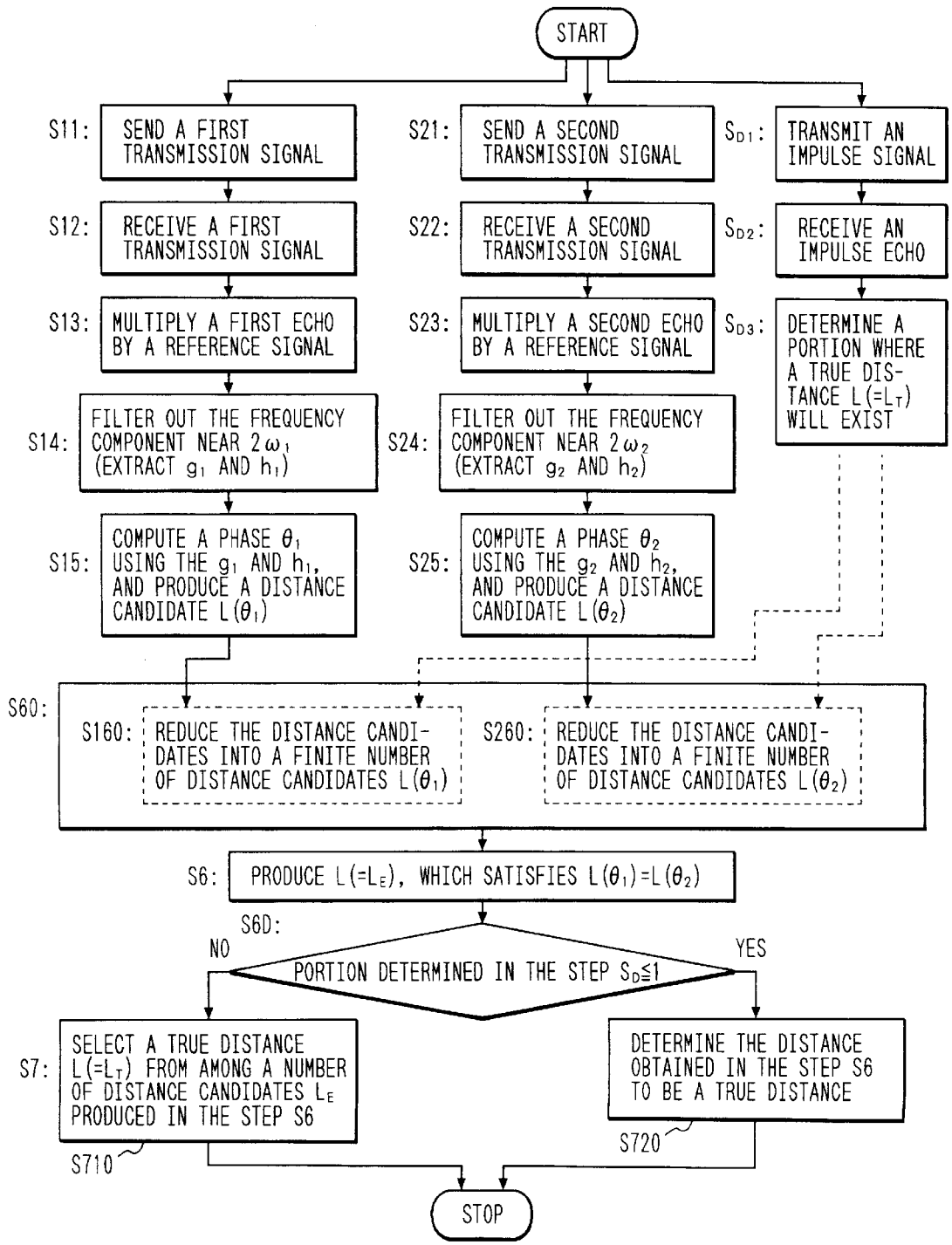
FIG. 21 shows a flowchart showing a second signal processing procedure in the tenth embodiment.

In the flowchart shown in FIG. 21, a step $S_{D3}$ is used for the candidate-contained portion determining step $S_D$ in the flowchart of FIG. 8. The flowchart of FIG. 21 is substantially the same as that of FIG. 7 or 8 except that the steps $S_{D1}$, $S_{D2}$, and $S_{D3}$ are used.

The signal processing procedure shown in FIG. 21 has the useful effects by the procedures of FIGS. 7 and 8, in addition to the useful effect owing to the use of the echo exclusively used for the candidate-contained portion determination.

The operations and the useful effects resulting from the operations of the tenth embodiment will be described. In the tenth embodiment, the information on the amplitude or the envelope of the echo signal of the short pulse width, which is obtained by operating the transmitter portion 9C and the receiver portion 10C, are used for the signal to determine the # k-th portion. The pulse width of the echo signal is much shorter than the period $q\pi v/\Delta\omega$ shown in FIG. 4. Even under the condition of large noise, viz., when much noise is contained in the echo, a probability that the signal processor portion 11 mistakenly determines the # k-th portion is considerably reduced.

In the arrangement of the ultrasonic distance measuring device that is described above, the two transmitter portions 9 and 9C, and the two receiver portions 10 and 10C are provided. In connection with this, the transmitter portion 9 and the receiver portion 10 may be designed so that these portions also serve as the transmitter portion 9C and the receiver portion 10C, respectively. In this case, the transmitter portion 9C and the receiver portion 10C are not used. The transmitter portion 9 repetitively transmits the impulse signal, and the first and the second transmission signals, as shown in FIG. 19(a). Accordingly, an echo signal corresponding to the impulse transmission signal, a first echo corresponding to the first transmission signal, and a second echo corresponding to the second transmission signal are repetitively received as shown in FIG. 19(b). Of those echoes, the echo corresponding to the impulse transmission signal is picked up, and information on the amplitude or the envelope of the picked up echo are used for determining the # k-th portion as in the previous case.

In the present invention, the impulse echo is used for the signal to determine the candidate-contained portion. The signal may take any waveform if it is as described below. It may be any echo of which the signal waveform continuation time is shorter than the signal waveform continuation time each of the first and the second echo, which are determined by the angular frequency $\omega_1$, the angular frequency $\omega_2$, and the signal propagating speed. To be more specific, the waveform continuation time of the echo to determine the candidate-contained portion (the echo is the first impulse echo as counted from the origin on the time axis) is much shorter than the waveform continuation time of the first echo or the second echo in the case of FIG. 19(b).

The transmission period of the first transmission signal may be different from that of the second transmission signal, although these periods are equal to each other in the present embodiment.

In some cases, the impulse echo, or the echo for determining the candidate-contained portion, may overlap with the first echo or the second echo in time, although these echoes are separated in time in FIG. 19(b).

11th Embodiment

Figure 22:
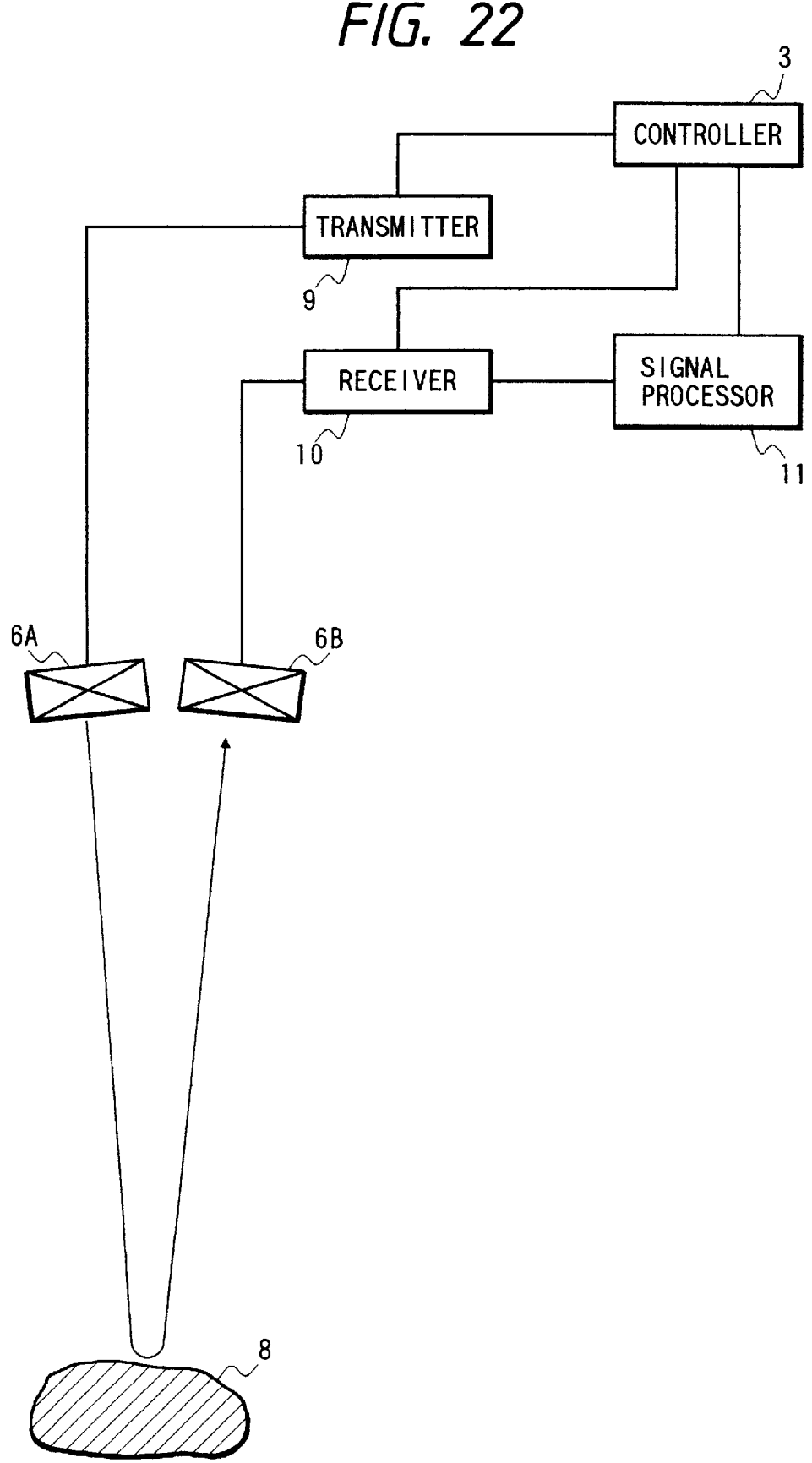
FIG. 22 shows a block diagram showing the arrangement of an ultrasonic distance measuring device according to an eleventh embodiment of the present invention.

The 11th embodiment of the present invention will be described with reference to FIG. 22. FIG. 22 is an arrangement diagram for explaining the 11th embodiment of the present embodiment. As shown, two probes 6A and 6B are separately provided. The probe 6A is connected to the transmitter portion 9, and the probe 6B is connected to the receiver portion 10. The transmitter portion 9 is not connected to the receiver portion 10, although these portions are connected in the first embodiment. The remaining arrangement of the tenth embodiment is substantially the same as that of the first embodiment.

The operation of the 11th embodiment will be described. In the 11th embodiment, a transmission signal is generated by the transmitter portion 9 and transmitted to the probe 6A. In response to this signal, the probe 6A generates an ultrasonic pulse for transmission to the object 8. An echo from the object is received by the probe 6B and transferred to the receiver portion 10. Other operations of the 11th embodiment are substantially the same as those of the first embodiment.

The operations of the 11th embodiment and the useful effects caused by the operations will be described. In the first embodiment, one probe 6 serves as both the transmitting probe and the receiving probe. The transmitter portion 9 and the receiver portion 10 are connected to each other. Part of the transmission signal leaks into the receiver portion 10. For this reason, during a time period where the transmission signal continues, it is impossible to use the probe for echo reception. In other words, this time period is dead. This implies that a dead region corresponding to the dead time is present in the ultrasonic wave propagating medium. An object 8 located in the dead region cannot be measured. In the 11th embodiment, a transmission system and a receiving system are separated provided. To this end, the probe 6A is connected to the transmitter portion 9, and the probe 6B is connected to the receiver portion 10. Therefore, there is eliminated the leakage of the transmission signal into the receiver portion 10, and hence the dead region.

In the device of FIG. 22, two probes 6A and 6B are separately used. A single probe 6 constructed as illustrated in FIG. 16 may be used in place of the two separate probes. As shown, a probe 6 is constructed with two vibrating elements, which are coaxially arrayed and operate independently. One of the vibrating element is connected to the transmitter portion 9, while the other, to the receiver portion 10. In other words, a signal transmission system and a signal receiving system are separated. With this construction, the main beams of transmitting and receiving ultrasonic waves travel in the direction along the center axis of the probe 6. Accordingly, the main beams are both directed to a point on the object 8, without slantly directing the probes 6A and 6b as shown in FIG. 22.

If the probe 6 shown in FIG. 16 is used, the probe scan mechanism for moving the probe 6 for scan that is referred to in the seventh embodiment, may be simplified. Where the transmitting and receiving ultrasonic beams of the converging type are formed by using the two vibrating elements curved in shape, an advantage of the improved bearing resolution is additionally created.

As described in the second embodiment, as the durations of the first and the second transmission signal are longer, the spectra of these signals are narrower. Accordingly, if the filter portion 12 of the band-pass type is used and its frequency band is narrowed, the S/N ratio of the echo signal is improved. The same thing is true for the 11th embodiment. In the second embodiment, as the continuation time of the transmission signal is longer, the dead time becomes long. On the other hand, in the 11th embodiment, if the continuation time of the transmission signal is elongated, the S/N ratio is improved and no dead time problem arises. As a result, a further improvement of the measuring accuracy is secured.

12th Embodiment

Figure 24A:
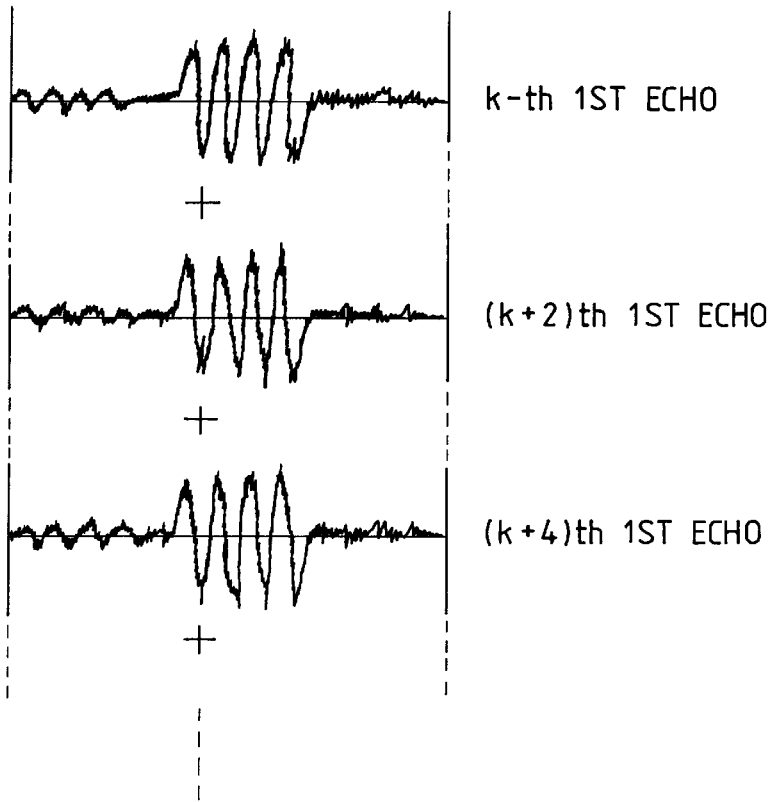
FIGS. 24(a) and 24(b) show waveform diagrams for explaining the operation of the twelfth embodiment.
Figure 24B:
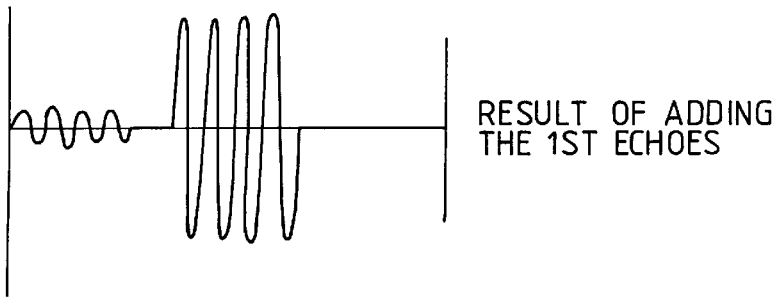
Figure 25A:
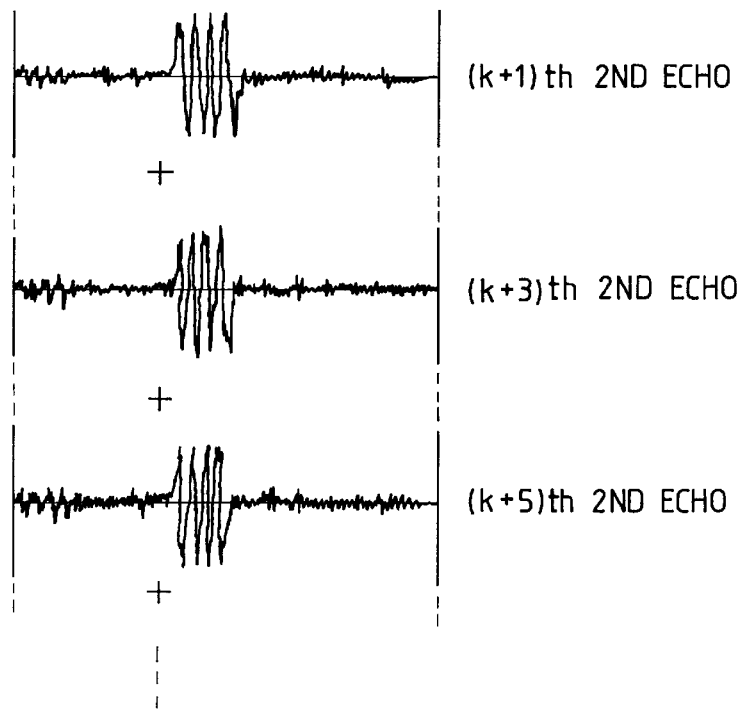
FIGS. 25(a) and 25(b) show waveform diagrams for explaining the operation of the twelfth embodiment.
Figure 25B:
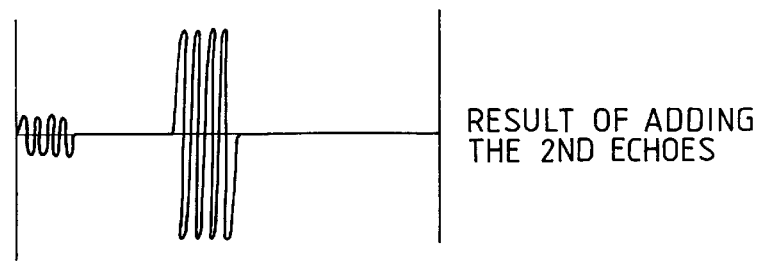

The 12th embodiment of the present invention will be described with reference to FIGS. 23, 24, and 25. The arrangement of the 12th embodiment is the same as that of the first embodiment. In FIG. 23 showing waveforms for explaining the 12th embodiment, FIG. 23(a) shows the waveforms of transmission signals repeatedly transmitted, and FIG. 23(b) shows the waveforms of echoes received. FIG. 24(a) shows waveforms of a plural number of first echoes, and FIG. 24(b) shows waveforms of the result of synchronously adding the first echoes together or the averaged result thereof. FIG. 25(a) shows waveforms of a plural number of second echoes, and FIG. 25(b) shows waveforms of the result of synchronously adding the second echoes together or the averaged result thereof.

The operation of the 12th embodiment will be described. As in the first embodiment, the first and the second transmission signal are alternately transmitted as shown in FIG. 25(a).

As in the first embodiment, the first and the second echo are alternately received, as shown in FIG. 24(b). In FIG. 25(b), leakage of part of the first and the second transmission signal into the receiver portion 10 is also illustrated.

The first and the second echo are stored into a memory in the signal processor portion 11 every transmission repetitive period Tτ, and these are synchronously added or the result of the addition is averaged. The receiving signal during the k-th transmission repetitive period corresponds to the first echo. k and p are natural numbers. As shown in FIG. 24(a), the first echoes during the k-th, (k+2)th, (k+4)th, . . . , (k+2p)th transmission repetitive periods are added together in synchronism with generation of the first transmission signal during each transmission repetitive period, or the result of the addition is averaged. The addition result or the addition/average result is shown in FIG. 24(b).

The receiving signal during the (k+1)th transmission repetitive period corresponds to the second echo. As shown in FIG. 25(a), the second echoes during the (k+1)th, (k+3)th, (k+5)th, ..., (k+1+2p)th transmission repetitive periods are added together in synchronism with generation of the second transmission signal during each transmission repetitive period, or the result of the addition is averaged. The addition result or the addition/average result is shown in FIG. 25(b).

As the result of the synchronous addition or the synchronous addition/average, the first and the second echo interact with each other such that one intensifies the other and vice versa. Noise additively applied to the first echo $\gamma_1(t)$ and noise to the second echo $\gamma_2(t)$ interact so as to cancel out. To show this state, waveforms are illustrated in FIGS. 24(a) and 25(a) in a state that noise is superposed on the first and the second echo. A state that these noise cancel out to be reduced is illustrated in FIGS. 24(b) and 25(b).

Consequently, the S/N ratio is improved, and the accuracy of measuring the phases, and the envelope or amplitude of the first and the second echo in the signal processor portion 11 is improved. And the accuracy of measuring the distance is improved. The noise typically includes thermal noise generated in the electric circuits, and ambient noise. When the measurement is carried out in a factory where large power consuming apparatus or equipment, such as a welding machine, are used, the 12th embodiment effectively operates.

In the instance of FIG. 23, the first and the second transmission signal are alternately repeated for transmission. In another process (not shown), the transmission of the first transmission signal is repeated p times at the transmission repetitive periods Tτ, and then the transmission of the second transmission signal is repeated p times at the transmission repetitive periods Tτ. The first echoes are synchronously added, and the second echoes are synchronously added. In yet another process, the transmission of the first and the second transmission signal are repeated same times, e.g., p times, and the these are synchronously added p times. The number of repetitions of the transmission of the first transmission signal may be different from that of repetitions of the transmission of the second transmission signal. The number of the synchronous additions of the first echoes may be different from that of the synchronous additions of the second echoes so as to secure given S/N ratios for the first and the second echo.

13th Embodiment

The 13th embodiment of the present invention will be described. The arrangement of the 13th embodiment is substantially the same as that of the first embodiment.

The operation of the 13th embodiment will be described. Also in the 13th embodiment, the synchronous addition is carried out p times for the first and the second echo, to thereby obtain the phases and amplitudes or envelope information, as in the 12th embodiment. The signal processing operation to obtain the phases and amplitudes or envelope information based on the synchronous additions is repeated g times (g: natural number). As the result of the signal processing operations, g number of data on the phases of the first and the second echo are obtained. The same thing is true for the amplitudes and the envelopes.

The g number of data on the amplitude and the envelope are further subjected to the addition or the addition/averaging process. The g number of data on the phase are subjected to the addition/averaging process.

The major difference of the 13th embodiment from the 12th embodiment follows. In the 12th embodiment, the synchronous addition process is carried out p times on the first and the second echo, and the phases are obtained on the basis of the addition result. In the 13th embodiment, this addition process is repeated g times, to thereby obtain g number of phase data. Further, the g number of phase data is added and averaged.

In the 13th embodiment, on the basis of the information of the phase, and amplitude and the envelope that are obtained from the signal processing result, a distance L is computed in the procedure described in the first embodiment.

The operations and the useful effects resulting from the operations in the 13th embodiment will be described. In the 13th embodiment, the signal processing operation to obtain the phases of the first and the second echo phases which are carried out on the basis of the results of the p number of synchronous additions is repeated g times, and the g number of phase data are added and averaged. Accordingly, adverse effect by the noise additively superposed on the phase of the echo, viz., for the first echo, noise added to $(\omega_1 t + \phi_1 - 2L\omega_1/V)$ in the right side of the equation (2), can be reduced. Thus, the 13th embodiment has the advantages to reduce the adverse effect by the superposed noise in addition to the advantage of the 12th embodiment.

A fluctuation of the phase, which is due to a variation of the ambient conditions of the ultrasonic wave propagating medium, is typically enumerated for this type of noise. Generally, air motion, temperature, humidity and the like fluctuate in the air, water or gas or liquid during a measurement. The 13th embodiment effectively reduces the adverse effect by the phase fluctuation caused by the fluctuation of the ambient conditions of this type. When a desired accuracy of the measure is secured only by removing the adverse effect by the phase fluctuation, the number p, of the synchronous additions may be reduced. In an extreme case, one synchronous addition suffices.

14th Embodiment

Figure 26:
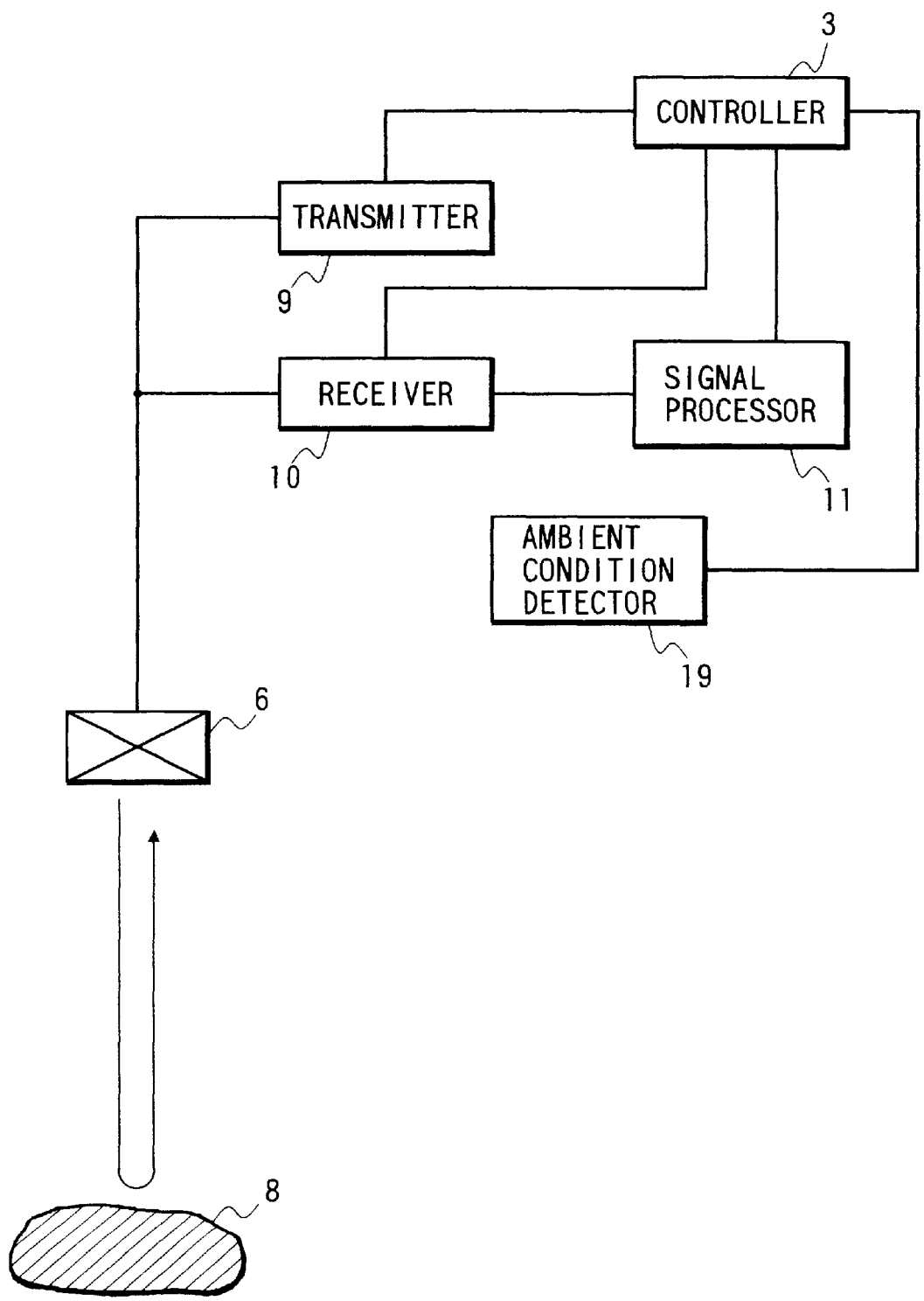
FIG. 26 shows a block diagram showing the arrangement of an ultrasonic distance measuring device according to a 14th embodiment of the present invention.

The 14th embodiment of the present invention will be described with reference to FIG. 26. FIG. 26 is a block diagram showing the arrangement of an ultrasonic distance measuring device according to a 14th embodiment of the present invention. In FIG. 26, reference numeral 19 designates an ambient condition detector portion. The ambient condition detector portion 19 is connected to the controller portion 3 and the signal processor portion 11. The remaining arrangement of the 14th embodiment is substantially the same as that of the first embodiment.

In an actual measurement in a site, there are various types of fluctuations, such as periodic noise generated by rotary machines including motors and by electronic devices including computers, and periodic fluctuations of air motion and temperature caused by air conditioners. The 14th embodiment of the present invention has an object to eliminate the adverse effect of the periodic noise and fluctuations on the measuring results.

The operation of the 14th embodiment will be described. In the 14th embodiment, the ambient condition detector portion 19 detects a variation of the ambient conditions. By using the information collected by the ambient condition detector portion 19, the controller portion 3 controls the transmission repetitive periods Tτ of the first and the second transmission signal so as not to be equal to the periods of the ambient condition variations.

With regard to the repetition of the first and the second transmission signal, as in the first embodiment, the transmission of these signals may be alternately repeated or as in the 12th embodiment, the first transmission signal may be successively repeated plural times, and then the second transmission signal may be successively repeated plural times.

The operations of the 14th embodiment and the useful effects caused by the operations will be described. In the 14th embodiment, the periodicities of variations of the ambient conditions are detected, and the detected periods and the transmission repetitive period Tτ are staggered. Accordingly, the periods causing the first and the second echo are not synchronized with the periods of the ambient condition variations.

The periodicities of the ambient condition variations cancel out by applying the addition or the addition/averaging process referred to in the 12th embodiment and the 13th embodiment to the signals. As a result, the accuracy of the measurement is improved.

15th Embodiment

Figure 27:
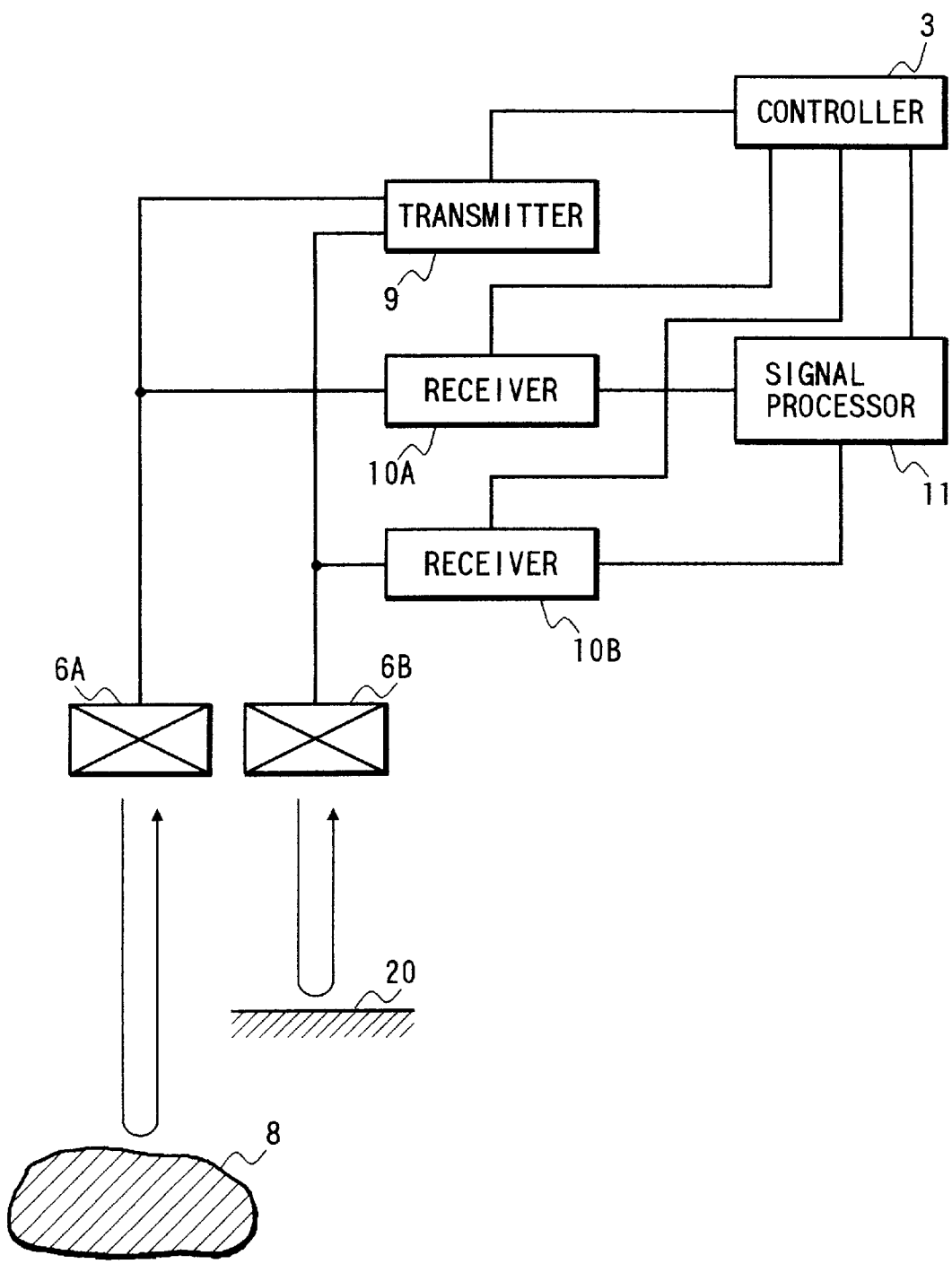
FIG. 27 shows a block diagram showing the arrangement of an ultrasonic distance measuring device according to a 15th embodiment of the present invention.

The 15th embodiment of the present invention will be described with reference to FIG. 27. FIG. 27 is a block diagram showing the arrangement of an ultrasonic distance measuring device according to a 15th embodiment of the present invention. In the figure, reference numeral 20 designates a reference reflecting surface. As shown in FIG. 22, two probes 6A and 6B are separately provided. The probe 6A is used in connection with an object 8, while the probe 6B is used in connection with the reference reflecting surface 20.

In FIG. 27, the transmitter portion 9 is provided with two output terminals. These terminals are a first output terminal and a second output terminal.

The output signals appearing at the first and the second output terminal of the transmitter portion 9 in the 15th embodiment are different from those appearing at the first and the second output terminal of the transmitter portion 9 in the 8th embodiment shown in FIG. 15.

Those transmission signals from the first and the second output terminals of the transmitter portion 9 in the 15th embodiment will be described later.

In FIG. 27, two receiver portions 10A and 10B are provided. The probe 6A is connected to the first output terminal of the transmitter portion 9 and the input terminal of the receiver portion 10A. The probe 6B is connected to the second output terminal of the transmitter portion 9 and the input terminal of the receiver portion 10B.

The output terminals of the receiver portions 10A and 10B are connected to the signal processor portion 11.

The receiver portions 10A and 10B are connected to the controller portion 3.

The remaining arrangement of the 15th embodiment is substantially the same as that of the first embodiment.

The operation of the 15th embodiment will be described.

The transmitter portion 9 alternately generates first and second transmission signals at the transmission repetitive periods Tτ. These transmission signals are outputted through two routes, the first and the second output terminals of the transmitter portion 9.

Accordingly, the transmission signals that are outputted from the first and the second output terminals of the transmitter portion 9 to the probes 6A and 6B are the same, and the same as used in the first embodiment.

In this respect, the 15th embodiment is different from the 8th embodiment.

The probe 6A transmits and receives ultrasonic pulses corresponding to the first and the second signal to and from the object 8. The probe 6B transmits and receives ultrasonic pulses corresponding to the first and the second signal to and from the reference reflecting surface 20.

The first and the second echo from the object 8 that are received by the probe 6A are transferred to the receiver portion 10A.

The first and the second echo from the reference reflecting surface 20 that are received by the probe 6B are transferred to the receiver portion 10B. The output signals of the receiver portions 10A and 10B are transmitted to the signal processor portion 11.

A distance between the probe 6B and the reference reflecting surface 20 is previously measured.

In the signal processor portion 11, the amplitudes or envelopes, and phases $\theta_1$ and $\theta_2$ of the first and the second echo from the reference reflecting surface 20 are obtained in the procedure as in the first embodiment.

A distance from the probe to the reference reflecting surface 20, the angular frequencies $\omega_1$ and $\omega_2$ of the transmission signals are already known. Then, a sonic speed V in the ultrasonic wave propagating medium can be obtained using the equations (7) and (8).

Using the sonic speed V thus obtained, the signal processor portion 11 computes a distance L from the probe to the object 8 in the same procedure as of the first embodiment, from the first and the second echo.

The operations of the 15th embodiment and the useful effects caused by the operations will be described. In the 15th embodiment, if a sonic speed in the ultrasonic wave propagating medium is unknown, it can be obtained from the echo received by the probe 6B, with provision of the reference reflecting surface 20 and the probe 6B associated therewith.

A distance to the object 8 can be obtained using the sonic speed thus obtained and the echo from the probe 6A. The ultrasonic distance measuring device of the 15th embodiment is very useful in a situation where the sonic speed in the ultrasonic wave propagating medium varies every moment with the ambient conditions.

The factors causing such a sonic speed variation includes time variation of temperature, humidity, pressure, salt concentration, and the like.

As seen from the above description, if in the first embodiment, the object 8 is replaced by the reference reflecting surface 20, the distance between the reference reflecting surface 20 and the probe 6 being known, the sonic speed in the ultrasonic wave propagating medium can be measured in a high accuracy. For the sonic speed measurement, if the ultrasonic wave propagating medium is solid, the bottom surface of the solid may be used for the reference reflecting surface 20. The fact that a correlation is present between the sonic speed in the solid material and a degree of deterioration of the material, is known. The well grasping of the sonic speed aging of the materials of the related parts and components leads to well grasping the degree of deterioration of the material. Accordingly, an estimated accuracy of the product lifetime is improved.

16th Embodiment

Figure 28:
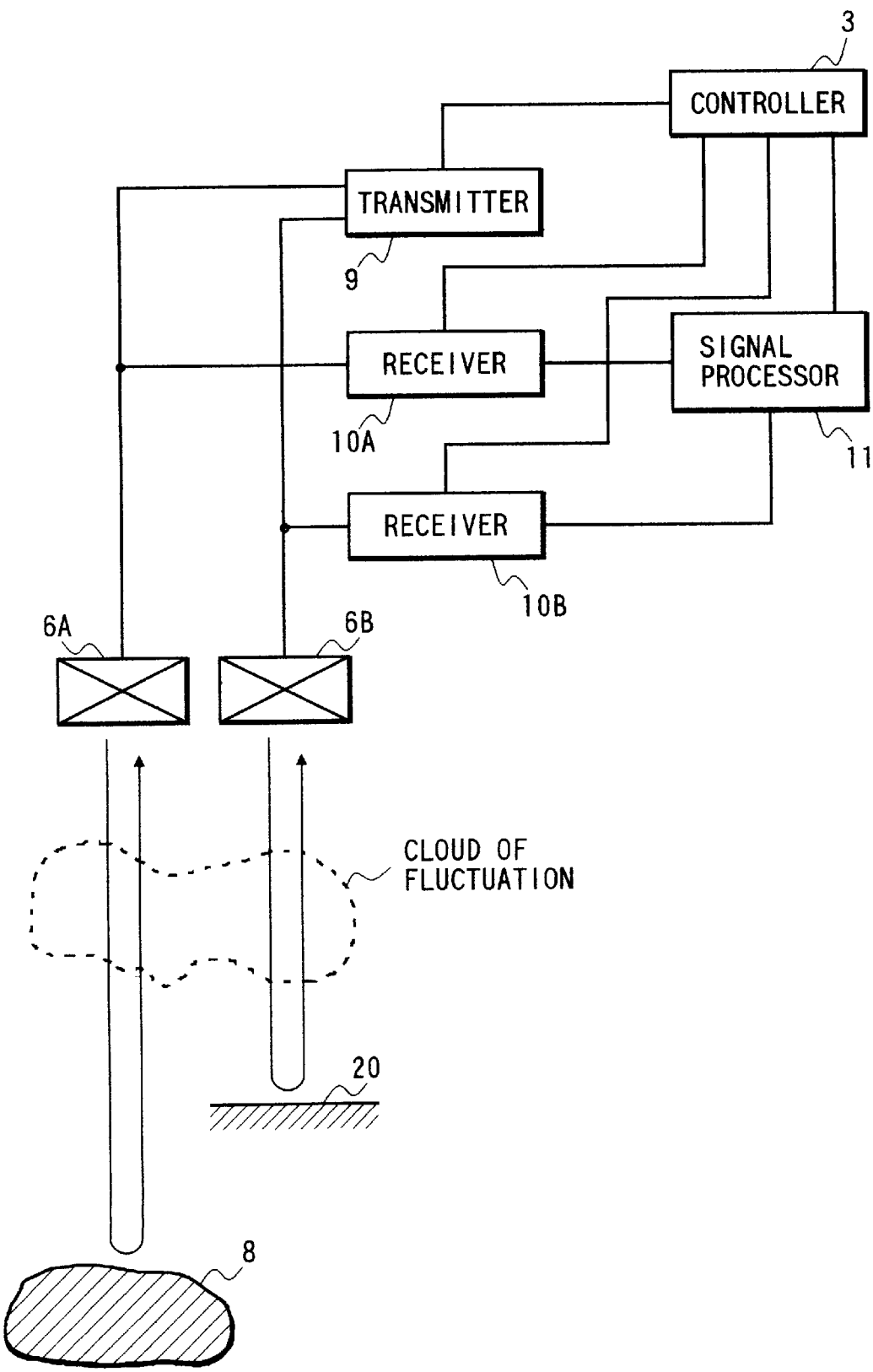
FIG. 28 shows a block diagram showing the arrangement of an ultrasonic distance measuring device according to a 16th embodiment of the present invention.

The 16th embodiment of the present invention will be described with reference to FIG. 28. The arrangement of the 16th embodiment, as shown in FIG. 28, is the same as that of the 15th embodiment shown in FIG. 27. In FIG. 28, a cloud of fluctuation is additionally depicted in the ultrasonic wave propagating medium.

The operation of the 16th embodiment will be described. The operations of the transmitter portion 9, the probes 6A and 6B, and the receiver portions 10A and 10B are the same as those in the 15th embodiment. A distance between the reference reflecting surface 20 and the probe 6B has been measured by any of other measuring means than the measuring means using an ultrasonic wave, for example, a scale, and hence is known.

The signal processor portion 11 processes the first and the second echo from the reference reflecting surface 20 in the same procedure as in the first embodiment, to thereby obtain a distance between the reference reflecting surface 20 and the probe 6B. The measured distance should be equal to the known distance, measured by another means. In such a situation where ambient conditions varies with time, the two distances frequently becomes unequal, causing a difference $\Delta L$ (=measuring value–true value).

The 16th embodiment has an object to accurately measure the distance from the probe 6A to the object 8 even in the above situation.

When the distance between the reference reflecting surface 20 and the probe 6B is computed in the signal processing procedure of the first embodiment, the phases $\theta_1$ and $\theta_2$ on the first and the second echo that are produced during this computing process are respectively expressed as $\theta_{1r}$ and $\theta_{2r}$, for ease of explanation. When the distance between the object 8 and the probe 6A is computed in the signal processing procedure of the first embodiment, the phases $\theta_1$ and $\theta_2$ on the first and the second echo that are produced during this computing process are respectively expressed as $\theta_{1o}$ and $\theta_{2o}$, for ease of explanation.

In computing the distance between the reference reflecting surface 20 and the probe 6B, the phases $\theta_{1r}$ and $\theta_{2r}$ on the first and the second echo, which are used for computing the distance, have been obtained. When the distance difference $\Delta L$ is caused, differences are present between the phase $\theta_{1r}$ and the true value and between the phase $\theta_{2r}$ and the true value. These differences are denoted as $\Delta \theta_{1r}$ and $\Delta \theta_{2r}$ and are expressed by $$\Delta \theta_{1r} = (\text{measuring value}) - (\text{true value}) = 2\Delta L \omega_1 / V$$

$$\Delta \theta_{2r} = (\text{measuring value}) - (\text{true value}) = 2\Delta L \omega_2 / V$$

In the above equations, numeral 2 indicates that an ultrasonic pulse goes to and returns from the reference reflecting surface 20.

The ambient variations are air motion, variations of temperature and humidity when the ultrasonic wave propagating medium is air. When the ultrasonic wave propagating medium is water or sea, water or sea water motion, and variation of temperature and salt.

The ambient variation can be considered to be uniform when locally viewed. This type of the ambient variation mainly influences the phase of the echo, and it is observed as a variation of the phase. Accordingly, the propagating path of the ultrasonic pulse between the reference reflecting surface 20 and the probe 6B associated therewith is closely located to the propagating path of the ultrasonic pulse between the object 8 and the probe 6A associated therewith. Where these paths are located within a cloud of fluctuation (indicated by a dotted line in FIG. 23) where the variation is considered to be uniform when viewed locally, the two ultrasonic pulses undergo substantially equal phase variations, and are received as the echoes.

In the 16th embodiment, the following signal processing is carried out in the signal processor portion 11.

During the transmission repetitive period $T\tau$ at which the first transmission signal is transmitted, the phase difference $\Delta \theta_{1r}$ corresponding to the $\Delta L$ is obtained and stored. The first echo from the object 8 is processed in the procedure of the first embodiment, thereby to obtain the phase $\theta_{1o}$. The phase difference $\Delta \theta_{1r}$ is subtracted from the phase $\theta_{1o}$. In the result of the subtraction, the phase variations cancel out and hence it is a corrected signal.

Also during the transmission repetitive period $T\tau$ at which the second transmission signal is transmitted, a similar signal processing is carried out. Specifically, the phase difference $\Delta \theta_{2r}$ corresponding to the $\Delta L$ is obtained and stored. The second echo from the object 8 is processed in the procedure of the first embodiment, thereby to obtain the phase $\theta_{2o}$. The phase difference $\Delta \theta_{2r}$ is subtracted from the phase $\theta_{2o}$. In the result of the subtraction, the phase variations cancel out and hence it is a corrected signal.

In the 16th embodiment, a distance to the object 8 is computed in the signal processing procedure of the first embodiment, by using the phase corrected by the above-mentioned procedure, $(\theta_{1o} - \Delta \theta_{1r})$ and $(\theta_{2o} - \Delta \theta_{2r})$.

In the 16th embodiment, the phase correction procedure is added to the first embodiment. Therefore, a measurement error caused by ambient variations is reduced.

Where the propagating path of the ultrasonic pulse between the reference reflecting surface 20 and the probe 6B associated therewith and the propagating path of the ultrasonic pulse between the object 8 and the probe 6A associated therewith are located within a spatial area where the variation is considered to be uniform when viewed locally, the above useful effects are obtained even if the ambient variations are quick. As seen from the above description, what are necessary for the phase correction are phase differences $\Delta \theta_{1r}$ and $\Delta \theta_{2r}$. In other words, the distance difference $\Delta L$ is not essential.

17th Embodiment

Figure 29:
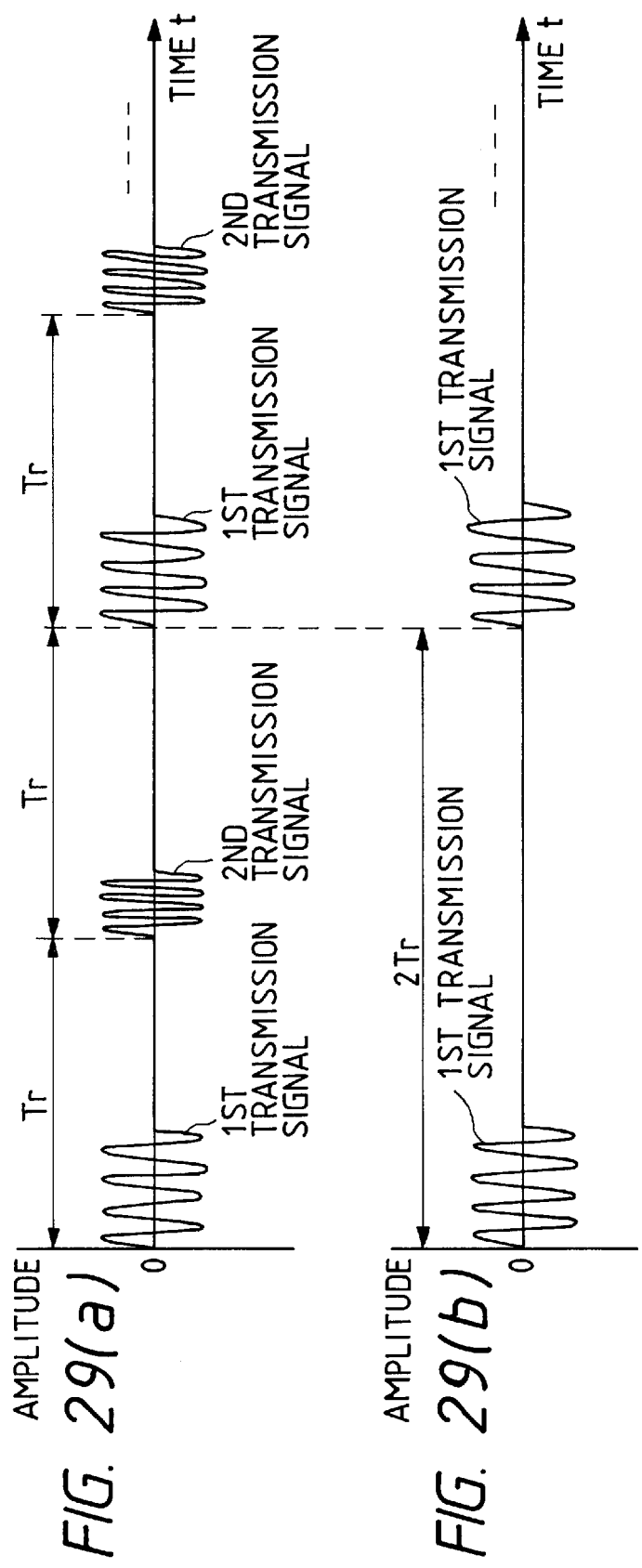
FIGS. 29(a) and 29(b) show waveform diagrams showing the operation of the 17th embodiment of the present invention.

The 17th embodiment of the present invention will be described with reference to FIG. 29. FIGS. 29(a) and 29(b) show waveforms of the first and the second transmission signal.

The arrangement of the 17th embodiment is the same as that of FIG. 28 shown in FIG. 16. In the 17th embodiment, a transmission signal outputted from the second output terminal of the transmitter portion 9 to the probe 6B shown in FIG. 28 is different from that in the 16th embodiment. This transmission signal is shown in FIG. 29(b). In the 17th embodiment, a transmission signal transmitted from the second output terminal of the transmitter portion 9 to the probe 6B provided in association with the reference reflecting surface 20 is only the first transmission signal that is repeated at the two transmission repetitive periods $2T\tau$ as shown in FIG. 29(b).

Transmission signals transmitted from the first output terminal of the transmitter portion 9 to the probe 6A provided associated with the object 8 are shown in FIG. 29(a). These signals are the first and the second transmission signal alternately repeated at the transmission repetitive periods $T\tau$ as in the 16th embodiment.

Also in the 17th embodiment, as in the 16th embodiment, it is assumed that a distance between the reference reflecting surface 20 and the probe 6B is already known.

The operation of the 17th embodiment will be described. The first echo from the reference reflecting surface 20 is processed in the same procedure in the first embodiment, to thereby obtain the phase $\theta_{1r}$. Since the distance between the reference reflecting surface 20 and the probe 6B is already known, the phase difference $\Delta \theta_{1r}$ caused by the ambient variation as in the 16th embodiment is obtained. A distance difference $\Delta L$ is computed by using the phase difference $\Delta \theta_{1r} = 2\Delta L \omega_1 / V$.

The phase difference $\Delta \theta_{2r}$ caused when the second transmission signal is transmitted from the probe 6B to the reference reflecting surface 20 is predicted by using the distance difference $\Delta L$ obtained in the above-mentioned procedure and the following equation, $\Delta \theta_{2r} = 2\Delta L \omega_2 / V$.

By using the phase differences $\Delta\theta_{1r}$ and $\Delta\theta_{2r}$ obtained in the above procedure, for the phases $\theta_{1o}$ and $\theta_{2o}$ of the first and the second echo from the probe 6A, which is provided in association with the object 8, correction for the phase variations $\Delta\theta_{1r}$ and $\Delta\theta_{2r}$ caused by ambient variations is carried out in the procedure of the 16th embodiment. By using the correction result, a distance L to the object 8 is obtained.

The operations and the effects caused by the operations of the 17th embodiment will be described. In the 17th embodiment, the transmission repetitive period of the first transmission signal transmitted to the probe 6B provided in association with the reference reflecting surface 20 is denoted as 2T$\tau$, the phase difference $\Delta\theta_{1r}$ used for correction is obtained from the measuring value, a distance $\Delta$L is computed using the result thereof, and the phase difference $\Delta\theta_{2r}$ is computed using the distance difference $\Delta$L. A distance from the probe 6A to the object 8 is obtained using this predictive value. Accordingly, when the phase variation caused by the ambient variation is slower than the period 2T$\tau$, a measuring error caused by the ambient variation is reduced.

In the 17th embodiment, the transmission repetitive period of the first transmission signal transmitted to the probe 6B, which is provided in association with the reference reflecting surface 20, is 2T$\tau$. Accordingly, the average transmission power can be halved. This power reduction effect leads to source and energy saving. The 17th embodiment is very useful when it is used in a place where the ultrasonic distance measuring device must be driven by a battery, or a measuring place where the ultrasonic distance measuring device cannot be moved while pulling the power cable thereof along behind, such as height or narrow place.

18th Embodiment

The 18th embodiment of the present invention will be described with reference to FIG. 29. FIGS. 29(*a*) and 29(*b*) show waveforms of the first and the second transmission signal.

The arrangement of the 18th embodiment is the same as that of FIG. 28 in the 16th embodiment. In the 18th embodiment, the transmission signals that are applied from the first and the second output terminals of the transmitter portion 9 shown in FIG. 28 to the probe 6A for the object 8 and the probe 6B for the reference reflecting surface 20, are different from those in the 16th embodiment.

Figure 30:
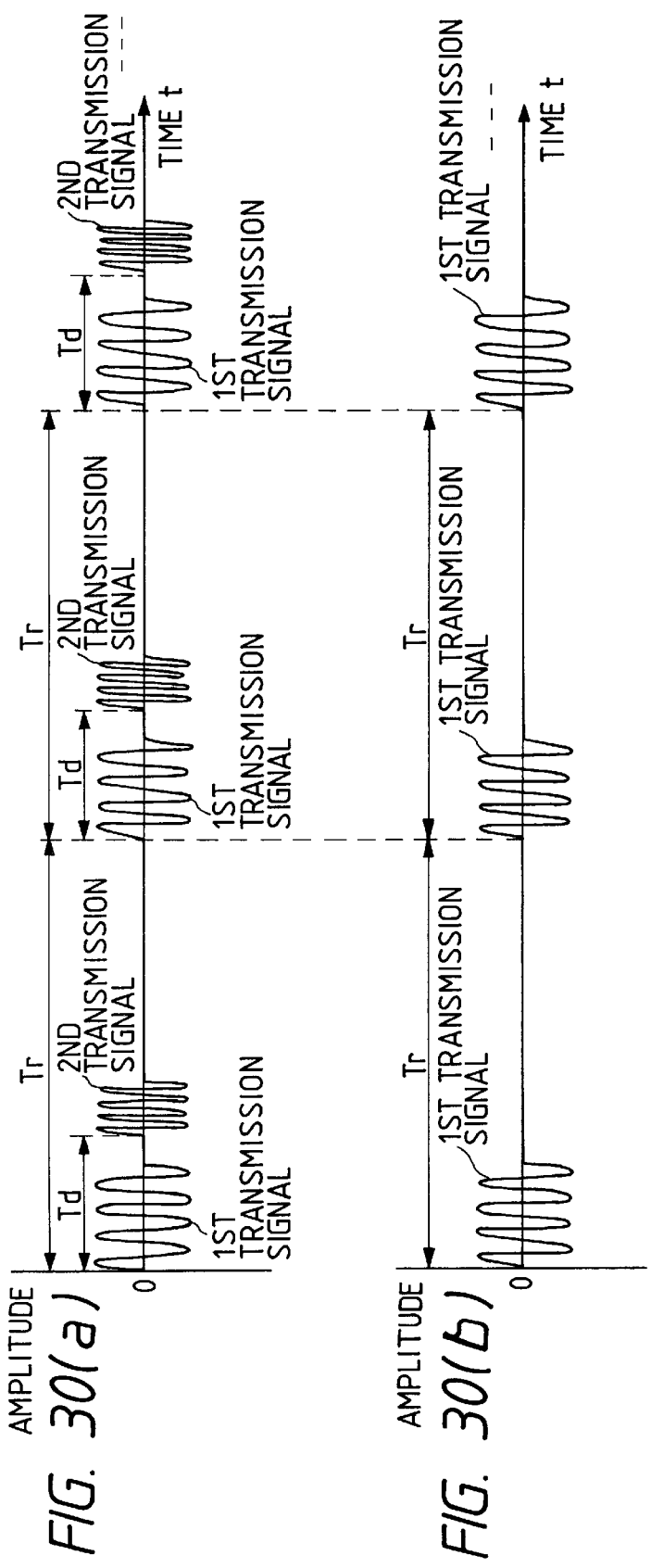
FIGS. 30(a) and 30(b) show waveform diagrams showing the operation of the 18th embodiment of the present invention.

The transmission signals transmitted from the first output terminal of the transmitter portion 9 are shown in FIG. 30(*a*). The transmission signals transmitted from the second output terminal are shown in FIG. 30(*b*).

In the 18th embodiment, the transmission signals transmitted from the first output terminal of the transmitter portion 9 to the probe 6A are such that immediately after the first transmission signal is transmitted, the second transmission signal is generated. A time interval between generation time of the first transmission signal and the generation time of the second transmission signal is denoted as Td as shown. In FIG. 30(*a*), when seeing only the first transmission signal, the first transmission signal is repeated at the transmission repetitive periods T$\tau$. Similarly, when seen only the second transmission signal, the second transmission signal is also repeated at the transmission repetitive periods T$\tau$.

As shown in FIG. 30(*b*), the transmission signal transmitted from the second output terminal of the transmitter portion 9 to the probe 6B is such that only the first transmission signal is repeated at the transmission repetitive periods T$\tau$.

Also in the 18th embodiment, a distance between the reference reflecting surface 20 and the probe 6B has exactly been known as in the 16th and the 17th embodiments.

The operation of the 18th embodiment will be described. A phase difference $\Delta\theta_{1r}$ for correcting a phase variation caused by ambient condition variations is obtained in the same procedure as in the 17th embodiment, from the first echo received by the probe 6B associated with the reference reflecting surface 20. Further, a distance difference $\Delta$L is obtained on the basis of the $\Delta\theta_{1r}$ in the same procedure as in the 17th embodiment. Subsequently, a phase difference $\Delta\theta_{2r}$ is predicted on the basis of the distance difference $\Delta$L when it is assumed that the second transmission signal is generated as shown in FIG. 30(*b*).

The first echo signal received by the probe 6A associated with the object 8 is processed in the same procedure as in the first embodiment, to thereby obtain a phase $\theta_{1o}$ and an envelope. Approximate time that the first echo is received is obtained form the amplitude or the envelope of the first echo.

Since the transmission time interval Td is already known, time the second echo is received by the probe 6A associated with the object 8 is known from the approximate time the first echo is received. On the basis of this time, the second echo is also processed in the same procedure as in the first embodiment, to thereby obtain a phase $\theta_{2o}$ and an envelope.

The phases $\theta_{1o}$ and $\theta_{2o}$ on the object 8 are corrected using the phase differences $\Delta\theta_{1r}$ and $\Delta\theta_{2r}$ in the same procedure as in the 17th embodiment. A distance L to the object 8 is obtained on the basis of the result.

The operations and the useful effects caused by the operations in the 18th embodiment will be described. In the 18th embodiment, the useful effects as those of the 17th embodiment are achieved. The transmission time interval Td between the first transmission signal and the second transmission signal is shorter than the transmission repetitive period T$\tau$. Accordingly, when comparing with the 17th embodiment, if the phase variation by the ambient condition variation is more quick than the transmission repetitive period T$\tau$, but slower than the transmission time interval Td, a measuring error caused by the ambient condition variation can be reduced.

19th Embodiment

The 19th embodiment of the present invention will be described with reference to FIG. 28, which is used for explaining the 16th embodiment. The arrangement of the 19th embodiment is the same as that of the 16th embodiment.

In the 16th embodiment, a distance between the object 8 and the probe 6A associated with the object 8 was measured. The 19th embodiment, unlike the 16th embodiment, has an object to measure a distance between the reference reflecting surface 20 and the object 8.

The operation of the 19th embodiment will be described. In the 19th embodiment, the transmission signals from the first and the second output terminals of the transmitter portion 9 are the same as those in the 16th embodiment.

The first and the second echo from the probe 6B associated with the reference reflecting surface 20 are processed as in the 16th embodiment, to thereby obtain phases $\theta_{1r}$ and $\theta_{2r}$. In the 19th embodiment, unlike the 16th embodiment, phase differences $\Delta\theta_{1r}$ and $\Delta\theta_{2r}$, caused by ambient condition variations, are not obtained.

The first and the second echo from the probe 6A associated with the object 8 are processed as in the 16th embodiment, to thereby obtain phases $\theta_{1o}$ and $\theta_{2o}$.

The following computing process are carried out using the phases $\Delta\theta_{1r}$, $\Delta\theta_{2r}$, $\theta_{1o}$ and $\theta_{2o}$. The phase $\theta_{1r}$ is subtracted from the phase $\theta_{1o}$. The phase $\theta_{2r}$ is subtracted from the phase $\theta_{2o}$. For the subtraction results, the following equations hold $$\theta_{1o} - \theta_{1r} = -2\omega_1(Lo-Lr)/V \quad (14.a)$$

$$\theta_{2o} - \theta_{2r} = -2\omega_2(Lo-Lr)/V \quad (14.b)$$

where Lo : distance between the probe 6A and the object 8

Lr: distance between the probe 6B and the reference reflecting surface 20

Where the propagating path of the ultrasonic pulse between the reference reflecting surface 20 and the probe 6B and the propagating path of the ultrasonic pulse between the object 8 and the probe 6A are located within a spatial area where the variation is considered to be uniform when viewed locally, if the ambient condition variations with respect to time are quick, the phase variation is superposed on both the phases $\theta_{1o}$ and $\theta_{1r}$. When the phase difference $\Delta\theta_{1r}$ caused by the ambient condition variation is superposed on the phase $\theta_{1r}$, the phase difference caused by the ambient condition variation superposed on the phase $\theta_{1o}$ is also $\Delta\theta_{1r}$.

The same thing is true for the phases $\theta_{2o}$ and $\theta_{2r}$. When the phase difference $\Delta\theta_{2r}$ caused by the ambient condition variation is superposed on the phase $\theta_{2r}$, the phase difference caused by the ambient condition variation superposed on the phase $\theta_{2o}$ is also $\Delta\theta_{2r}$.

Accordingly, the phase differences caused by the ambient condition variation cancel out by subtracting the phase $\theta_{1r}$ from the phase $\theta_{1o}$ the phase $\theta_{2r}$ from the phase $\theta_{2o}$.

The canceling effect is effective when the phase difference caused by the ambient condition variation has a large value in excess of integer times as large as $2\pi$. In such a case, the phase differences are completely neutralized.

The phase difference in excess of integer times as large as $2\pi$ are completely neutralized, as stated above. In the right sides of the equations (14.a) and (14.b), an indeterminacy of integer times as large as the phase concerning the relationship between the distance and the phase, like those expressed by $2n\pi$ and $2m\pi$ in the right sides of the equations (7) and (8) in the first embodiment, is still present. In the equations (14.a) and (14.b), the term for this is omitted for simplicity. The indeterminacy can be determined in the following procedure.

This can be considered that in FIGS. 3 and 4, the distance L on the abscissa is replaced by the distance difference (Lo–Lr). Although not illustrated, in the drawing in which such a replacement is made, as in the first embodiment, white circles and black circles are depicted at the phases ($\theta_{1o} - \theta_{1r}$) and ($\theta_{2o} - \theta_{2r}$). The period that the equal values corresponding to a white circle and a black circle on the abscissa are equal appear, is expressed by $q\pi V/\Delta\omega$, as in FIG. 4.

The first and the second echo from the probe 6A and the first and the second echo from the probe 6B are processed as in the first embodiment, to thereby obtain information on the amplitudes or the envelopes of those echoes. Accordingly, approximate values of the amplitudes or the envelopes of those echoes at the rising parts thereof can be obtained. These approximate values provide an approximate value of the distance difference (Lo–Lr). An indeterminacy difference of the phase can be determined by applying the approximate value of the distance difference (Lo–Lr) to the procedure to remove an indeterminacy of the phase that is carried out by using FIG. 5 in the first embodiment.

In this way, the distance difference (Lo–Lr) can be measured accurately.

The 19th embodiment has the following useful effects. In the 19th embodiment, a distance between the reference reflecting surface 20 and the probe 6A associated therewith may be unknown at the initial stage. In the 19th embodiment, a distance of the object 8 relative to the reference reflecting surface 20 is determined. If a part of the object 8 is used for the reference reflecting surface 20, it implies that the size of irregularity on the object 8 can be measured. A configuration of the object 8 can be measured in a manner that the probe 6B associated with the reference reflecting surface 20 is fixed, while the probe 6A associated with the object 8 is moved for scan.

Where the propagating path of the ultrasonic pulse between the reference reflecting surface 20 and the probe 6B and the propagating path of the ultrasonic pulse between the object 8 and the probe 6A are located within a spatial area where the variation is considered to be uniform when viewed locally, if the ambient condition variations with respect to time are quick, a distance from the reference reflecting surface 20 to the object 8 is computed by using the differences $\theta_{1o} - \theta_{1r}$ and $\theta_{2o} - \theta_{2r}$. Accordingly, the above phase variations are neutralized in the difference phases, $\theta_{1o} - \theta_{1r}$ and $\theta_{2o} - \theta_{2r}$. Accordingly, as in the 16th embodiment, a measuring error caused the ambient condition variation is reduced.

When a configuration of the object 8 is measured by moving the probe 6A relative to the object 8 as described above, the phase variations caused by the ambient condition variation cancel out. Accordingly, a measuring time at a point is reduced, so that scanning speed is increased. The configuration measurement can be carried out for a short time.

The probe 6A may be moved for scan in the direction parallel to the surface of the object 8 or in the direction of the object 8. In this case, a state of vibration when the object 8 slowly vibrates in the direction from the object 8 to the probe 6A, can be measured.

In the 16th, 17th, and 18th embodiments, when the probe is moved for scan, the useful effects as described above are obtained.

The operations of computing $\Delta\theta_{1r}$ and $\theta_{2r}$ are not performed in the 19th embodiment. Accordingly, the signal processing speed of the 19th embodiment is higher than the 16th embodiment by an amount corresponding to the computing operations.

20th Embodiment

Figure 31:
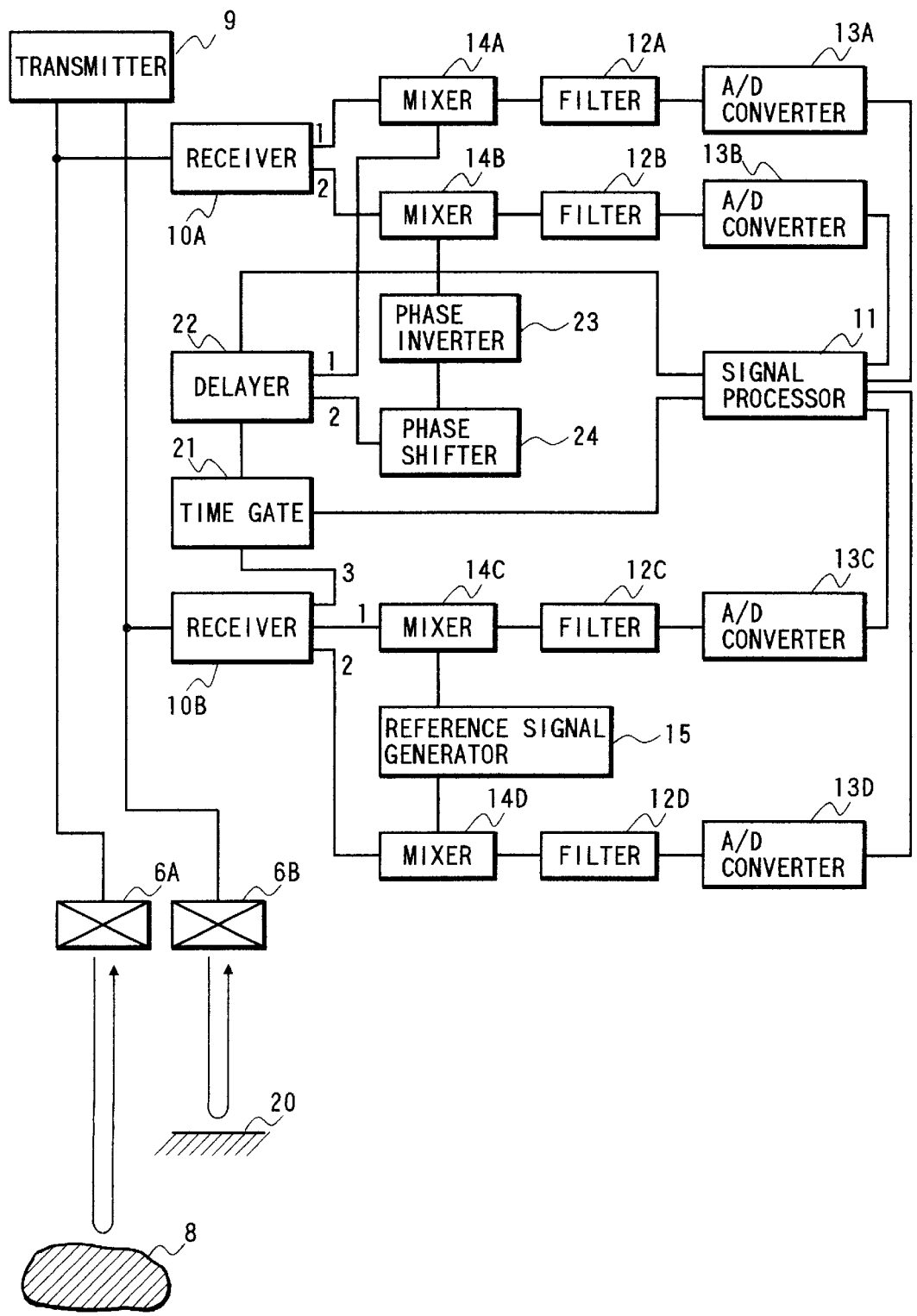
FIG. 31 shows a block diagram showing the arrangement of an ultrasonic distance measuring device according to a 20th embodiment of the present invention.

The 20th embodiment of the present invention will be described with reference to FIG. 31. FIG. 31 shows a block diagram showing of an ultrasonic distance measuring device according to a 20th embodiment of the present invention. In the figure, reference numeral 21 designates a time gate portion, and 22 a delay portion. Numeral 24 designates a phase shifter portion 24, and 23 a phase inversion portion.

12A to 12D designates filter portions; 13A to 13D, A/D converter portions; and 14A to 14D, mixer portions.

The arrangement of FIG. 31 will be described in comparison with the FIG. 10 arrangement of the third embodiment and the FIG. 28 arrangement of the 19th embodiment.

In FIG. 31, the transmitter portion 9 is the same as in the FIG. 31 of the 19th embodiment. The transmission signal is outputted from the first and the second output terminal of the transmitter portion 9.

The probes 6A and 6B are the same as those in FIG. 28 of the 19th embodiment.

The receiver portion 10A is the same as in FIG. 10 of the 3rd embodiment. The receiver portion 10B includes three output terminals. The received signal is passed through three routes of the output terminals. These three output terminals are referred to first, second and third output terminals.

The mixer portions 14A to 14D are the same those in FIG. 10 of the third embodiment.

The reference signal generator portion 15 is the same as in the third embodiment of FIG. 10. During the transmission repetitive period where the first transmission signal is transmitted, the first and the second reference signal of the first echo are outputted from the first and the second output terminals of the reference signal generator portion 15. During the transmission repetitive period where the second transmission signal is transmitted, the first and the second reference signal of the second echo are outputted.

The filter portions 12A to 12D are the same as those of FIG. 10 in the third embodiment. During the transmission repetitive period where the first echo signal is received from the probes 6A and 6B, those filter portions serve as low-pass filters filtering out the frequency components near the angular frequency $\omega_1$. During the transmission repetitive period where the second echo signal is received from the probes 6A and 6B, those filter portions serve as low-pass filters filtering out the frequency components near the angular frequency $\omega_2$.

The A/D converter portions 13A to 13D are the same as those of FIG. 10 in the third embodiment.

The signal processor portion 11 is similar to that of FIG. 10 in the third embodiment.

The time gate portion 21 operates such that when the time gate is opened, it allows the input signal to straightforwardly go to the output terminal, and when it is closed, it allows a signal of 0 in amplitude to the output terminal.

The delay portion 22 delays the input signal input thereto. The delay portion 22 includes two output terminals. These output terminals are first and second output terminals. The same signal is outputted through the first and the second output terminal.

The probe scan signal generator 16 shifts the phase of the input signal by 90° C. The phase shifting operation is performed independently of the type of the echo, the first echo or the second echo, or the frequency of the input signal.

In the phase inversion portion 23, the input signal is multiplied by −1.

The respective circuit portions in FIG. 31 are under control of a controller portion 3 (not shown).

In FIG. 31, the first and the second output terminal of the transmitter portion 9 are connected to the probes 6A and 6B, respectively. The first and the second input terminal of the receiver portions 10A and 10B are connected to the probes 6A and 6B, respectively.

The first and the second output terminal of the receiver portion 10A are connected to the input terminals of the mixer portions 14A and 14B, respectively. The output terminals of the mixer portions 14A and 14B are connected to the input terminals of the filter portions 12A and 12B, respectively. The output terminals of the filter portions 12A and 12B are connected to the input terminals of the A/D convertors 13A and 13B, respectively. The output terminals of the A/D convertors 13A and 13B are connected to the signal processor portion 11.

The first and the second output terminal of the receiver portion 10B are connected to the input terminals of the mixer portions 14C and 14D. The output terminals of the mixer portions 14C and 14D are connected to the input terminals of the filter portions 12C and 12D, respectively. The output terminals of the filter portions 12C and 12D are connected to the input terminals of the A/D convertors 13C and 13D, respectively. The output terminals of the A/D convertors 13C and 13D are connected to the signal processor portion 11.

The first and the second output terminals of a reference signal generator portion 15 are connected to the mixer portions 14C and 14D, respectively.

A third output terminal of the receiver portion 10B is connected to the input terminal of the time gate portion 21. The output terminal of the time gate portion 21 is connected to the input terminal of the delay portion 22.

The first output terminal of the delay portion 22 is connected to the mixer portion 14A. The second output terminal of the delay portion 22 is connected to the input terminal of the probe scan signal generator 16. The output terminal of the probe scan signal generator 16 is connected to the input terminal of the phase inversion portion 23. The output terminal of the phase inversion portion 23 is connected to the mixer portion 14B.

In FIG. 31, those circuit portions are connected to the controller portion 3, not shown.

The 20th embodiment, like the 19th embodiment, is arranged so as to measure a distance between the reference reflecting surface 20 and the object 8.

The operation of the 20th embodiment will be described. As in the 19th embodiment, the transmitter portion 9 alternately produces the first and the second transmission signal at the transmission repetitive periods $T\tau$, which are in turn transmitted to the probe 6A associated with the object 8 and the probe 6B associated with the reference reflecting surface 20.

The first and the second echo received by the probe 6B are transmitted to the receiver portion 10B. The signals from the first and the second output terminal of the receiver portion 10B are processed in the same signal processing procedure as used for processing the signals from the first and the second output terminal of the receiver portion 10 in the third embodiment, which are processed by the mixer portions 14C and 14D, reference signal generator portion 15, filter portions 12C and 12D, A/D convertors 13C and 13D, and the signal processor portion 11.

By the signal processing procedure, in the signal processor portion 11, a distance between the probe 6B and the reference reflecting surface 20 is computed. In the signal processor portion 11, the amplitudes of the first and the second echo, and the envelopes thereof are detected, to thereby obtain the information on the continuation time durations of the echoes.

The operations and the signal processing procedure are the same as in the third embodiment. When a phase fluctuates by ambient condition variations, the distance measured result is an approximate value, which is different from a true value.

In the 20th embodiment, the approximate value is used in the following way. When the distance between the reference reflecting surface 20 and the probe 6B associated therewith is already known, the above procedure is not necessary, and the known distance is used in the following case.

The signal of the third output terminal of the receiver portion 10B is transmitted to the time gate portion 21. The time gate is provided for allowing the first and the second echo from the reference reflecting surface 20 to selectively pass therethrough. Accordingly, the times to open and to close the gate are determined on the basis of the approximated measured value of the distance. When the distance between the probe 6B and the reference reflecting surface 20 is already known, it is determined using the known distance.

The open-state continuation time is determined on the basis of the information on the known continuation time width of the first and the second transmission signal, and information on the known continuation time width of the first and the second echo that is obtained in the signal processing procedure.

The first and the second echo selectively outputted from the time gate are transmitted to the delay portion 22.

The first and the second echo received by the probe 6A, which is associated with the object 8, are transmitted to the receiver portion 10A. The output signals from the first and the second output terminal of the receiver portion 10A are transmitted to the mixer portions 14A and 14B.

The first and the second echo are received by the probe 6B and the receiver portion 10B. The echoes are transferred through the third output terminal of the receiver portion 10B to the mixer portion 14A, and the delay portion 22. The echoes are transmitted from the first output terminal of the delay portion 22 to the mixer portion 14A. The output signal of the mixer portion 14A is transferred to the signal processor portion 11, through the filter portion 12A and the A/D convertor 13A.

The first and the second echo from the second output terminal of the delay portion 22 are transferred to the phase shifter portion 16A. The signal outputted from the phase shifter portion 16A is transferred to the phase inversion portion 23 where it is multiplied by −1. The signal from the phase inversion portion 23 is transferred to the mixer portion 14B. The output signal from the mixer portion 14B is transferred to the signal processor portion 11, by way of the filter portion 12B and the A/D convertor 13B.

The signal from the first output terminal of the delay portion 22 and the signal from the phase inversion portion 23 correspond to the first and the second reference signal of the first echo from the object 8 during the transmission repetitive period where the first transmission signal is transmitted.

The signal from the first output terminal of the delay portion 22 and the signal from the phase inversion portion 23 correspond to the first and the second reference signal of the second echo from the object 8 during the transmission repetitive period where the second transmission signal is transmitted.

The first echo from the reference reflecting surface 20 is delayed by the delay portion 22 such that the first echo from the object 8 overlaps with the first echo from the reference reflecting surface 20 in the mixer portions 14A and 14B. Similarly, the second echo from the reference reflecting surface 20 is delayed by the delay portion 22 such that the second echo from the object 8 overlaps with the second echo from the reference reflecting surface 20 in the mixer portions 14A and 14B.

Check as to whether or not the first echo from the object 8 overlaps with the first echo from the reference reflecting surface 20 and whether or not the second echo from the object 8 overlaps with the second echo from the reference reflecting surface 20 is made in the signal processor portion 11. To check, the signal processor portion 11 squares the output signals of the A/D convertors 13A and 13B and adds them together, and checks whether or not the addition result (function of time) is larger than a threshold value. If it is smaller than the threshold value, the delay time of the delay portion 22 is controlled by the signal from the controller portion 3 so that it is increased above the threshold value. When the distance between the object 8 and the reference reflecting surface 20 is already known, the delay time is determined using the known distance.

The first echo from the object 8 is processed in the following manner in the signal processor portion 11. The signal processor portion 11 obtains the complex amplitudes while the signal coming through the route of the mixer portion 14A, the filter portion 12A, and the A/D convertor 13A, is handled as the real part, and a signal coming through the route of the mixer portion 14B, the filter portion 12B, and the A/D convertor 13B is handled as an imaginary part. The signal processor portion 11 extracts the phase of the complex amplitude, and obtains the envelope from the amplitudes. The phase thus obtained corresponds to $\theta_{1o} - \theta_{1r} = -2\omega_1(Lo-Lr)/V$ in the 19th embodiment.

Similarly, the second echo from the object 8 is processed in the following manner in the signal processor portion 11. The signal processor portion 11 obtains the complex amplitudes while the signal coming through the route of the mixer portion 14A, the filter portion 12A, and the A/D convertor 13A, is handled as the real part, and a signal coming through the route of the mixer portion 14B, the filter portion 12B, and the A/D convertor 13B is handled as an imaginary part. The signal processor portion 11 extracts the phase of the complex amplitude, and obtains the envelope from the amplitudes. The phase thus obtained corresponds to $\theta_{2o} - \theta_{2r} = -2\omega_2(Lo-Lr)/V$ in the 19th embodiment.

Thus, the distance between the object 8 and the reference reflecting surface 20, (Lo−Lr), is obtained in the procedure as in the 19th embodiment, using the above information.

The operations and the useful effects by the operations of the 20th embodiment will be described. In the 20th embodiment, where the propagating path of the ultrasonic pulse between the reference reflecting surface 20 and the probe 6B and the propagating path of the ultrasonic pulse between the object 8 and the probe 6A are located within a spatial area where the variation is considered to be uniform when viewed locally, if the ambient condition variations with respect to time are quick, the phase variation is equally superposed on the phase $\theta_{1o}$ and the phase $\theta_{1r}$. The same thing is true for the phases $\theta_{2o}$ and $\theta_{2r}$.

The distance from the reference reflecting surface 20 to the object 8 is computed by using the differences $\theta_{1o} - \theta_{1r}$ and $\theta_{2o} - \theta_{2r}$. Accordingly, the above phase variations are neutralized in the difference phases, $\theta_{1o} - \theta_{1r}$ and $\theta_{2o} - \theta_{2r}$. Accordingly, as in the 19th embodiment, a measuring error caused the ambient condition variation is reduced.

In the 20th embodiment, the multiplying operation for detecting the phase is carried out in the mixer portions 14A to 14D. If the frequency of the ultrasonic wave is high, the useful effects as in the third embodiment are obtained.

21st Embodiment

Figure 32:
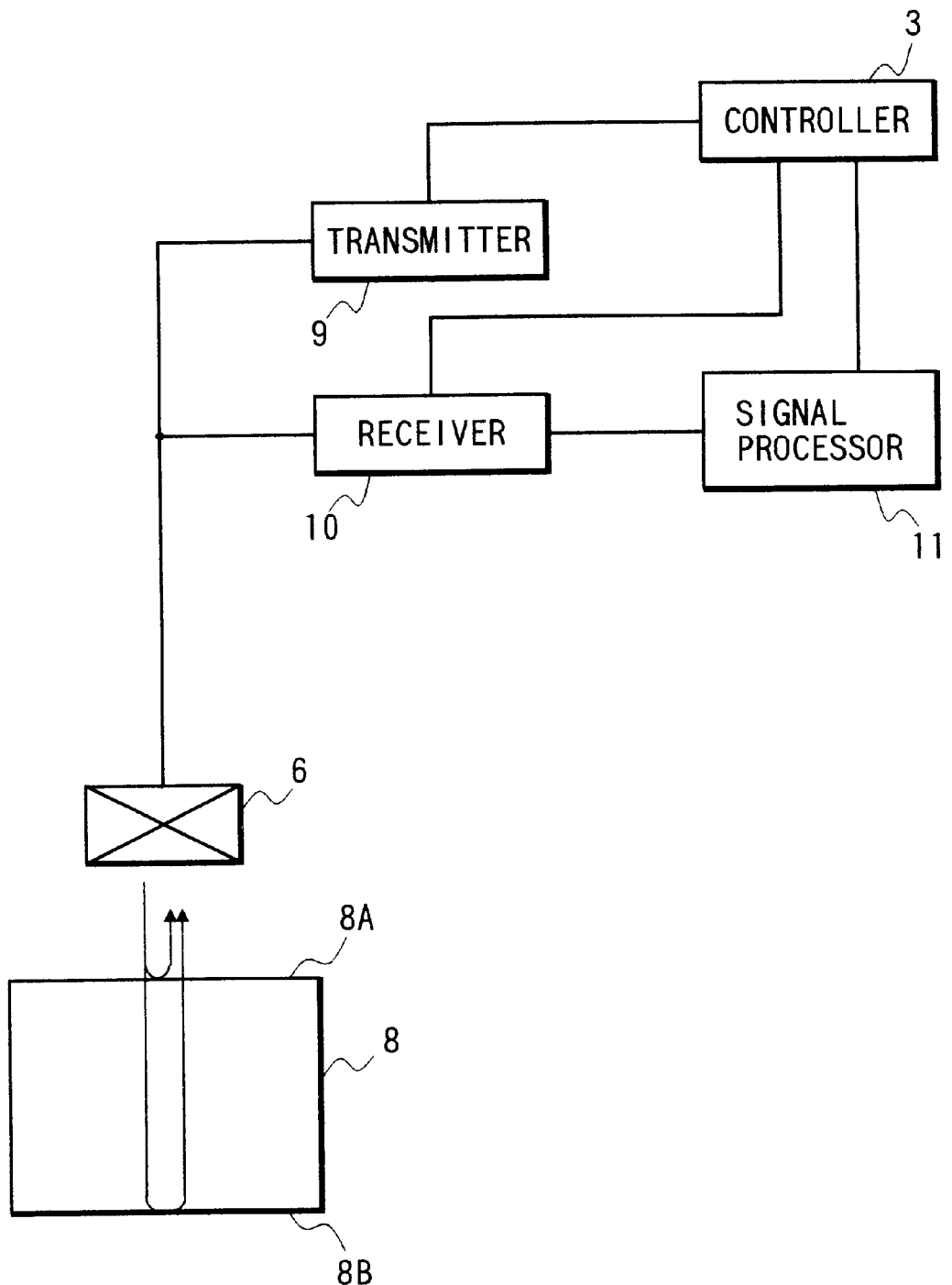
FIG. 32 shows a block diagram showing the arrangement of an ultrasonic distance measuring device according to a 21st embodiment of the present invention.

The 21st embodiment of the present invention will be described with reference to FIG. 32. FIG. 32 is a block diagram showing the arrangement of an ultrasonic distance measuring device according to a 21st embodiment of the present invention. In the figure, reference numeral 8 designates an object located in the air or the water, viz., in the ultrasonic wave propagating medium. The object 8 is also the ultrasonic wave propagating medium. 8A designates the top surface of the object 8 and 8B, the bottom surface. The remaining arrangement of the 21st embodiment is substantially the same as that of the first embodiment.

The operation of the 21st embodiment will be described. In the 21st embodiment, the ultrasonic pulse transmitted from the probe 6 is reflected by the top surface 8A of the object 8, and the reflected ultrasonic pulse is received again by the probe 6, in the form of an echo (referred to as the top echo). Part of the ultrasonic pulse passes through the object 8. The ultrasonic pulse passes through the object 8 and reaches the bottom surface 8B. The ultrasonic pulse is reflected by the bottom surface 8B and received by the probe 6, in the form of an echo (referred to as a bottom echo). The top echo and the bottom echo are received at different time points. In the signal processor portion 11, the first and the second echo of each of the top echo and the bottom echo are selectively picked up by the time gate, and processed in the signal processing procedure as in the first embodiment, to thereby obtain a distance $L_S$ between the probe 6 and the top surface 8A of the object 8 and a distance $L_B$ between the probe 6 and the bottom surface 8B of the object 8.

To obtain the distance $L_B$ between the probe 6 and the bottom surface 8B, the fact that a sonic speed Vo in the object is different from a sonic speed Va in the air as the ultrasonic wave propagating medium must be taken into consideration. The phase $\theta_1$ obtained by signal processing the first echo for the bottom surface 8B is given by the following equation (15)

$$\theta_1 = -2Ls\omega_1/Va - 2(L_B-L_S)\omega_1/Vo + \phi_1 - \psi_1 + 2n\pi \qquad (15)$$

The phase $\theta_2$ obtained by signal processing the second echo from the bottom surface 8B is given by: $\theta_2 = -2Ls\omega_2/Va - 2(L_B-L_S)\omega_2/Vo + \phi_2 - \psi_2 + 2m\pi$. The first terms in the right sides of the above equations of the phases $\theta_1$ and $\theta_2$ are obtained from the first and the second echoes from the top surface 8A. Accordingly, if these first terms indicate fixed phases, what are added to $\phi_1$ and $\phi_2$ are new $\phi_1$ and $\phi_2$, and the same procedure as in the first embodiment is carried out, to thereby obtain the thickness $(L_B-L_S)$ of the object 8.

In a state that the distance $L_S$ is zero, viz., the probe 6 is placed on the object 8, the thickness of the object can be measured using only the bottom echo, as described above.

In the 21st embodiment, the thickness $(L_B-L_S)$ of the object 8 can be measured at high accuracy.

In the descriptions thus far made, the process of deriving the distance L is qualitatively described. More specific description on the process of deriving or determining the distance L will be given hereinafter.

22nd Embodiment

For the first or the tenth embodiment, the overall signal processing procedure thereof has been described with reference to FIGS. 6 to 8 or FIGS. 20 and 21. In the 22nd embodiment and subsequent ones, the methods of deriving the distance L will be described in more detail.

Figure 33:
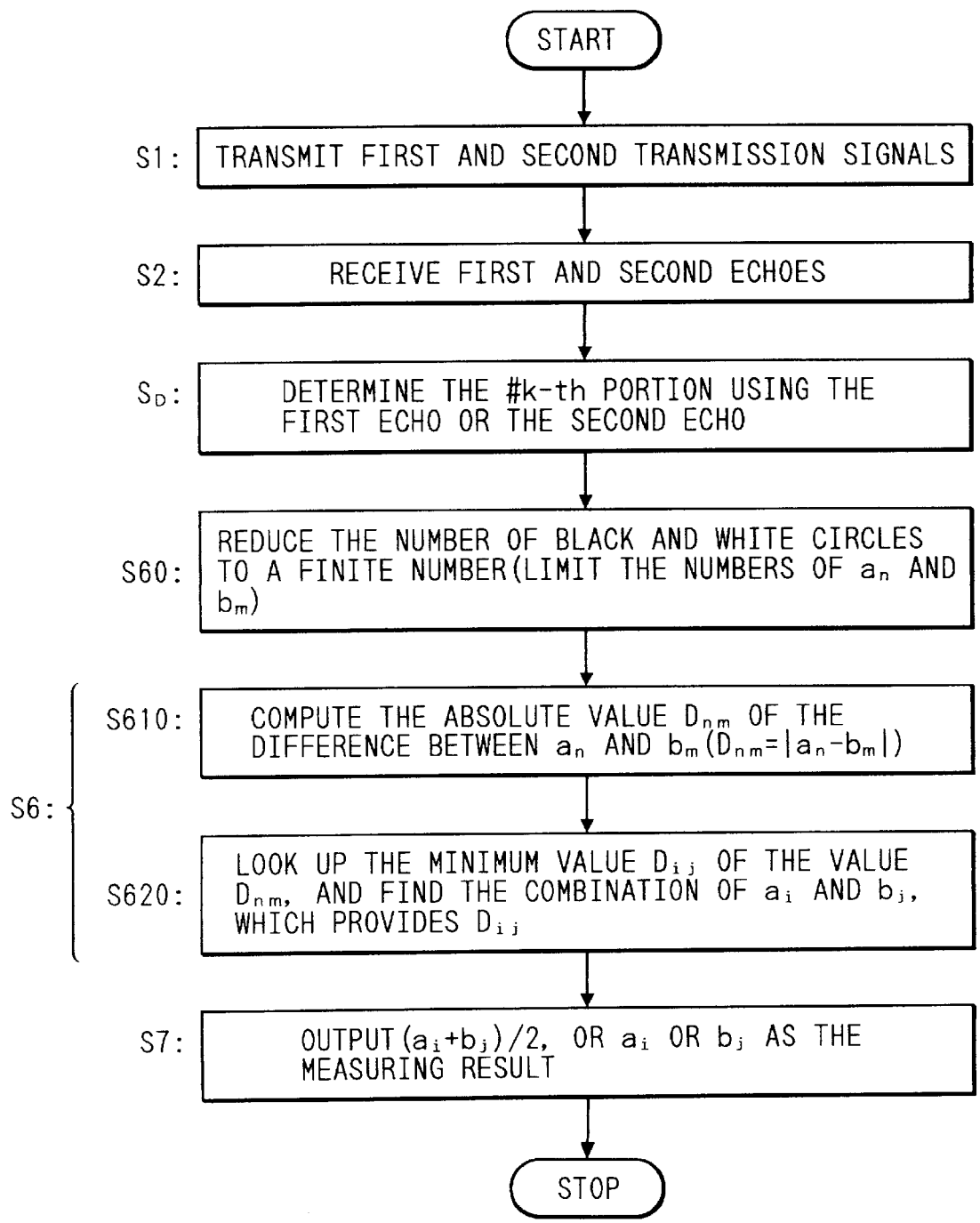
FIG. 33 shows a flowchart showing a signal processing process in the 22nd embodiment of the present invention.

A first distance deriving method as a 22nd embodiment of the present invention will be described with reference to FIG. 33. In FIG. 33, steps S1, S2, $S_D$, S60, S6, and S7 correspond to the steps S1, S2, $S_D$, S60, S6, and S7 in FIGS. 20 and 21. This is correspondingly applied to flowcharts of FIGS. 34 to 36, and 41. In FIG. 33, the steps S11 and S12 in FIG. 6 are represented by a single step S1. The step S2 similarly represents a plural number of the steps. The same thing is true for the flowcharts of the signal processing procedure in the embodiments to be described later. As shown in FIG. 33, by using information of the amplitude or the envelope of the first echo, information of the amplitude or the envelope of the second echo, or the combination of these pieces of information, in the procedure described referring to FIGS. 3, 4 and 5, of which of the periods $q\pi V/\Delta\omega$ contains a desired distance, viz., the # k-th portion, is determined in the step $S_D$.

On the basis of the determination, in a step S60 in FIG. 33, the number of white and black circles shown in FIG. 3 or 4 is finite. That is, the operation of the step S60 in FIG. 7 or 8 is performed in the step S60 in FIG. 33. Distances of white circles and black circles are determined. These distances are given by $a_n$ (n=1, 2, . . . , N) and $b_m$ (m =1, 2, . . . , M)

where N and M are natural numbers.

As shown in a step S610 in FIG. 33, the absolute value of the difference between $a_n$ and $b_m$ is computed. This value is denoted as $D_{nm}$.

Then, as shown in the step S620 in FIG. 33, the minimum value of the values $D_{nm}$ is looked up. This minimum value is denoted as $D_{ij}$. The combination of $a_n$ and $b_m$, which provides the minimum value $D_{ij}$, is obtained. This combination is expressed as (ai, bj).

When $a_n = a_i$ and $b_m = b_j$, $D_{nm} = D_{ij}$.

In the step S7 in FIG. 33, an average value of the two distances $a_i$ and $b_j$, $(a_i+b_j)/2$, is outputted as the result of the distance measurement. Alternatively, $a_i$ or $b_j$ is outputted as the result of the distance measurement.

To output the distance measurement result is to output a true distance. This is true for other embodiments.

In FIG. 33, the computing operation and the signal processing operation in the step $S_D$ to S7 is carried out in the signal processor portion 11 as in the case of FIGS. 6 to 8.

The first distance deriving method as the 22nd embodiment is capable of measuring the distance even when the value $D_{nm}$, which should be zero, cannot be set to zero.

23rd Embodiment

Figure 34:
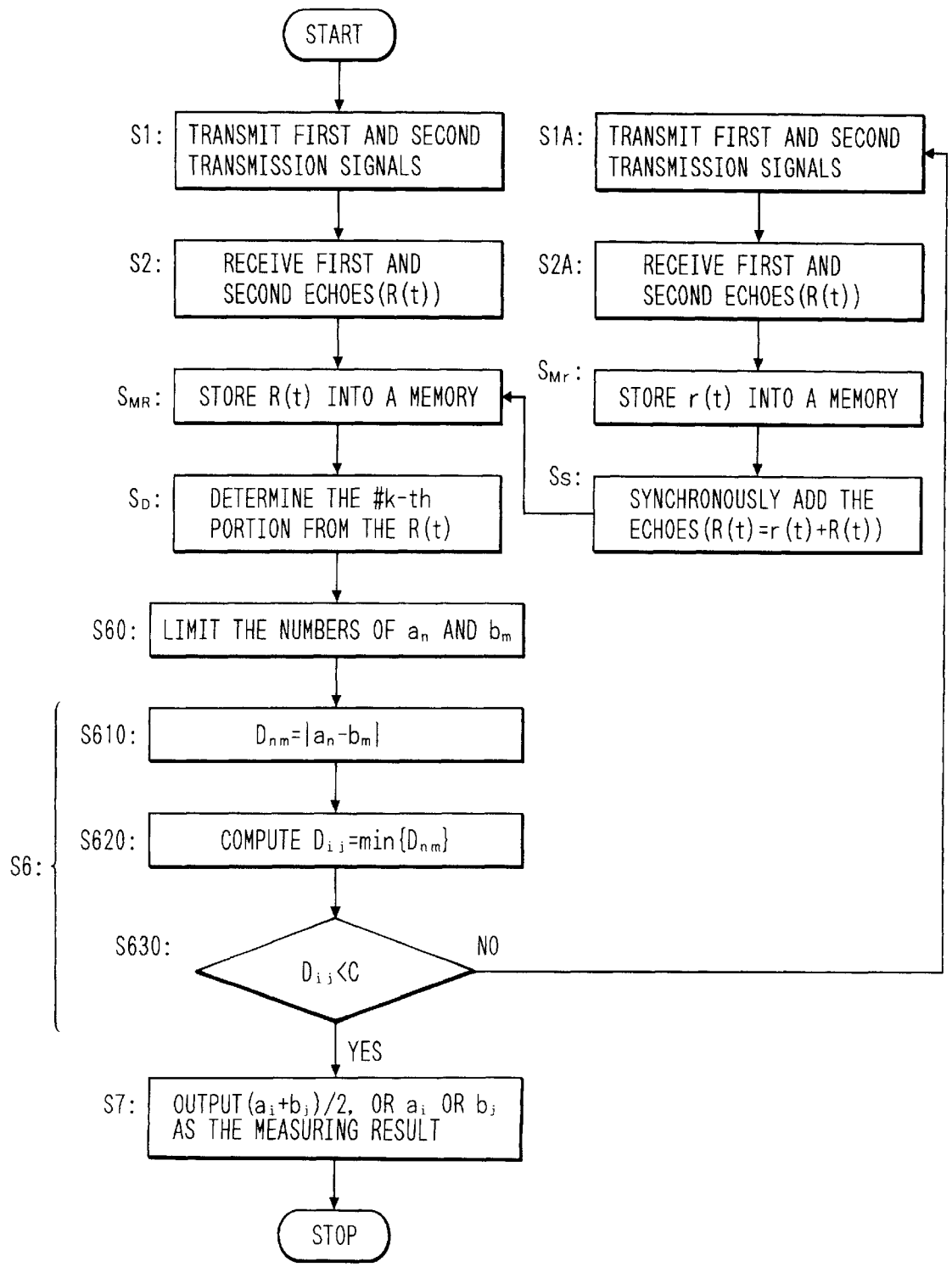
FIG. 34 shows a flowchart showing a signal processing process in the 23rd embodiment of the present invention.

A second distance deriving method according to a 23rd embodiment of the present invention will be described with reference to FIG. 34. FIG. 34 is a flowchart showing a signal processing process in the 23rd embodiment of the present invention.

In the 23rd embodiment, a step S630 of determining a tolerable error is carried out in addition to the process of the 22nd embodiment.

The second distance deriving method will be described in detail. As shown in FIG. 34, the # k-th portion is determined in the step $S_D$. In this # k-th portion, distances $a_n$ (n=1, 2, . . . , N) and $b_m$ (m=1, 2, . . . , M) of the black and white circles are obtained. Further, in the same procedure as of the first distance deriving method, $D_{nm}$ (n=1, 2, . . . , N; m=1, 2, . . . , M) is computed in the step S610. The minimum value $D_{ij}$ of the $D_{nm}$, and the combination (ai, bj) providing the minimum value are computed in the step S620.

In this second distance deriving method, a tolerable error range is previously set. This tolerable value is expressed as C. In the second distance deriving method, as shown in FIG. 34, the step S630 determines whether or not the minimum value $D_{ij}$ is smaller than the tolerable value C.

If the minimum value $D_{ij}$ is smaller than the tolerable value C, as in the first distance deriving method, an average value of the two distances $a_i$ and $b_j$, $(a_i+b_j)/2$, is outputted as the result of the distance measurement. Alternatively, $a_i$ or $b_i$ is outputted as the result of the distance measurement.

The process of the step S60 corresponds to the process to reduce the number of distance candidates in the candidate-contained portion.

When the minimum value $D_{ij}$ is not within the tolerable value C, the signal processing process goes through the steps S1A, S2A, SMr, and SS, and carries out the synchronous addition process and the synchronous addition/averaging process on the first and the second echo or the averaging/addition process on the phases of the first and the second echo. On the basis of the information on the first and the second echo that are obtained by carrying out the synchronous addition process and the synchronous addition/averaging process on the first and the second echo or the averaging/addition process on the phases of the first and the second echo, the number of averaging operations is increased and the above procedure is repeated. This process is repeated till it falls within the tolerable error range. As the result of increasing the number of averaging operations, the adverse effect caused by the ambient condition variation is reduced to a certain extent. Also when the difference between the minimum value $D_{ij}$ and the secondly small $D_{nm}$ is small, the measurement process where the number of the averaging operations is increased is repeated till a given difference is reached.

In the second distance deriving method, for the storing steps SMR and SMr in FIG. 34, R(t) and r(t) are stored into the first memory in the signal processor portion 11. When the answer to the step S630 is "NO", a signal representative of "NO" is transferred from the signal processor portion 11 to the controller portion 3, so as to execute the step S1A. In response to this, the transmitter portion 9 executes the step S1A, and the steps S2A, SMr, SS, and SMR are successively executed.

In the second distance deriving method, the tolerable value C may be set to a proper value. Where a high measuring accuracy is required, the tolerable value C is set to a large value. In this case, the number of averaging operations is reduced, to thereby improving the measuring speed.

The second distance deriving method has the useful effects comparable with those of the first distance deriving method. Since the addition/averaging process is used in the second distance deriving method, the adverse effect caused by the ambient condition variation is reduced, so that the distance can be measured at high accuracy. When the tolerable value C is properly set depending on ambient conditions and the object, the measuring speed is improved.

24th Embodiment

Figure 35:
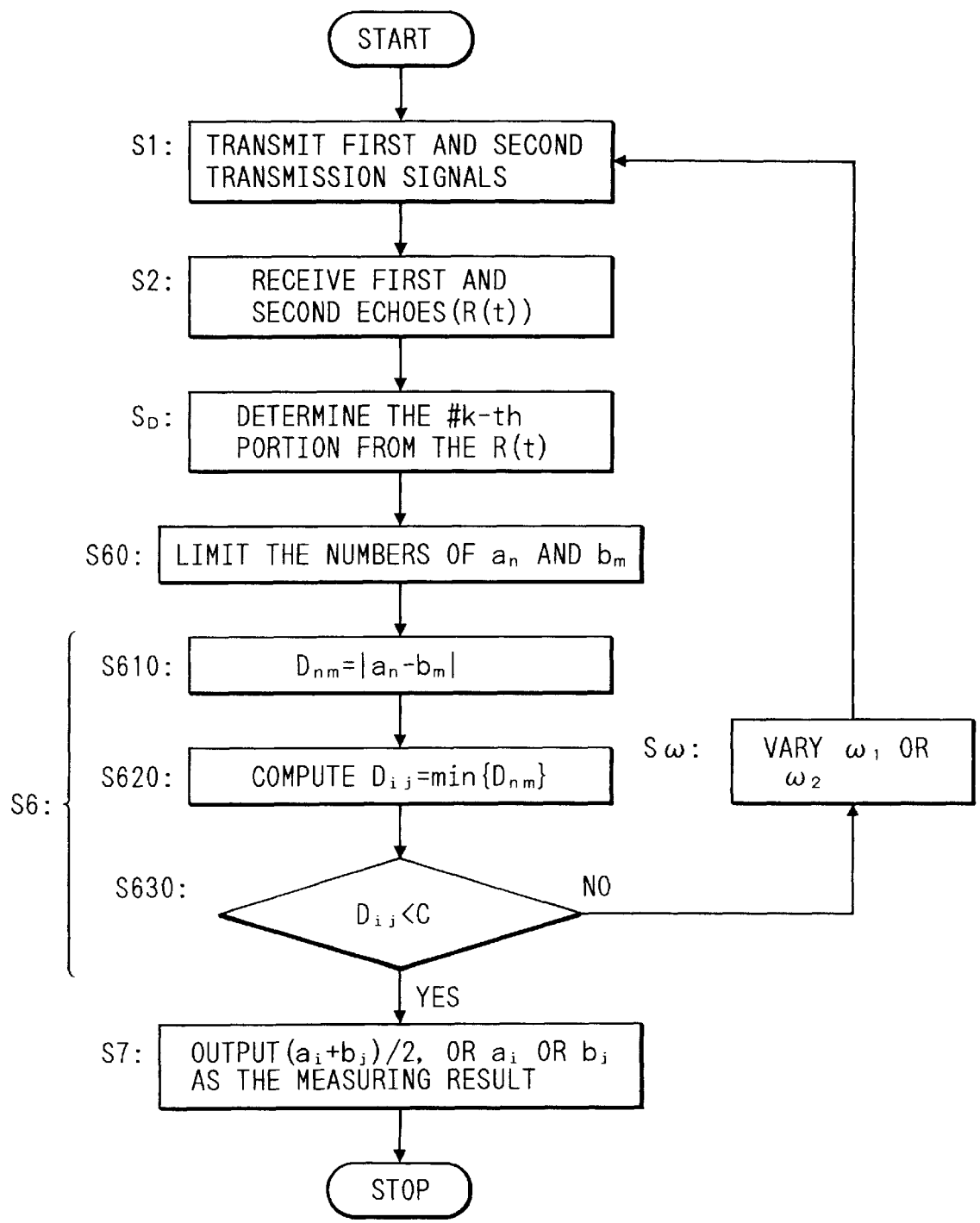
FIG. 35 shows a flowchart showing a signal processing process in the 24th embodiment of the present invention.

A third distance deriving method according to the 24th embodiment of the present invention will be described with reference to FIG. 35. FIG. 35 shows a flowchart showing a procedure for determining an indeterminacy of the phase as by the first distance deriving method.

The third distance deriving method will be described in detail. As shown in FIG. 35, in the procedure as of the first distance deriving method, the # k-th portion is determined in the step $S_D$. In this # k-th portion, distances $a_n$ (n=1, 2, ..., N) and $b_m$ (m=1, 2, ..., M) of the black and white circles are obtained. Further, in the same procedure as of the second distance deriving method, $D_{nm}$ (n=1, 2, ..., N; m=1, 2, ..., M) is computed in the step S610. The minimum value $D_{ij}$ of the $D_{nm}$, and the combination (ai, bj) providing the minimum value are computed.

In the third distance deriving method, a tolerable error range C is previously set as in the second distance deriving method. If the minimum value $D_{ij}$ is smaller than the tolerable value C (step S630), an average value of the two distances ai and bj, $(a_i+b_j)/2$, is outputted as the result of the distance measurement. Alternatively, $a_i$ or $b_j$ is outputted as the result of the distance measurement.

When the minimum value $D_{ij}$ is not within the tolerable value C, the controller portion 3 produces a control signal for varying the angular frequency $\omega_1$ or $\omega_2$ in the step $S\omega$. On the basis of this, one of the angular frequency $\omega_1$ and $\omega_2$ is fixed, while the other is shifted from the original value. The transmission repetitive period Tγ of which the frequencies are thus set are transmitted, and the same procedure as of the first embodiment is repeated again. This angular frequency scan is repeated till the minimum value $D_{ij}$ becomes below the tolerable value C. Although not shown in FIG. 35, also when the difference between the minimum value $D_{ij}$ and the secondly small $D_{nm}$, the measurement by the angular frequency scan is repeated till a given difference is reached.

The step S630 is executed in the signal processor portion 11. If the answer to the step is "NO", a signal representative of "NO" is transferred to the controller portion 3. In response to the signal, the controller portion 3 sends a control signal for changing the angular frequency to the transmitter portion 9.

The third distance deriving method has the useful effects as of the first distance deriving method, and further of the first embodiment since the angular frequency scan is carried out.

25th Embodiment

A fourth distance deriving method according to the 25th embodiment of the present invention will be described. The 25th embodiment concerns the procedure of the angular frequency scan in the third distance deriving method.

In the fourth distance deriving method, in the same procedure as of the first distance deriving method, the minimum value $D_{ij}$ of the $D_{nm}$ is computed, the result is compared with the tolerable value C, and if the minimum value $D_{ij}$ is not within the tolerable value C, the angular frequency is scanned in the following manner.

The angular frequency $\omega_1$ is fixed. In the first measurement, the angular frequency $\omega_2$ is set so as to reduce the difference $\Delta\omega$ between the two angular frequencies. In the second measurement, it is set so as to increase the difference $\Delta\omega$ to be larger than that in the first measurement. In the third measurement, it is set so as to increase the difference $\Delta\omega$ to be larger than that in the second measurement. Thus, the angular frequency $\omega_2$ is set such that the difference $\Delta\omega$ in the present measurement is larger than that in the previous measurement. Accordingly, the difference $\Delta\omega$ increases with increase of the number of the measurements.

The useful effects of the fourth distance deriving method will be described. As described in connection with the first distance deriving method, in FIG. 4, the period at which the specific circle combinations appear is inversely proportional to the difference $\Delta\omega$. Accordingly, as the difference $\Delta\omega$ is smaller, the period is longer. As a result, it is easy to determine the # k-th portion in the first distance deriving method.

In this case, the difference between the inclinations of the two characteristic curves in FIG. 4 is small, and it is difficult to detect the combination of $a_n$ and $b_m$ which provides the minimum value $D_{ij}$.

Where the difference $\Delta\omega$ is large, the period is short, it is difficult to determine the # k-th portion in the first distance deriving method.

In this case, the difference between the inclinations of the two characteristic curves in FIG. 4 is large, and it is easy to detect the combination of $a_n$ and $b_m$ which provides the minimum value $D_{ij}$.

In the fourth distance deriving method, the scan is performed in such a manner that the difference $\Delta\omega$ is set to a small at the initial stage, and then gradually increased. Accordingly, at the initial stage, the # k-th portion is roughly determined. Since the difference $\Delta\omega$ is gradually increased, it is gradually limited in the rough portion determined in the previous measurement. Further, the detection of the combination of $a_n$ and $b_m$ which provides the minimum value $D_{ij}$ is easy gradually.

In the above-mentioned embodiment, one of the angular frequencies is fixed while the other is scanned. For some types of band-pass characteristics of the probes, it is frequently advantageous to scan both the angular frequencies. In a case where the band-pass characteristic curve of the probe is shaped to be symmetrical with respect to the center frequency, located between the high frequency region and the low frequency region, one of the angular frequencies is set in the low frequency region, while the other, in the high frequency region. Further, the differences between one of the two angular frequencies and the center frequency of the probe and between the other angular frequency and the center frequency, are set so that these are equal to each other. Under the setting conditions, if the scan is made so that the difference between the two angular frequencies is gradually increased, the difference of the sensitivities of the receiving echoes corresponding to the two angular frequencies may be kept small. Therefore, little deviation of the respective portions from their ideal operations is caused.

26th Embodiment

Figure 36:
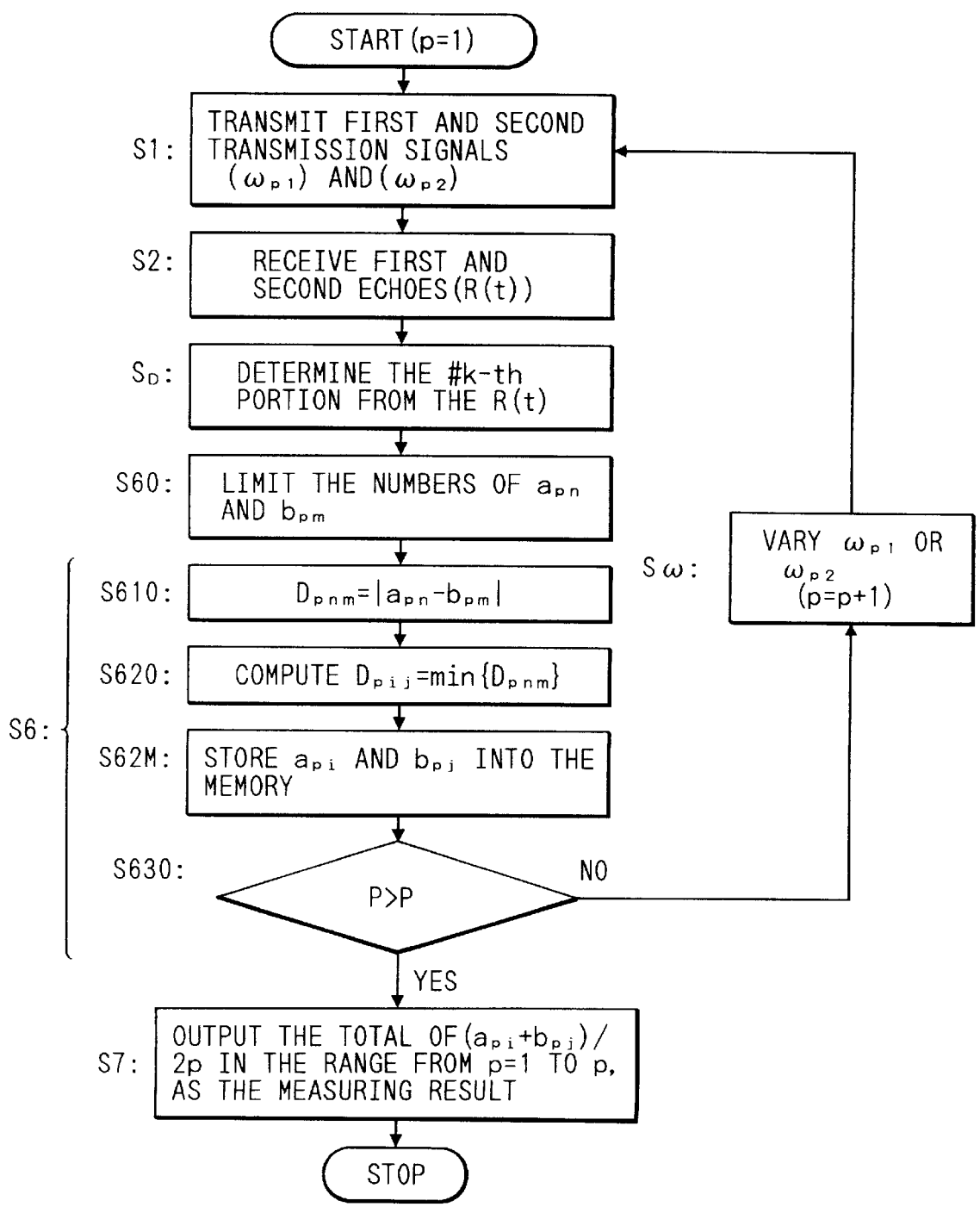
FIG. 36 shows a flowchart showing a signal processing process in the 26th embodiment of the present invention.

A fifth distance deriving method according to a fifth embodiment of the present invention will be described with reference to FIG. 36. FIG. 36 shows a flowchart showing a procedure for determining an indeterminacy of the phase as by the first distance deriving method.

In the third and the fourth distance deriving method, either or both of the two angular frequencies are scanned. In one measurement, only the phase information on the two angular frequencies, which are used in the measurement, are used. In the fifth embodiment, the measurement result is stored every measurement. By using the results of a plural number of measurements, the measuring accuracy is further improved.

The fifth distance deriving method will be described in detail. As shown in FIG. 36, in the first measurement, by using a transmission signal corresponding to the angular frequency $\omega_1$ and another transmission signal corresponding to the angular frequency $\omega_2$, in the same procedure as of the second distance deriving method, the combination of $a_n$ and $b_m$ (expressed as $a_{1i}$ and $b_{1j}$) which provides the minimum value $D_{ij}$ is detected and stored into the memory. Also in the second measurement in which the frequency is scanned, the combination of $a_{2i}$ and $b_{2j}$ which provides the minimum value $D_{ij}$ is detected. This detection process is repeated P times. The result of the P-th detection is represented by $a_{pi}$ and $b_{pj}$. After the P-th measurement is completed, the distance is computed by $$\Sigma(a_{pi}+b_{pj})/(2P)$$

(summed in the range from 1 to P)

In the fifth distance deriving method, in the step $S\omega$ in FIG. 36, the controller portion 3 is used for the operation control as in the third distance deriving method. The fifth distance deriving method is substantially equal to that of FIG. 35 in that the controller portion 3 sends a control signal to the transmitter portion 9 in response to the signal representative of "NO", that is the answer to the control signal step S630.

In the operation of the step S62M, $a_{pi}$ and $b_{pj}$ are stored into the memory in the signal processor portion 11.

The useful effects of the fifth distance deriving method will be described. In the third and the fourth distance deriving method, if the number of measurements is increased, the minimum value $D_{ij}$ is frequently out of the tolerable value C. In such a case, the tolerable range for the measuring error must be enlarged by increasing the tolerable error range. This leads to deterioration of the measuring accuracy. In the fifth distance deriving method, the distance is obtained by averaging the results obtained by using a plural number of angular frequencies. The averaging process used more improves the measuring accuracy than the third and the fourth distance deriving method.

27th Embodiment

Figure 37:
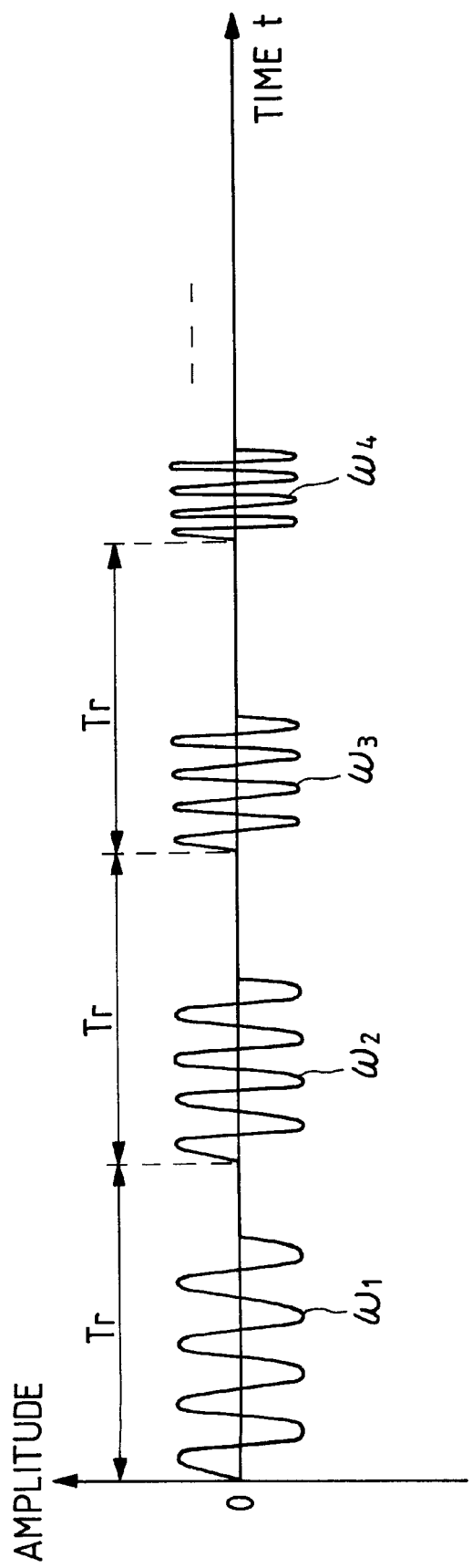
FIG. 37 shows a waveform diagram for explaining the operation of the 27th embodiment of the present invention.

The 27th embodiment of the present invention will be described with reference to FIG. 37. FIG. 37 is a waveform diagram showing transmission signals repeatedly transmitted. The 27th embodiment has substantially the same effects as of the 26th embodiment.

In the 27th embodiment, transmissions signals of angular frequencies $\omega_3, \omega_4, \ldots, \omega_p$ in addition to the transmission signals of the angular frequencies $\omega_1$ and $\omega_2$, are transmitted at the transmission repetitive periods $T\tau$ to the probe.

In response to those transmission signals, a plural number of echoes are received. These echo signals are processed in the procedure as in the 22nd embodiment, thereby to obtain the phases and the envelopes.

The phase of the angular frequency $\omega_p$ (p=1 to P) is expressed as $\theta_p$ (p=1 to P).

By using information on the amplitude or the envelope of the echo of the angular frequency $\omega_p$ (p=1 to P), the # k-th portion is determined as in the 22nd embodiment. In this case, only information on one angular frequency may be used or information on a plural number of angular frequencies may be used for synthetically determining the # k-th portion. As in the 25th embodiment, two large angular frequency differences are first selected, and large portions are determined. Then, the combination of the small angular frequency differences is progressively selected, and the portions are limited to small portions. The 27th embodiment has the useful effects as of the 25th embodiment.

Two phases are selected from among the phases $\theta_p$. In the same procedure as of the first embodiment, the combination of $a_n$ and $b_m$ which provides the minimum value $D_{ij}$ is detected and stored. There are a plural number of the combinations of two phases from among a p number of phases $\theta_p$ (p=1 to P). The above operation is applied to those combinations. A plural number of results obtained by the operation are averaged as in the 26th embodiment, and the result is outputted as the final result. As a result, the 27th embodiment has the useful effects as of the 26th embodiment.

The above operation may be applied to all of the combinations or a preset number of combinations. In the latter case, in the plural number of results to be averaged, the minimum values $D_{ij}$ corresponding to them are simultaneously obtained. Of those minimum values $D_{ij}$, those values larger than a preset value are not averaged, while those values smaller than the preset value are picked up and averaged. A further improvement of the measuring accuracy is ensured.

As in the 25th embodiment, the above operation is first performed for the combination of the large angular frequency differences and then for the combination of the small angular frequency differences.

28th Embodiment

Figure 38:
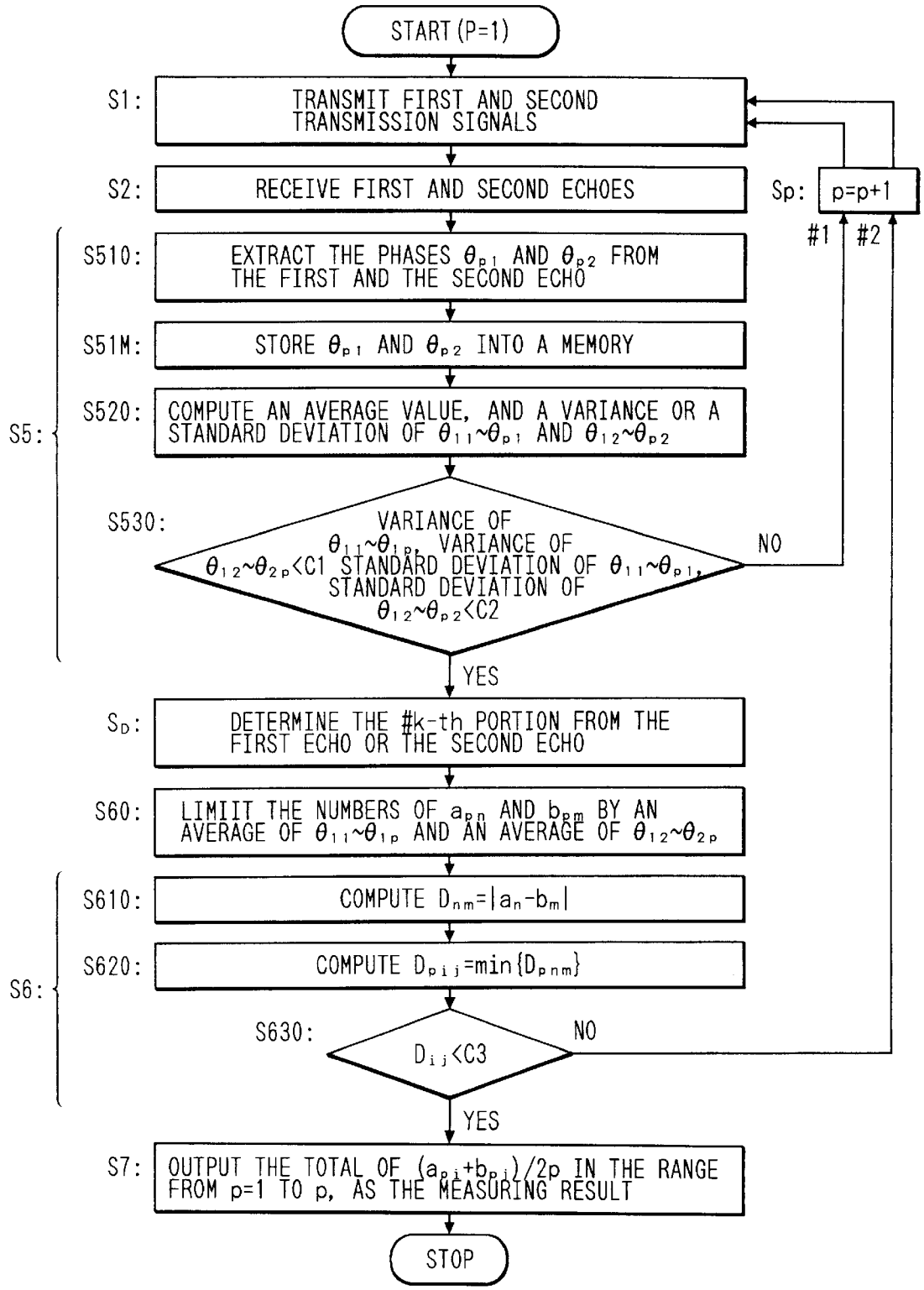
FIG. 38 shows a flowchart showing the signal processing process in the 28th embodiment of the present invention.

A sixth distance deriving method according to a 28th embodiment of the present invention will be described with reference to FIG. 38. FIG. 38 is a flowchart showing a signal processing procedure for explaining the 28th embodiment.

In the 28th embodiment, the present invention is applied to the measurement of a shape of an object. In the 28th embodiment, a probe is spatially moved to scan an object to be visualized. At a point in a space, in a step S510, the phases $\theta_{p1}$ and $\theta_{p2}$ of the first and the second echo are obtained by applying the 22nd embodiment. At the same time, the amplitudes or the envelopes of the echo signals are obtained. The thus obtained phases $\theta_{p1}$ and $\theta_{p2}$ are stored into the memory of the signal processor portion 11, in a step S51M.

This procedural operation is repeated plural times. Every the procedural operation, an average, a variance, or a standard deviation of the results of the procedural operations thus far obtained till the previous procedural operation are computed. A step S530 checks whether or not the variance or the standard deviation thus obtained is within a preset tolerable range (variance range: C1, standard deviation range: C2). The control flows to the step $S_D$ or the step Sp depending on the answer YES and NO to the step S530. When the answer to the step S530 is YES, $D_{ij}$ is obtained in the same procedure as of the 23rd embodiment, using the average.

Then, the thus obtained $D_{ij}$ is compared with a preset tolerable error range C3 in a step S630. When $D_{ij}$ is larger than the tolerable error range, the transmission of the transmission signals are repeated and the above procedure is repeated. The repeated operation corresponds to the operation to increment the value P by one in the step Sp block.

As a matter of course, in repeating this, the average value and the variance or the standard deviation are calculated by additionally using the data obtained before the repeating. At a time point where the $D_{ij}$ goes below the tolerance value, in the procedure as of the 22nd embodiment, viz., in the step S7, the distance L is obtained and outputted. Then, the probe is spatially moved, the distance at a point is obtained in the above procedure, and outputted. This procedure is successively carried out within a given range while moving the probe for scan.

In the flowchart shown in FIG. 38, the operation in the step Sp corresponds to the transfer of the control signal for executing the repeating from the controller portion 3 to the transmitter portion 9. The signals representative of "NO" as the answer to the steps S530 and S630 are transferred from the signal processor portion 11 to the controller portion 3. In response to this, the controller portion 3 executes the operation of the step Sp, thereby to effect the control. It is executed as a sequence of operations from the step S5 to the step S7, in the signal processor portion 11.

The number of the repeating operations of a line with an arrow head with a mark #1 may be set to one time, and the number of the repeating operations of a line with an arrow head with a mark #2 may be set to plural times. Conversely, the number of the repeating operations of the #1 line may be set to plural times, and the number of the repeating operations of the #2 line may be set to one time. By so doing, the processing time for obtaining the results can be reduced.

In FIG. 38, when the variance or the standard deviation of the amplitudes or the envelopes fall within the tolerance value after a less number of repeating operations when comparing with the phases, the average value gained at that time point is stored. This is used as a value for the procedure to obtain $D_{nm}$. In the subsequent repeating operations, the values of the amplitudes or the envelope are removed from the processing procedure and there is no work to obtain them. Similarly, when the phase falls within the tolerance value, the average value is stored, and it is used as a value in the procedure to obtain $D_{nm}$. In the subsequent procedure, the phase value is removed from the signal processing procedure, and there is no work to obtain it. By so doing, the processing time is reduced.

The useful effects of the 28th embodiment and the operations causing them will be described. In the 28th embodiment, at the positions of the probes, the number of the repeating operations in the signal processing procedure shown in FIG. 38 may be adaptively changed in accordance with varying instantaneously varying ambient conditions. Accordingly, in visualizing an object in the measurement of an object shape, the measuring time is reduced, and hence the measurement is completed for a short time.

The case where the object is fixed, while the probe is moved for scan has been described. If required, such an arrangement is allowed in which the probe is fixed while the object is moved for scan. In this case, by using the same signal processing procedure as of the 28th embodiment, the useful effects of the 28th embodiment can be obtained.

29th Embodiment

Figure 39:
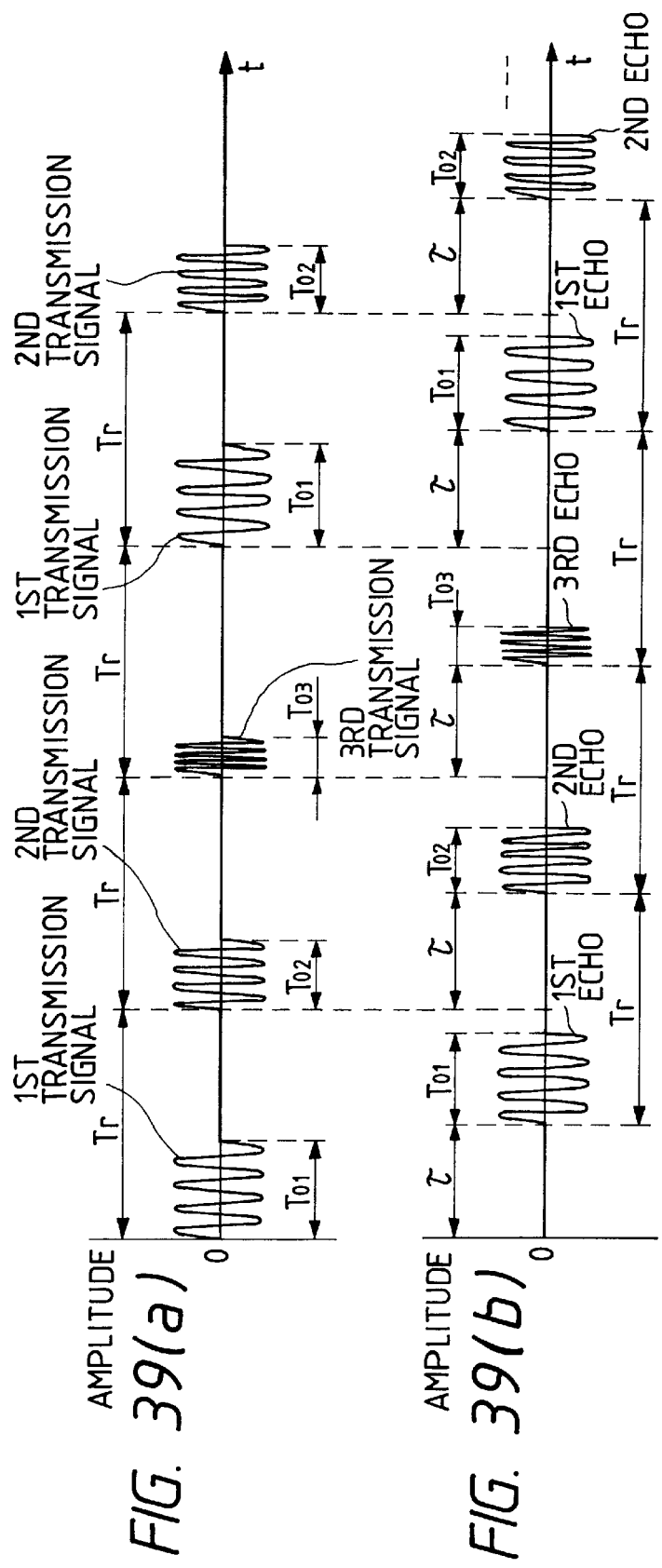
FIGS. 39(a) and 39(b) show waveform diagrams for explaining the operation of the 29th embodiment of the present invention.
Figure 40:
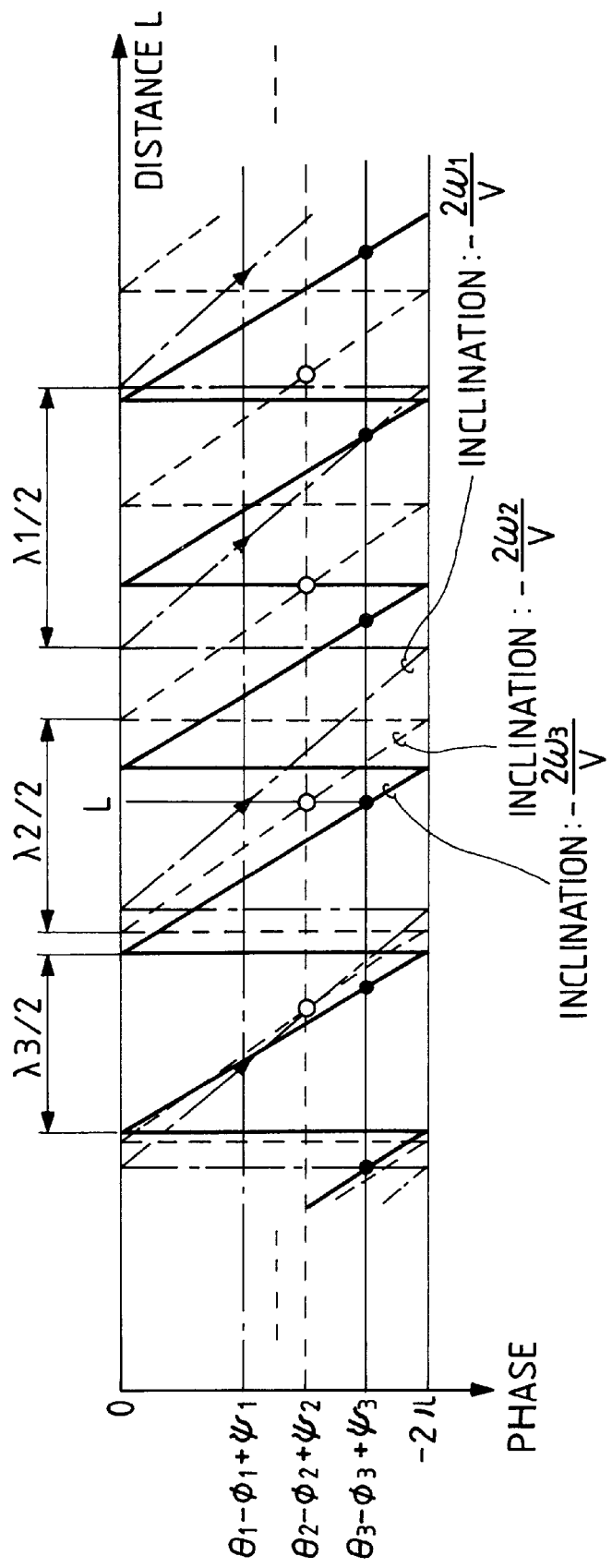
FIG. 40 shows a characteristic diagram for explaining the signal processing in the 29th embodiment of the present invention.
Figure 41:
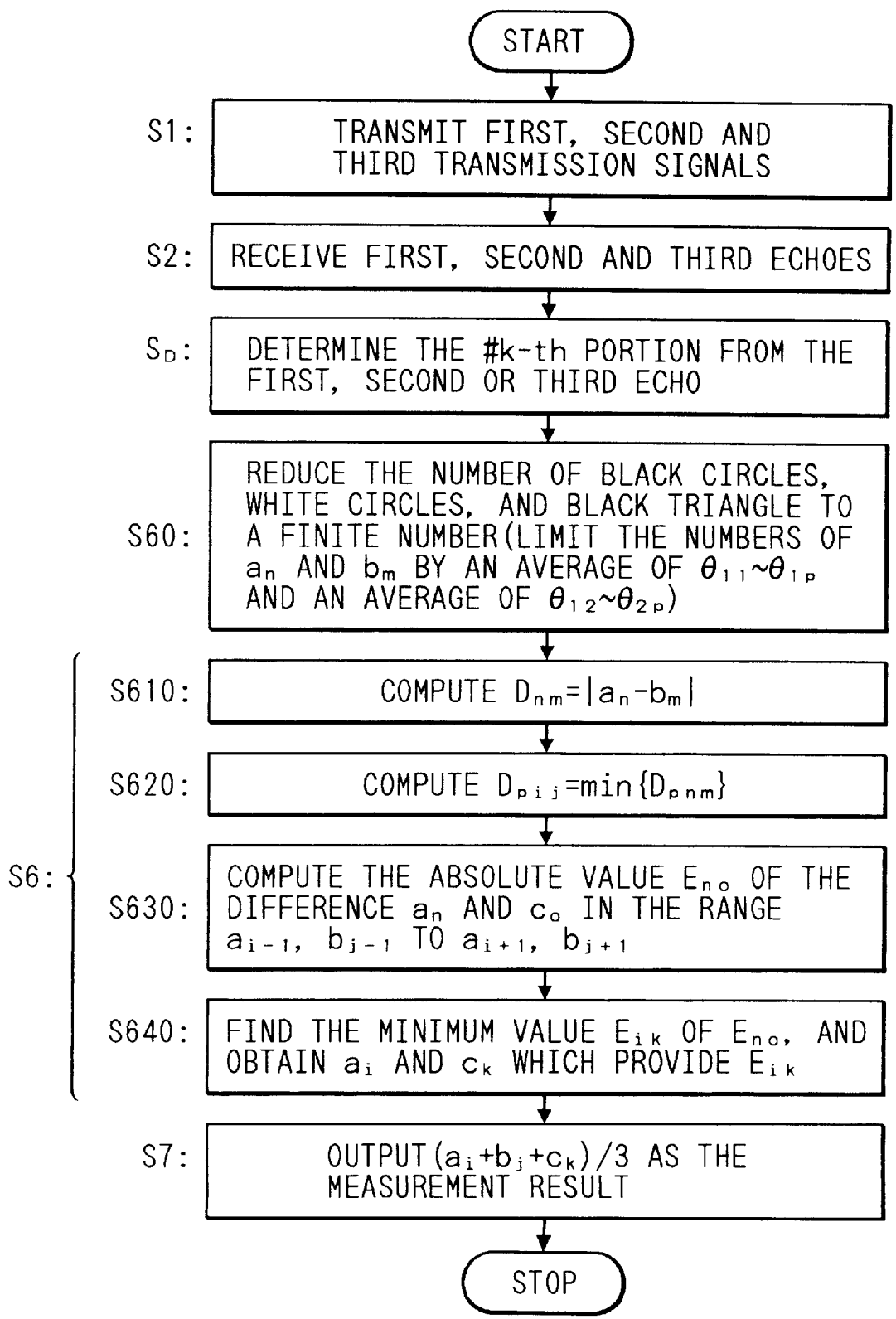
FIG. 41 shows a flowchart showing a signal processing process in the 29th embodiment of the present invention.
Figure 42:
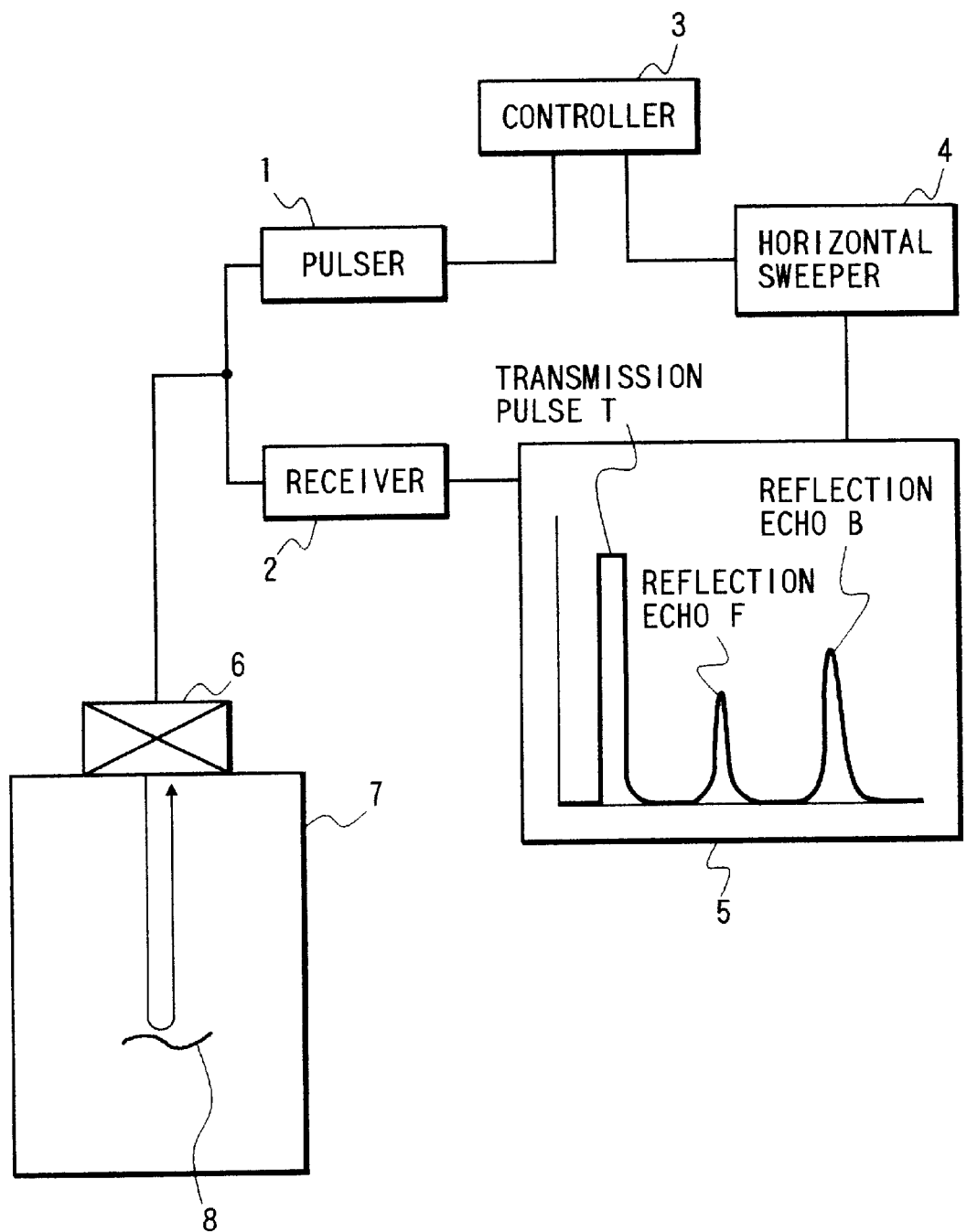
FIG. 42 shows a block diagram showing the arrangement of a conventional ultrasonic distance measuring device.
Figure 43A:
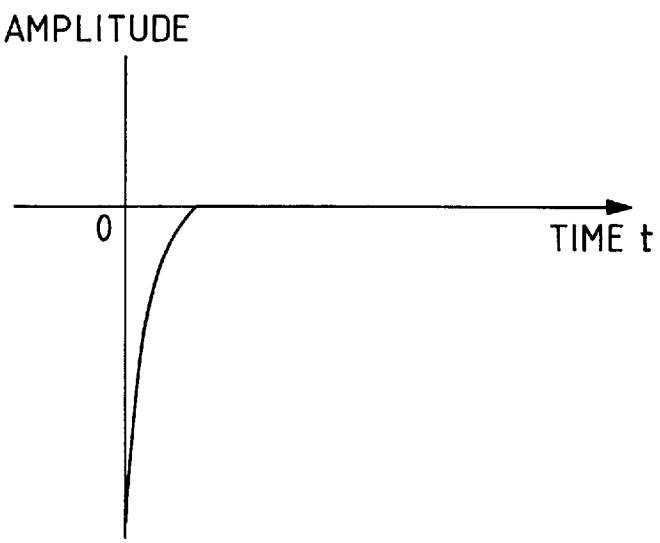
FIGS. 43(a) and 43(b) show waveform diagrams for explaining the operation of the conventional ultrasonic distance measuring device.
Figure 43B:
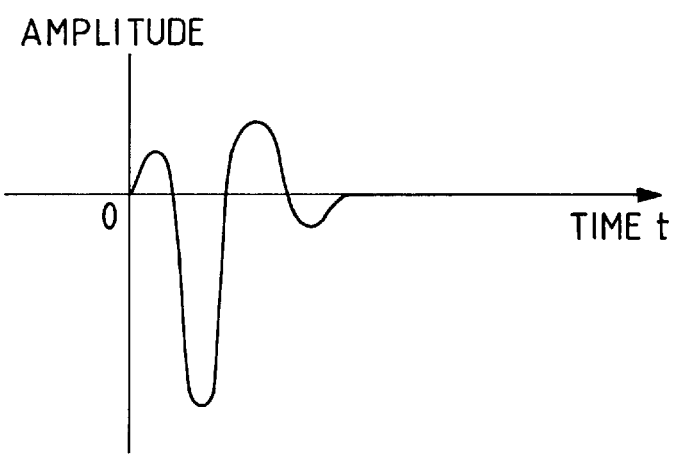
Figure 44:
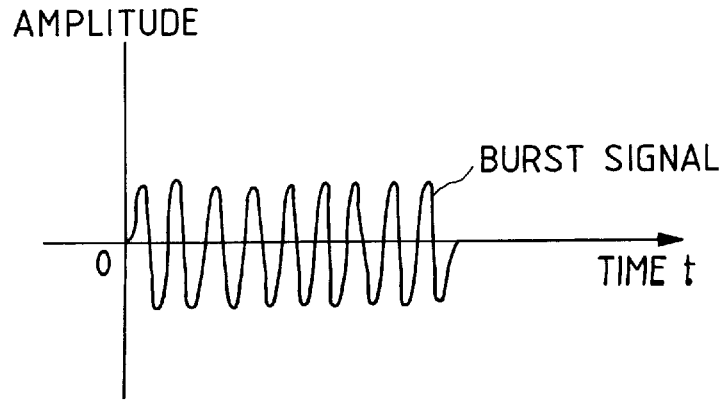
FIG. 44 shows a waveform diagram for explaining the operation of the conventional ultrasonic distance measuring device.

The 29th embodiment of the present invention will be described with reference to FIGS. 39, 40 and 41. The circuit arrangement of the 29th embodiment is the same as of the first embodiment. FIG. 39 is a waveform diagram for explaining the operation of the 29th embodiment. FIG. 39(a) shows a transmission signal for exciting the probe 6. FIG. 39(b) shows an echo reflected by an object 8. FIG. 40 is a characteristic diagram for explaining the signal processing process in the signal processor portion 11. FIG. 41 is a flowchart for explaining the signal processing process in the signal processor portion 11.

The operation of the 29th embodiment will be described. Transmission signals shown in FIG. 39(a) are transmitted from the transmitter portion 9 to the probe 6. As shown, the transmission signals are first and second transmission signals, and a burst signal of the carrier frequency $\omega_3$ (referred to as a third transmission signal). These first to third transmission signals are repeated at the transmission repetitive periods Tτ.

In the present embodiment, $\omega_1 < \omega_2 < \omega_3$.

The probe 6 is excited by the transmission signals shown in FIG. 39(a), and emits ultrasonic pulses toward the object 8. The ultrasonic pulses are reflected from the object 8, and returned in the form of echoes. These echoes are first and second echoes, and an echo (referred to a third echo) by the burst signal of the carrier frequency $\omega_3$. As in the first embodiment, the waveforms of the echoes are the same as those of the transmission signals.

As in the first embodiment, $\theta_1$ is obtained by using the equation (7) and the first echo. $\theta_2$ is obtained by using the equation (8) and the second echo. $\theta_3$ is obtained by using the third echo, and is given by $$\theta_3 = -2L\omega_3/V + \phi_3 - \psi_3 + 2l\pi \qquad (9)$$

where l: integer.

Since the fixed phase is known, the distance L can be obtained using the equations (7) and (8) as in the first embodiment. When noise is large, and the combination of a black circle and a white circle of which the positions are coincident with each other on the abscissa is not present as shown in FIG. 3, it is difficult to obtain the distance L using only $\theta_1$ and $\theta_2$. Therefore, using the equation (9), a measurement insensitive to noise is carried out. The signal processing process carried out in the signal processor portion 11 will be described.

FIG. 40 is a characteristic diagram for explaining the 29th embodiment of the present invention. In FIG. 40, a line representative of $\theta_3 - \phi_3 + \psi_3$ and a triangle solid polygonal line inclined at $-2L\omega_3/V$ are additionally depicted in the characteristic diagram in FIG. 3, used for explaining the first embodiment. The period of the characteristic line is equal to $\lambda_3/2$ where $\lambda_3$ is the wavelength of the wave of the angular frequency $\omega_3$.

In FIG. 3, for the angular frequency $\omega_1$, a polygonal line indicated by a fat dotted line corresponds to white circles, and for the angular frequency $\omega_2$, a polygonal line indicated by a fat solid line corresponds to black circles. In FIG. 40, for the angular frequency $\omega_1$, a polygonal line indicated by a fat one-dot chain line corresponds to black triangles, and for the angular frequency $\omega_2$, a polygonal line indicated by a fat dotted line corresponds to white circles. For the angular frequency $\omega_3$, a polygonal line indicated by a fat solid line corresponds to black circles. As seen, in FIGS. 3 and 40, the angular frequency for the fat solid line is smaller than the angular frequency for the fat broken line (fat one-dot chain line).

As in the first embodiment, where neither noise or fluctuation is present, a position of a block triangle obtained from $\theta_1 - \phi_1 + \psi_1$ is coincident with a position of a white circle obtained from $\theta_2 - \phi_2 + \psi_2$. Further, a position of a black circle obtained from $\theta_3-\phi_3+\psi_3$ is coincident with it. The coincident positions of the black triangle, white circle, and black circle indicate a distance L.

Where noise and fluctuation are present, the positions of a block triangle, a white circle and a black circle are not always coincident with each other. In this case, the distance L is determined by the signal processing process. The signal processing process will be described.

As shown in FIG. 41, as in the first embodiment, information on the amplitudes or the envelopes of the echoes for the first or the second transmission signal is also used for determining the # k-th portion in the step $S_D$. As a result, the number of the black triangles, white circles, and black circles shown in FIG. 40 is reduced to a finite number of those marks in the step S60. Distances of the black triangles, white circles, and black circles are $a_n$ (n=1, 2, ..., N), $b_m$ (m=1, 2, ..., M), and $c_o$ (o=1, 2, ..., O).

As shown in FIG. 41, the absolute value of the difference between $a_n$ and $b_m$ is computed in the step S610. In principle, some of $D_{nm}$ (n=1, 2, ..., N; m=1, 2, ..., M) should be zero. However, actually, these are not perfectly zero. To cope with, as shown in FIG. 41, in the step S620, the minimum value denoted as $D_{ij}$ of $D_{nm}$ is looked up, and the combination of $a_n$ and $b_m$ (represented by $a_i$ and $b_j$, respectively) which provides the minimum value $D_{ij}$ is detected, to thereby determine the range of $a_{i-1}$, $b_{j-1}$ to $a_{i+1}$, $b_{j+1}$.

In the step S630, in the range of $a_{i-1}$, $b_{j-1}$ to $a_{i+1}$, $b_{j+1}$, the absolute value of the difference between $a_n$ and $c_o$ is calculated. This value is denoted as $E_{no}$. In the step S640, the minimum value denoted as $E_{ik}$ of this $E_{no}$ is looked up, in the step S650, the combination of $a_n$ and $c_o$ (represented by ai and $c_o$) which provides the minimum value $E_{ik}$ is detected, and in the step S7, $(a_i+b_j+c_o)/3$ is outputted as the measurement result.

The useful effects of the 29th embodiment will be described. As described above, three different frequencies of the burst signals as the transmission signals are used. Then, even if $D_{ij}$ or $E_{ik}$ is not perfectly zero, the measurement result is obtained at a desired accuracy. The four or more different frequencies of the burst signals may be used, if required. The measuring accuracy is more improved as the number of frequencies is increased. The 29th embodiment may be applied to other embodiments. Also in this case, the useful effects can be obtained.

The first embodiment will be described again.

For the overall operation and the signal processing procedure of the ultrasonic distance measuring device described referring to FIGS. 1 to 5, various types of signal processing precesses are present as shown in FIGS. 6 to 8. An additional signal processing process is illustrated in FIG. 45.

In the signal processing process shown in FIG. 7, in steps S151 and S251, the phase of the echo is detected, and distance candidates $L(\theta_1)$ and $L(\theta_2)$ are derived on the detected phase in advance. From the derived distance candidates, the distance candidates are derived again on the basis of the determination results in the candidate-contained portion determining step $S_D$.

Figure 45:
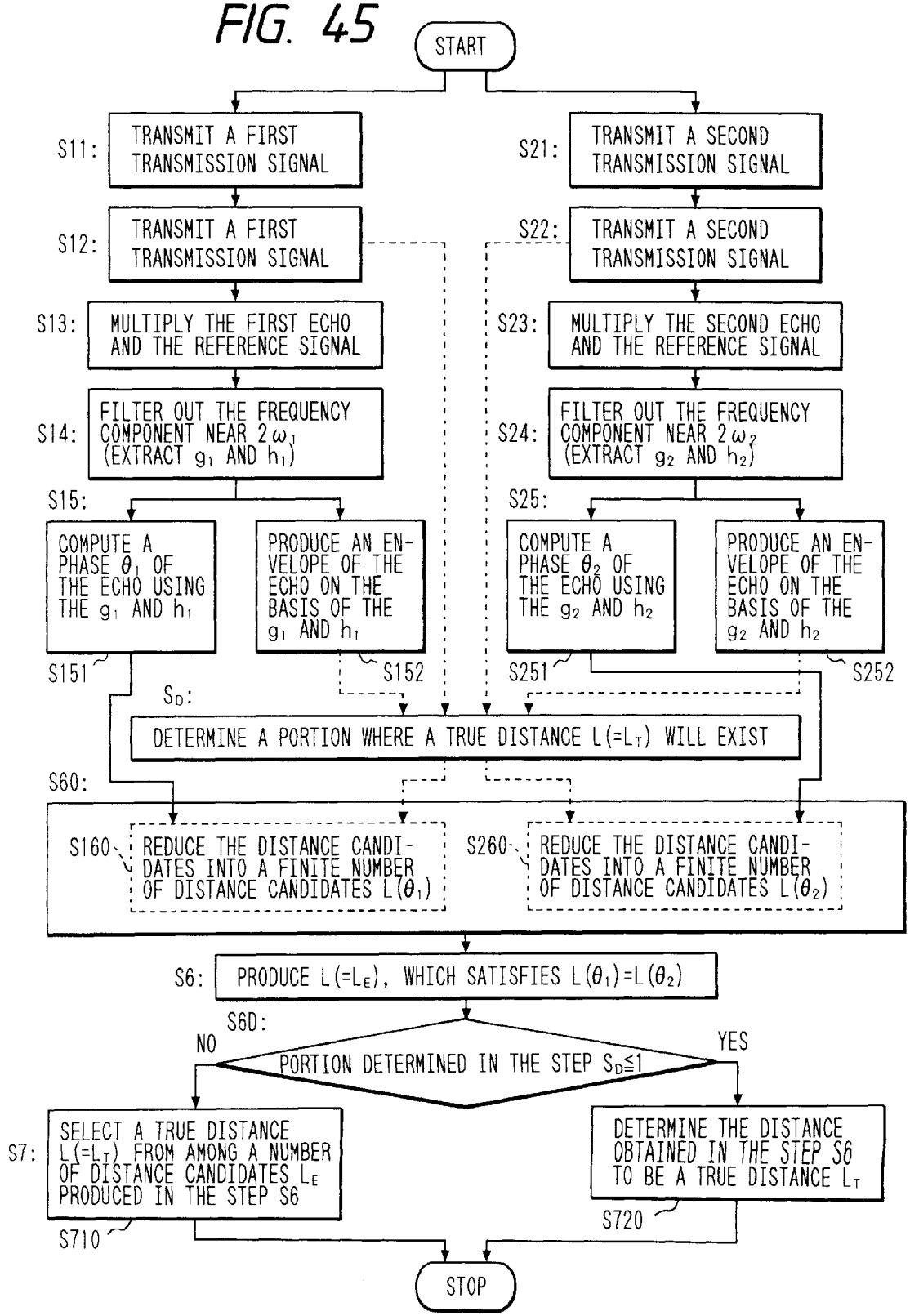
FIG. 45 shows a flowchart showing a fourth signal processing process in the first embodiment of the present invention.

In the signal processing process shown in FIG. 45, in steps S151 and S251, the phases $\theta_1$ and $\theta_2$ of the echoes are detected, and in steps S160 and S260, the distance candidates $L(\theta_1)$ and $L(\theta_2)$ in the determined portion are derived using the detected result and the determination results in the step $S_D$.

In FIG. 45, steps S11 to S14 and S21 to S24 are the same as those in FIG. 7.

The steps S6 to S7 in FIG. 45 describe the $L_T$ deriving method. For these steps, the steps S6 to S7 shown in FIG. 33 are used.

The useful effects of the signal processing procedure shown in FIG. 45 will be described.

In FIG. 7, in the steps S151 and S251, the phase is detected and the distance candidates are derived. If the distance candidates are obtained by merely detecting the phase, the distance candidates must be obtained in all of the portions. A long computing time is consumed in the signal processor portion 11.

In FIG. 45, in the steps S151 and S251, any other process than the phase detection is not carried out. After the candidate-contained portion determining step $S_D$, the distance candidates are obtained in the determined area, so that the computing time in the signal processor portion is shorter than that in FIG. 7.

30th Embodiment

This embodiment is designed such that a plural number of true-distance contained portion candidates are derived, and distance candidates are derived from those derived true-distance contained portion candidates.

The 30th embodiment of the present invention will be described with reference to FIGS. 46, 47, and 48. In the upper part of FIG. 46, characteristic lines similar to those in FIG. 4 shows the relationship between distance and phase. The abscissa is segmented at intervals Lr from the origin. Of those segmental portions, the k-th portion counted from the origin is called a # k-th portion.

Figure 46:
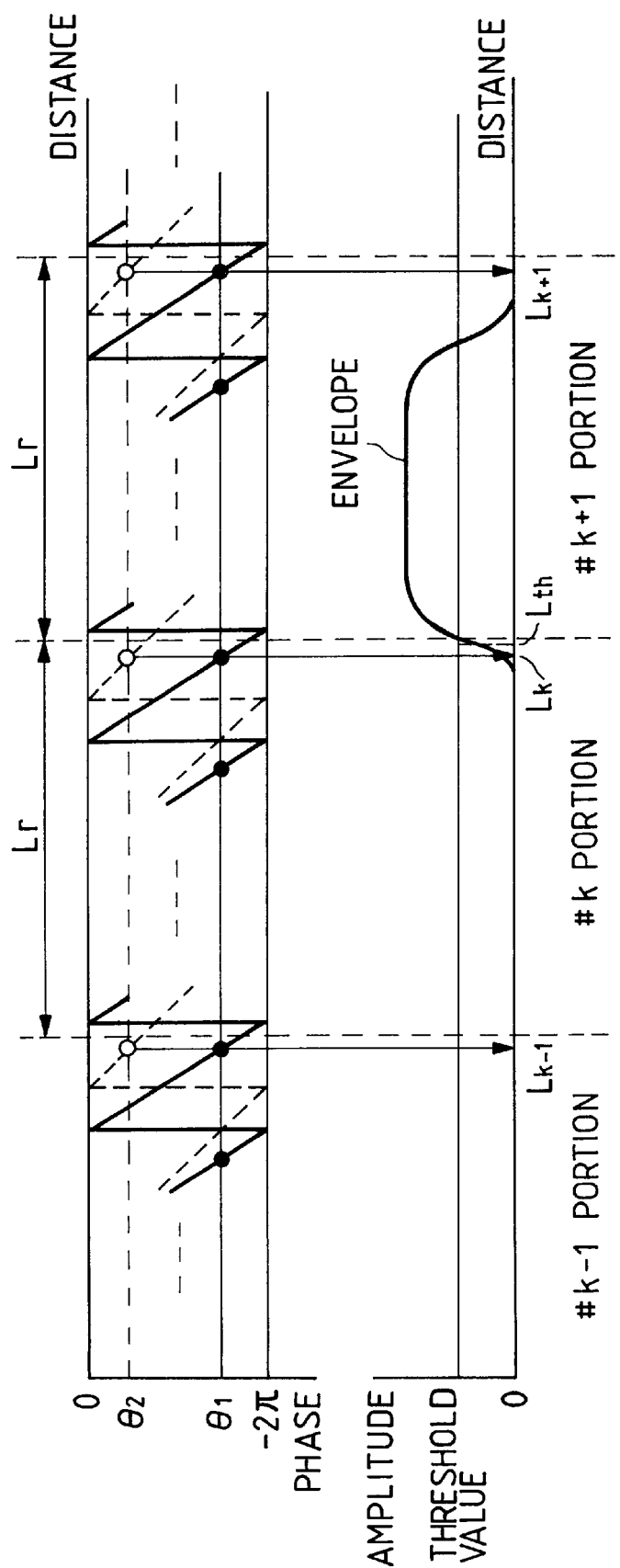
FIG. 46 shows a characteristic diagram for explaining the signal processing process in the 30th embodiment.
Figure 47:
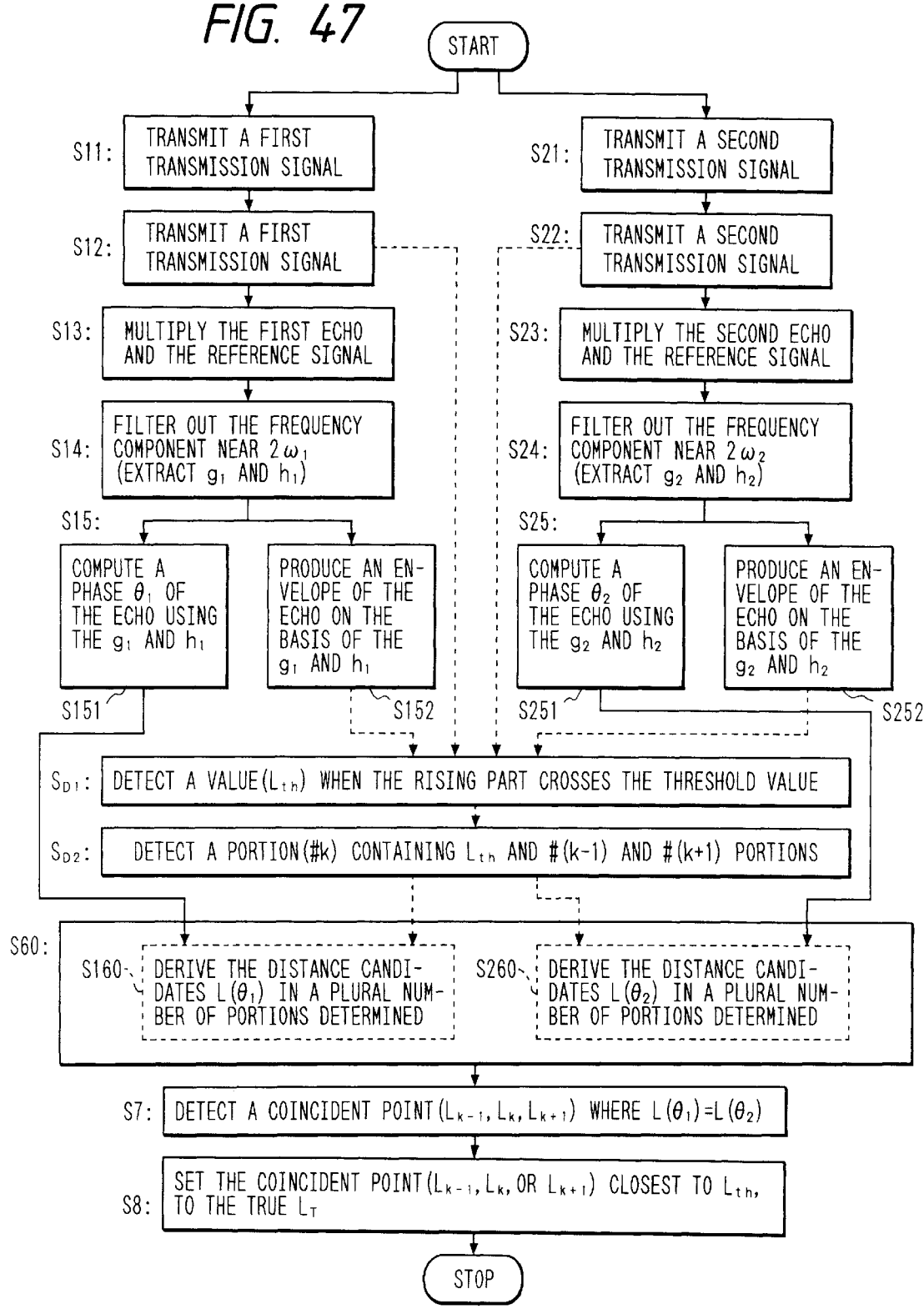
FIG. 47 shows a flowchart showing a signal processing process in the 30th embodiment of the present invention.

In the lower part of FIG. 46, an envelope of the echo is depicted along the abscissa representative of distance, in connection with the upper part of the drawing. As shown in FIG. 46, a threshold value is set on the amplitude. A distance when the rising part of the envelope crosses the threshold value is denoted as $L_{th}$. In the instance shown in FIG. 46, the threshold value $L_{th}$ is present in a location in the # k-th portion, which is closer to the # (k+1)th portion. In this case, if it is determined that the $L_{th}$ contained portion is a portion containing a true-distance $L_T$ therein, the output of the candidate-contained portion determining step $S_D$ is not definite in the overall operation procedure shown in FIG. 6 or 7. More specifically, the # k-th portion may be recognized as # (k+1)th portion, mistakenly.

To avoid such a mistaken determination, positions of the black circles and the white circles when these circles are projected onto the abscissa are obtained in a total of three portions, # (k−1)th portion, # k-th portion, and # (k+1)th portion, as in the first embodiment. And the positions of the circles where these are coincident with each other are obtained. In this way, the coincident positions of both the circles are detected. In the # (k−1)th portion, # k-th portion, and # (k+1)th portion, these coincident points are denoted as $L_{k-1}$, $L_k$, and $L_{k+1}$.

$L_{th}$ lies at a point in the rising part of the envelope. Accordingly, it can be considered that $L_T$ also lies at a point in the rising part of the envelope. Hence, $L_{th}$ is close to $L_T$. As a consequence, of those points $L_{k-1}$, $L_k$, and $L_{k+1}$, the point closest to $L_{th}$ is $L_T$. In the instance of FIG. 46, $L_k$ is closest to $L_{th}$, so that $L_T$ is $L_k$. And the portion is the # k-th portion.

A flow of the overall signal processing process as described above is shown in FIG. 47. In FIG. 47, the steps S15 and S25 are the same as that shown in FIG. 45. In FIG. 47, a plural number of portions are detected in the step $S_{D2}$. Subsequently, in the step S6, distance candidates are derived in a plural number of porions. In the step S7, the coincident point is detected every portion. Finally, in the step S8, the coincident point closes to the $L_{th}$ is detected and used as $L_T$.

Figure 48:
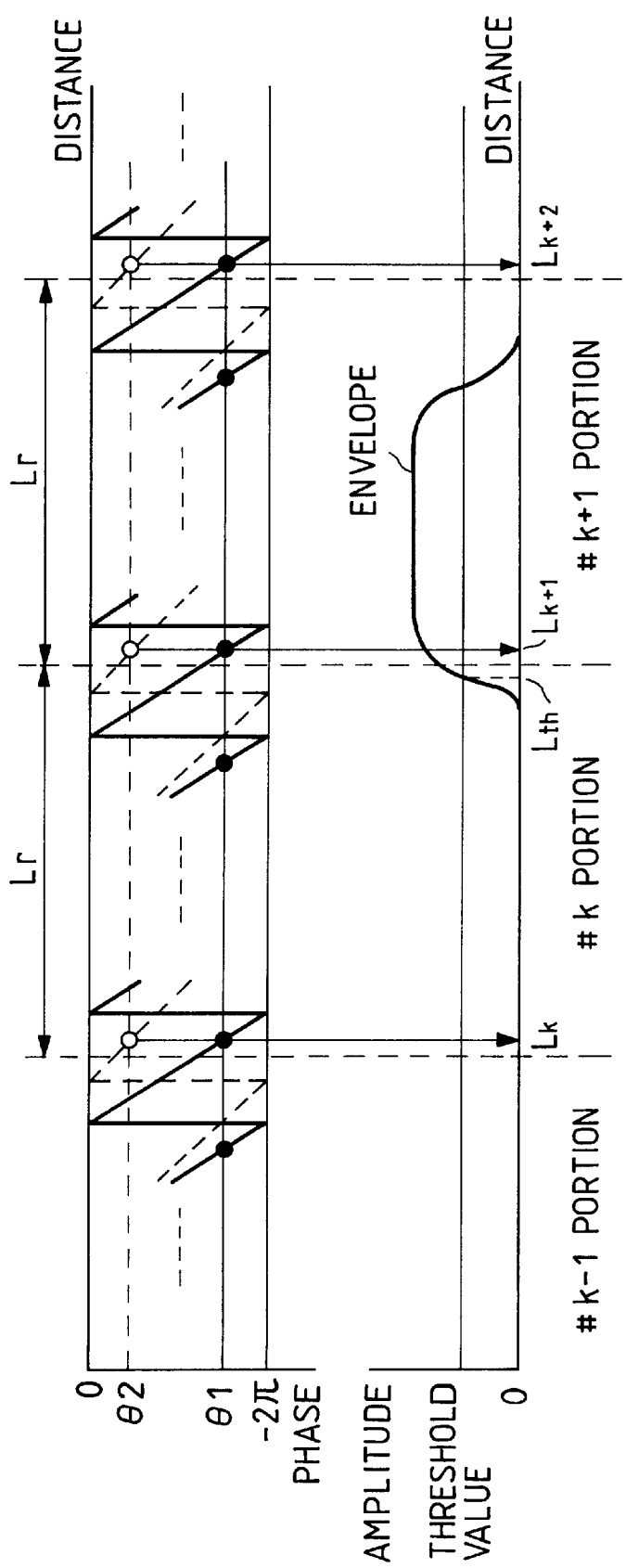
FIG. 48 shows a characteristic diagram for explaining the signal processing process in the 30th embodiment.

A case different from the FIG. 46 case is shown in FIG. 48. In FIG. 46, $L_{th}$ and $L_T$ (or $L_k$) are both present in the # k-th portion, the coincident point closest to the $L_{th}$ (in the illustrated case, $L_{k+1}$) is present in the # (k+1)th portion. In such a case, the signal processing procedure shown in FIG. 6 or 7 recognizes $L_k$ as $L_T$. As seen from FIG. 48, the envelope does not rise yet at $L_k$. Accordingly, it is easy to understand that $L_k$ is not $L_T$. Accordingly, in the signal processing procedure shown in FIG. 6 or 7, a measurement result shorter than the true distance by one segmental portion is outputted. However, if the signal processing shown in FIG. 47 is carried out, an exact measurement result can be obtained.

The qualitative description has thus far been made. Experiments on the first embodiment and 30th embodiment were conducted. These experiments will be described hereinbelow.

EXPERIMENT ON THE FIRST EMBODIMENT

For the distance between the probe and an object, the thickness of a test piece was measured. In this experiment, the test piece corresponds to the ultrasonic wave propagating medium, and the bottom surface of the test piece corresponds to the reflecting surface of the object.

Figure 49A:
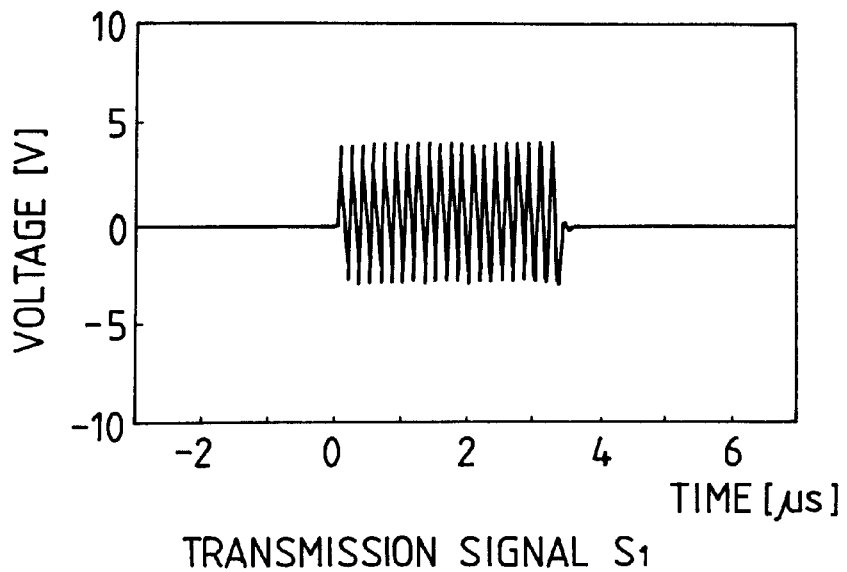
FIGS. 49(a) and 49(b) show diagrams showing a transmission signal in an experiment on the first embodiment of the present invention.
Figure 49B:
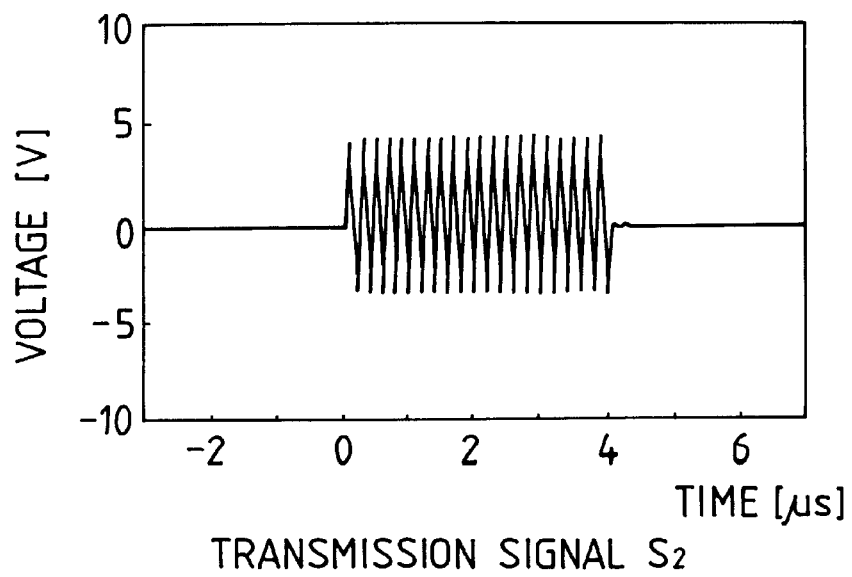

Transmission signals s1 and s2 are illustrated in FIGS. 48(a) and 49(b). The carrier frequencies f1 and f2 were 6 MHz and 5 MHz. The oscillation continuation times $T_{O1}$ and $T_{O2}$ were 20/6 μs and 20/5 μs.

Figure 50A:
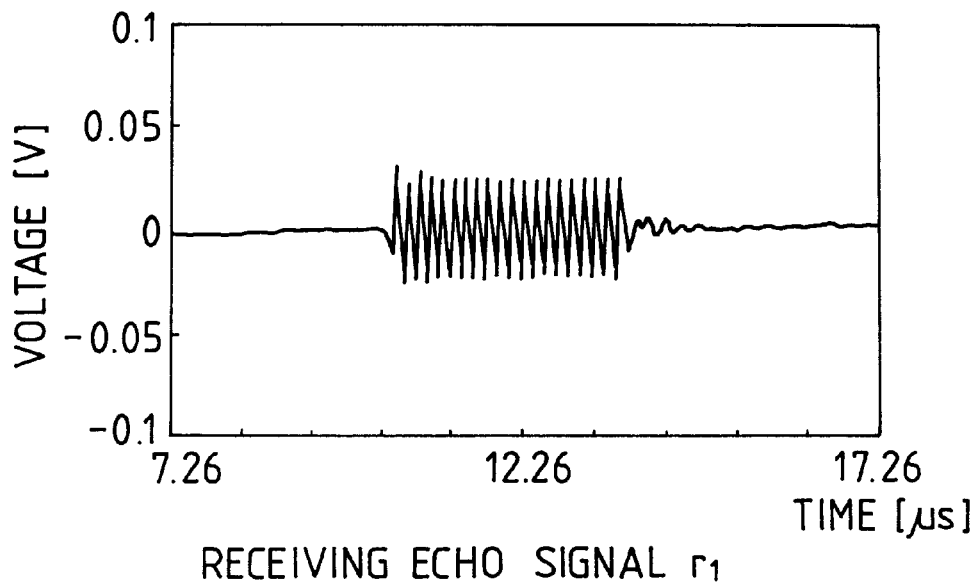
FIGS. 50(a) and 50(b) show diagrams showing a receiving echo signal in the experiment on the first embodiment of the present invention.
Figure 50B:
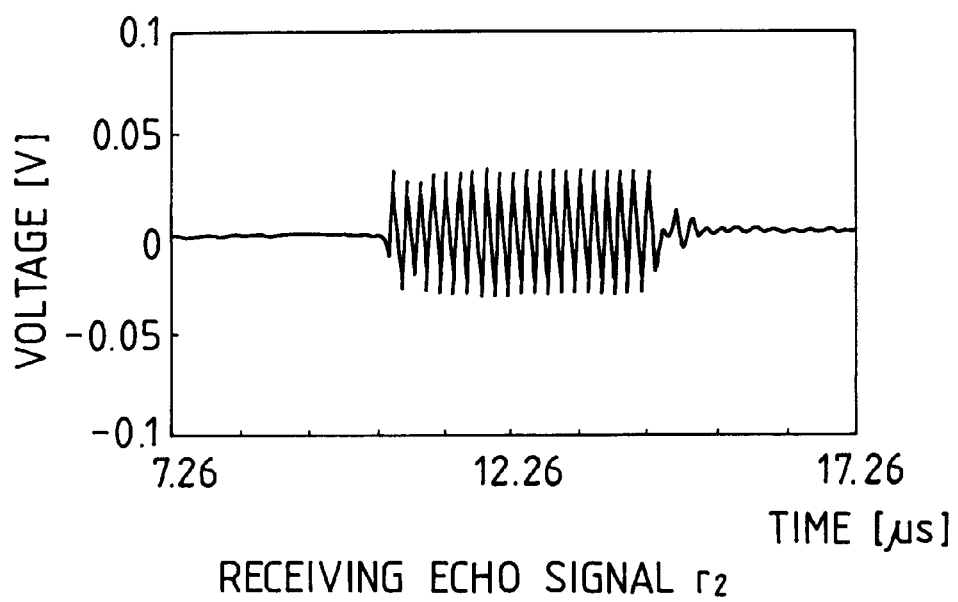

The thickness of the test piece was 30 mm. In FIGS. 50(a) and 50(b), there are shown echo signals r1 and r2 for the thickness of 30 mm. In the signal processing procedure to follow, the echo signal obtained through one transmission repetitive period shown in FIGS. 50(a) and 50(b) was used as it is (here, the synchronous averaging process is not carried out in which the echo signal obtained each transmission repetitive period is averaged over a plural number of transmission repetitive periods).

Figure 51A:
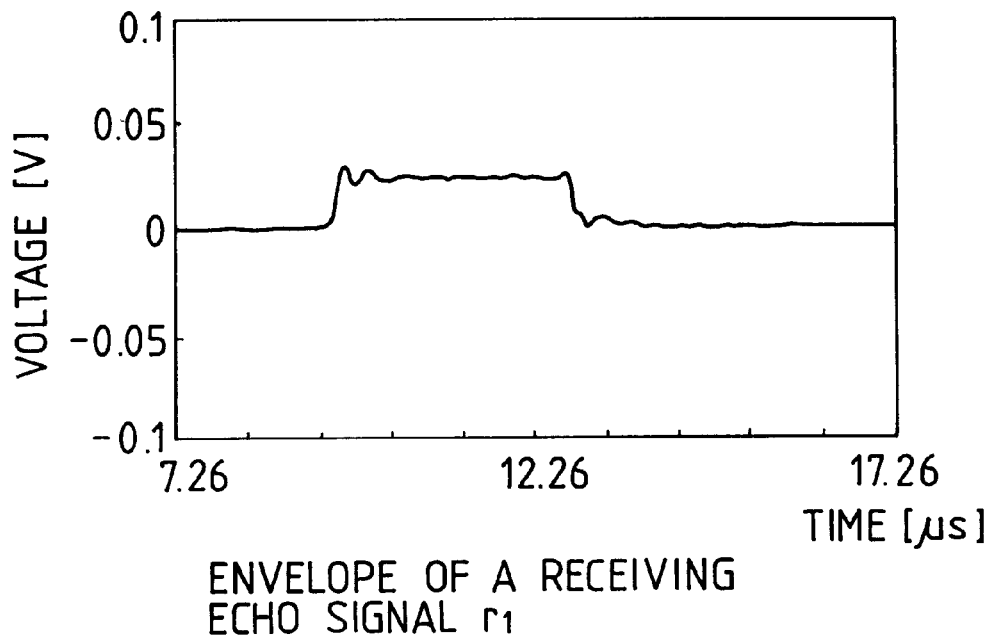
FIGS. 51(a) and 51(b) show diagrams showing an envelope in the experiment on the first embodiment of the present invention.
Figure 51B:
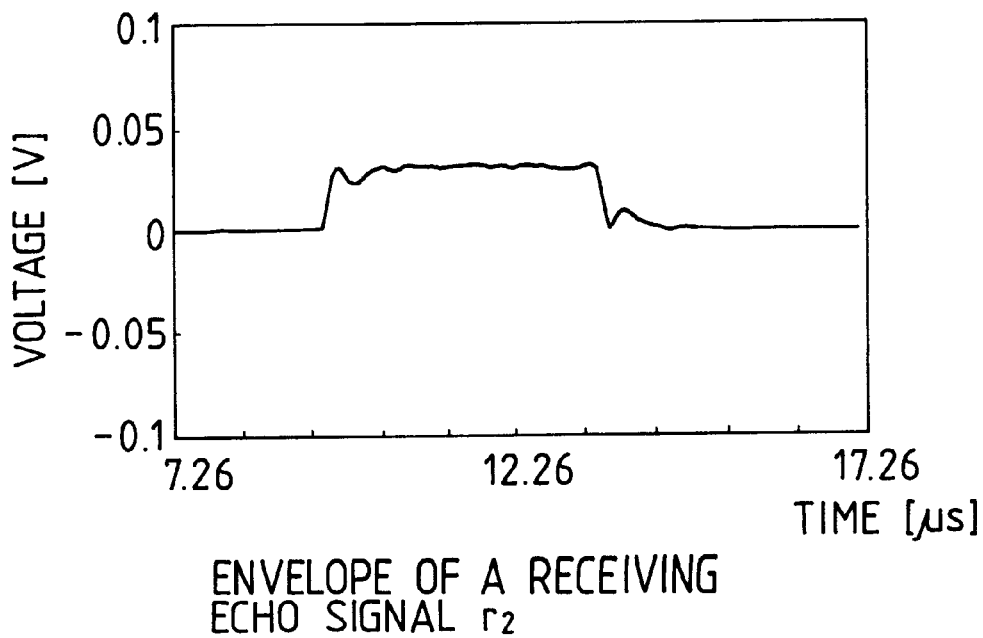
Figure 52A:
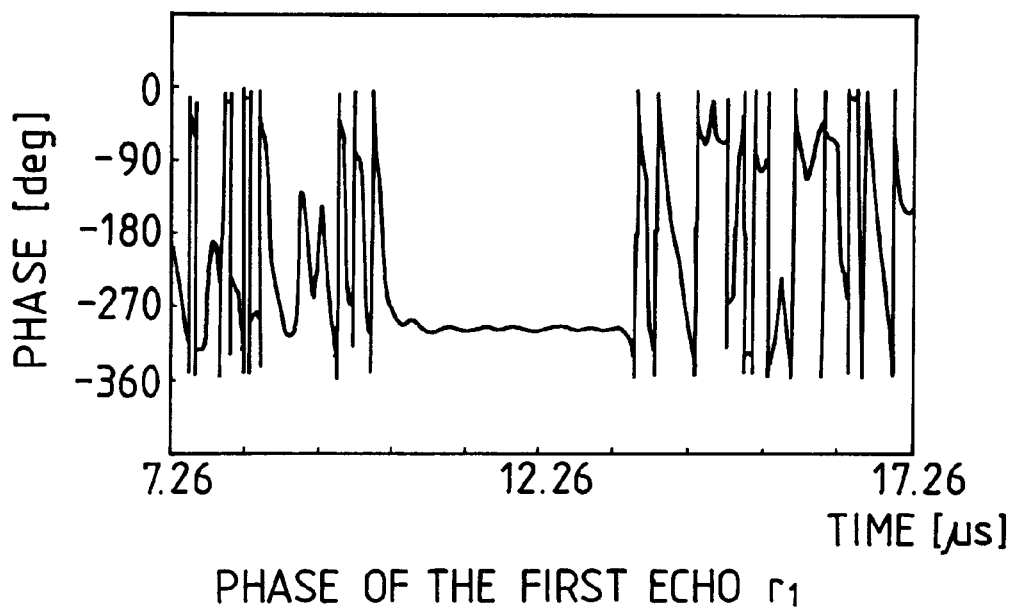
FIGS. 52(a) and 52(b) show diagrams showing phase in the experiment on the first embodiment of the present invention.
Figure 52B:
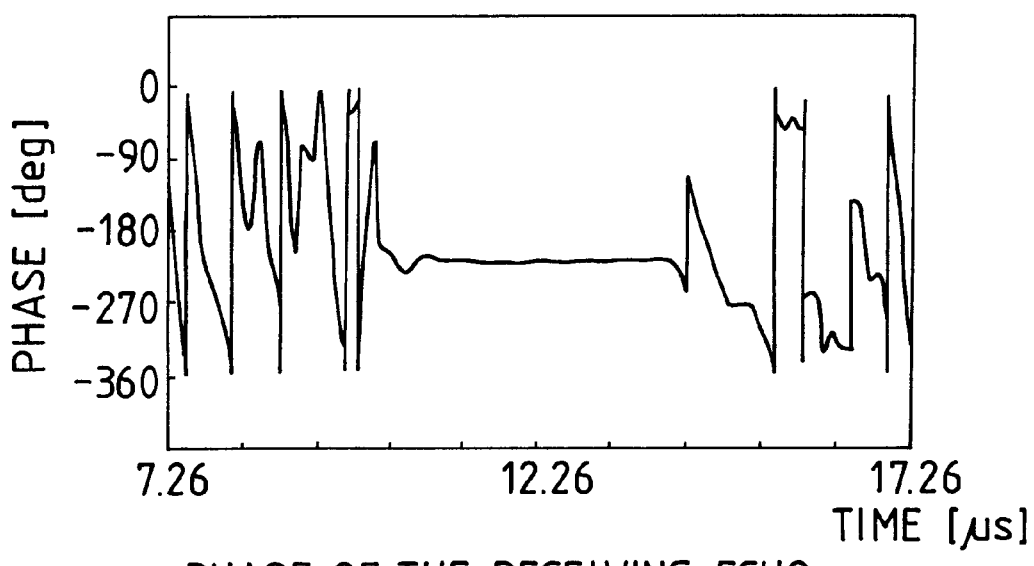

In FIGS. 51(a) and 51(b), there are shown the envelopes of the echo signals r1 and r2. In FIGS. 52(a) and 52(b), there are shown the phases of the echo signals r1 and r2. The phases $\theta_1$ and $\theta_2$ were obtained by averaging the flat part in the center of the echo signal. As a result, the phases $\theta_1$ and $\theta_2$ were −296.2° and −219.60 °.

Figure 53A:
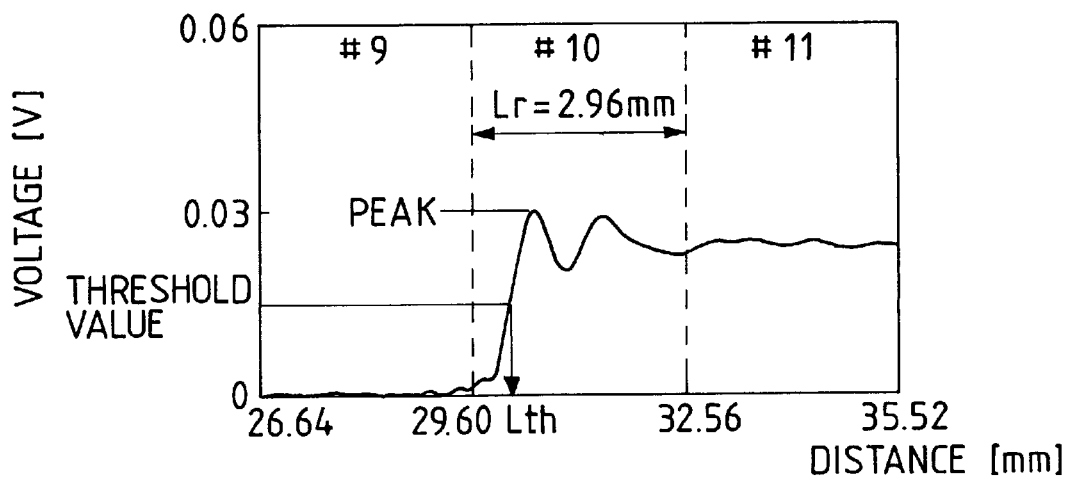
FIGS. 53(a) and 53(b) show diagrams showing a relationship between an envelope of the echo signal and a portion in the experiment on the first embodiment of the present invention.
Figure 53B:
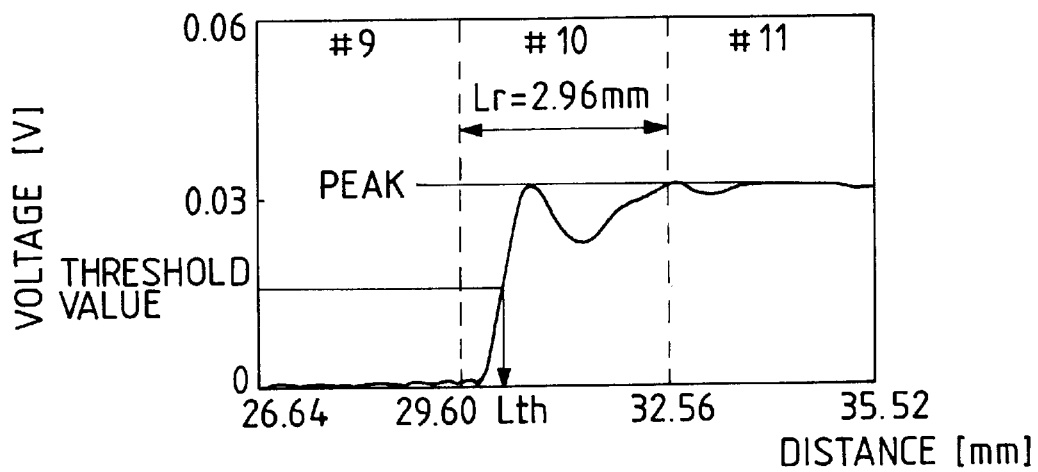

In FIGS. 53(a) and 53(b), the rising parts of the envelopes shown in FIGS. 51(a) and 51(b) are illustrated in an enlarged fashion. By using the fact that a sonic speed V of the test piece is 5920 m/s, those are illustrated in a state of the variable conversion from a time domain to a distance domain. The period Lr is 2.96 mm. In FIG. 53(a), the threshold value is set at ½ of the peak value of the envelope. Then, the portion is #10th portion. When the portion is similarly detected from FIG. 53(b), the same result is obtained.

Figure 54:
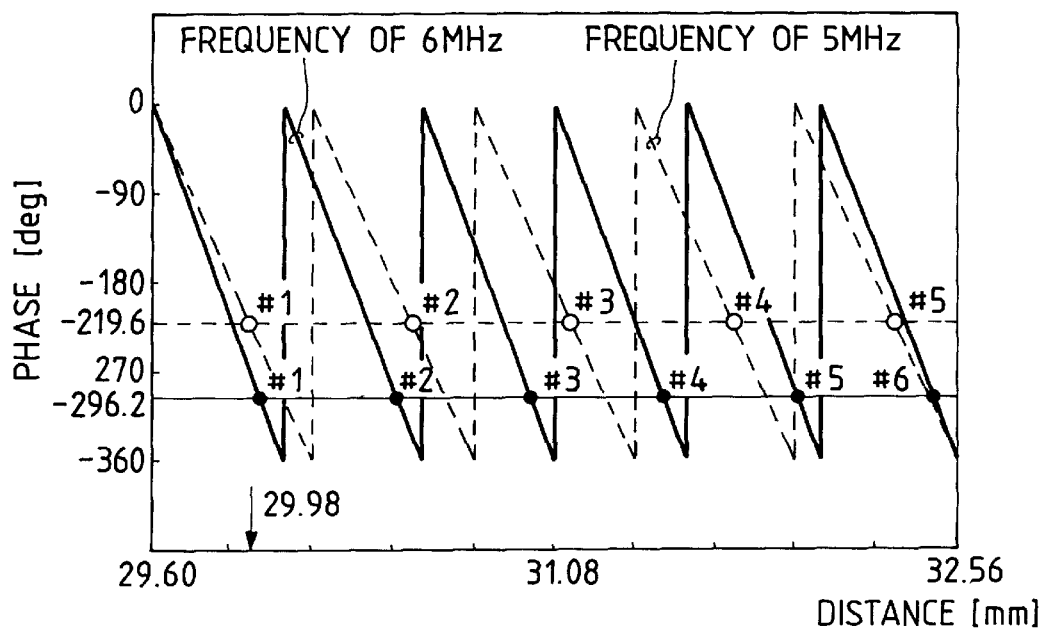
FIG. 54 shows a diagram showing a relationship between a phase and distance in the experiment on the first embodiment of the present invention.

FIG. 54 shows a relationship between the phase and distance in the #10th portion. As shown, distances (distance candidates) for the black circles and the white circles are numbered. The combination of the white circle and the black circle of which the difference is zero should be present. However, such a combination was not present. This is due to the fact that the phase measurement result contains an error. The combination of which the difference is the smallest in absolute value is selected and its average value is outputted as the result of the measurement result. This combination contains the black circle #1 and the white circle #2, and the average value was 29.98 mm.

EXPERIMENT OF THE 30th EMBODIMENT

Figure 55A:
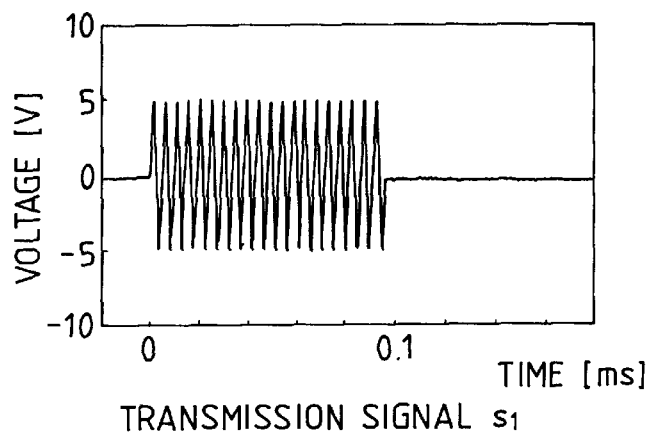
FIGS. 55(a) and 55(b) show diagrams showing a transmission signal in an experiment on the 30th embodiment of the present invention.
Figure 55B:
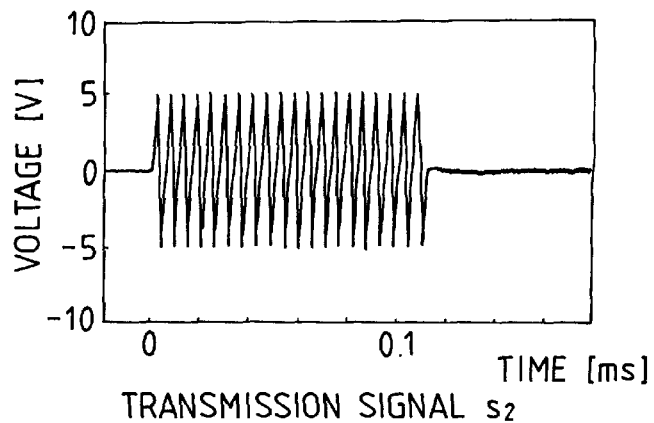
Figure 56A:
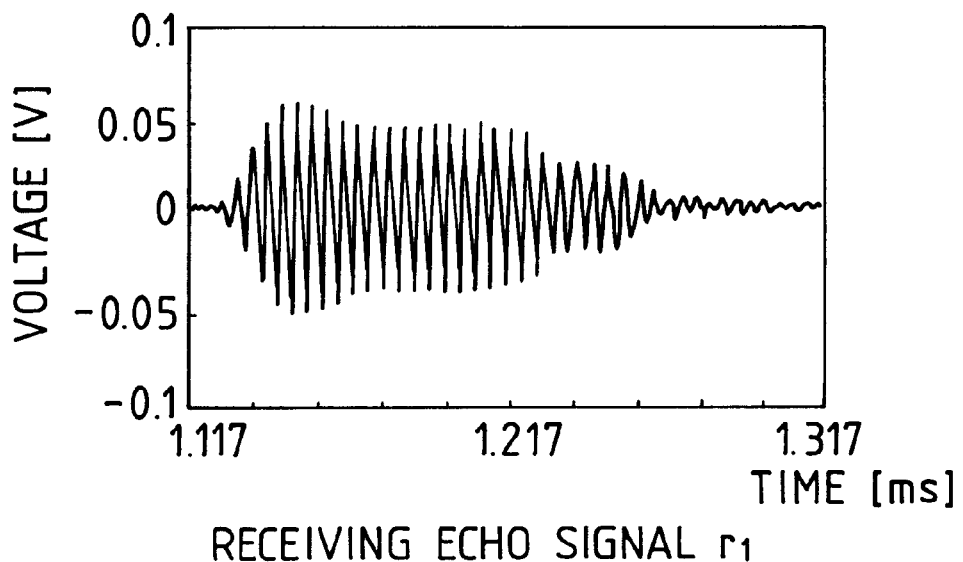
FIGS. 56(a) and 56(b) show diagrams showing a receiving echo signal in the experiment on the 30th embodiment of the present invention.
Figure 56B:
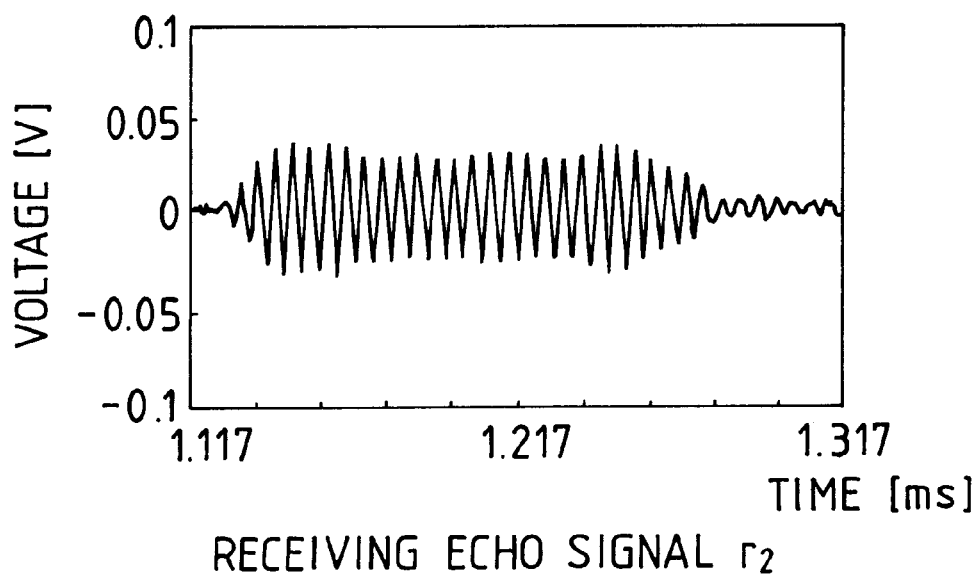

A distance between a metal plate placed in the air and a probe was measured. Transmission signals s1 and s2 are illustrated in FIGS. 55(a) and 55(b). The carrier frequencies f1 and f2 were 210 MHz and 180 MHz. The oscillation continuation times $T_{O1}$ and $T_{O2}$ were 20/210 μs and 20/180 μs. Echo signals r1 and r2 are shown in FIGS. 56(a) and 56(b). These echo signals were obtained by making use of the synchronous addition averaging process.

Figure 57A:
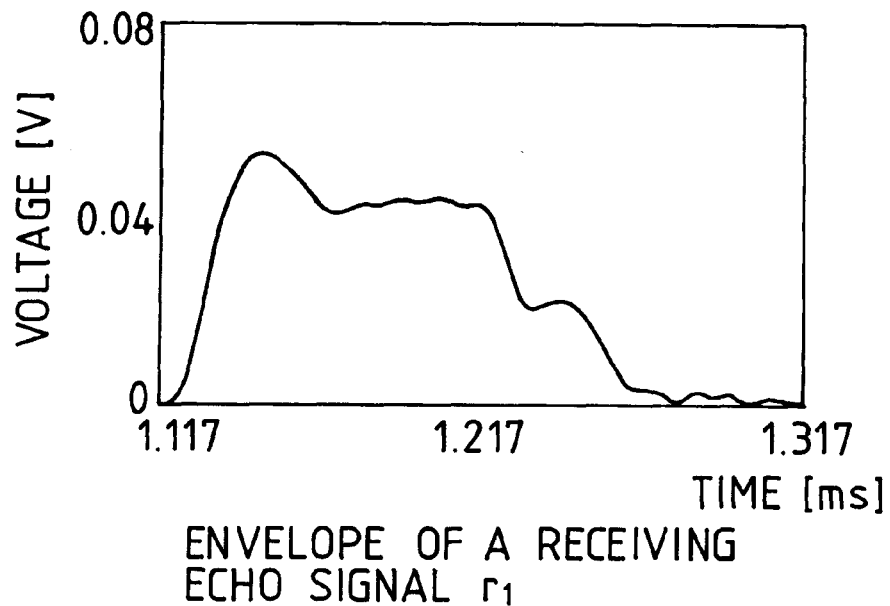
FIGS. 57(a) and 57(b) show diagrams showing an envelope in the experiment on the 30th embodiment of the present invention.
Figure 57B:
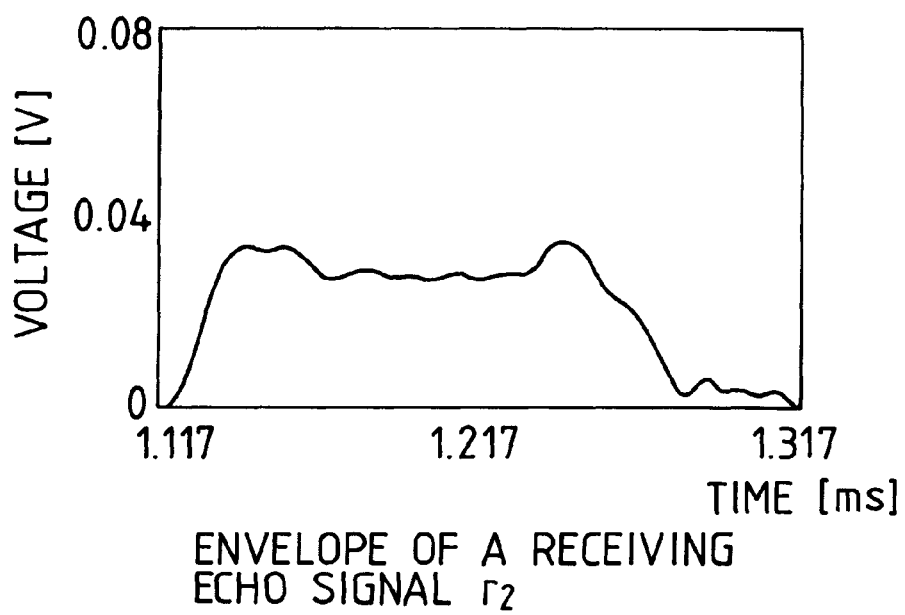
Figure 58A:
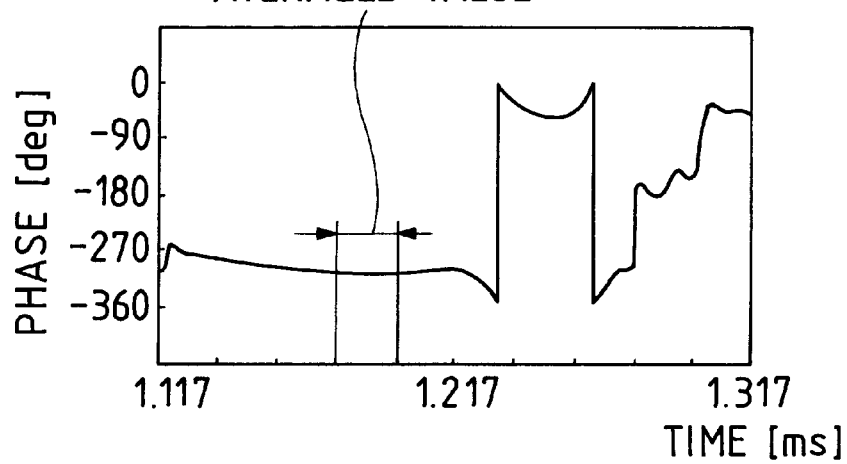
FIGS. 58(a) and 58(b) show diagrams showing phase in the experiment on the 30th embodiment of the present invention.
Figure 58B:
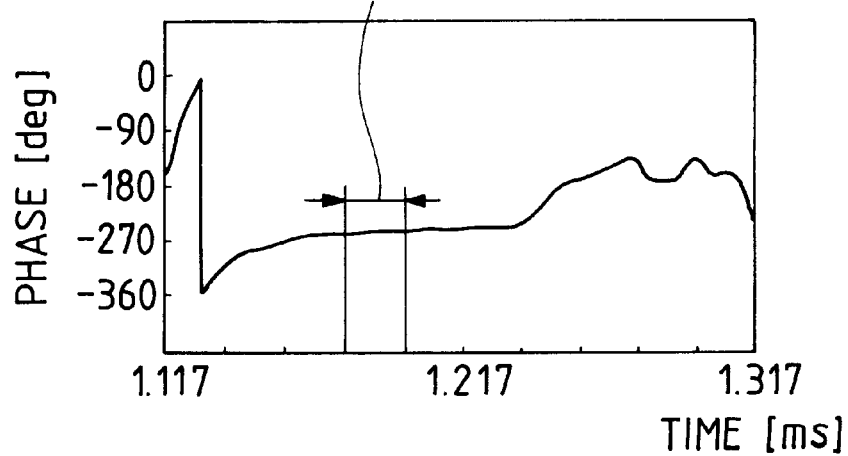

The envelope and the phase of the echo signal r1 shown in FIG. 56(a) were obtained. The envelope and the phase of the echo signal r2 shown in FIG. 56(b) were obtained. FIGS. 57(a) and 57(b) show envelopes of the echo signals r1 and r2. FIGS. 58(a) and 58(b) show phases of the echo signals r1 and r2. In FIGS. 58(a) and 58(b), the phase is flat in the central part of the echo signal, but varies with time in the rising part and the falling part of the echo signal. The reason for this is that the probe used for the experiment is narrow in the frequency band. This is due to the fact that in the rising part and the falling part of the echo signal, the carrier frequency of the echo signal is shifted from the carrier frequency of the transmission signal. The values in the flat central part were averaged to thereby obtain phases $\theta_1$ and $\theta_2$.

Figure 59:
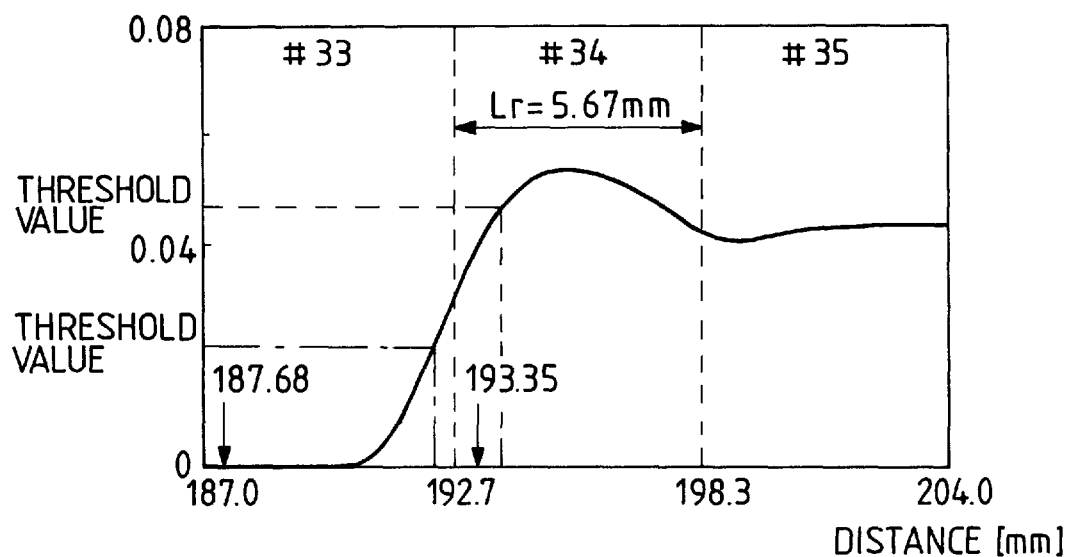
FIG. 59 shows a diagram showing a relationship between an envelope of the echo signal and a portion in the experiment on the 30th embodiment of the present invention.

A portion was detected by using the envelope of the echo signal r1. In FIG. 59, there is shown the relationship between the portion and the envelope. Since a sonic speed is 340 m/s, the period Lr is 5.67 mm. As indicated by a dotted line and a one-dot chain line, the portion detect results depends on the setting of the threshold value. One portion is #34 while the other portion is #33. Which is true was determined in a manner that as shown below, in the portions #34 and #33, the distance coincident point is obtained using the phases $\theta_1$ and $\theta_2$, and the result was used.

Figure 60:
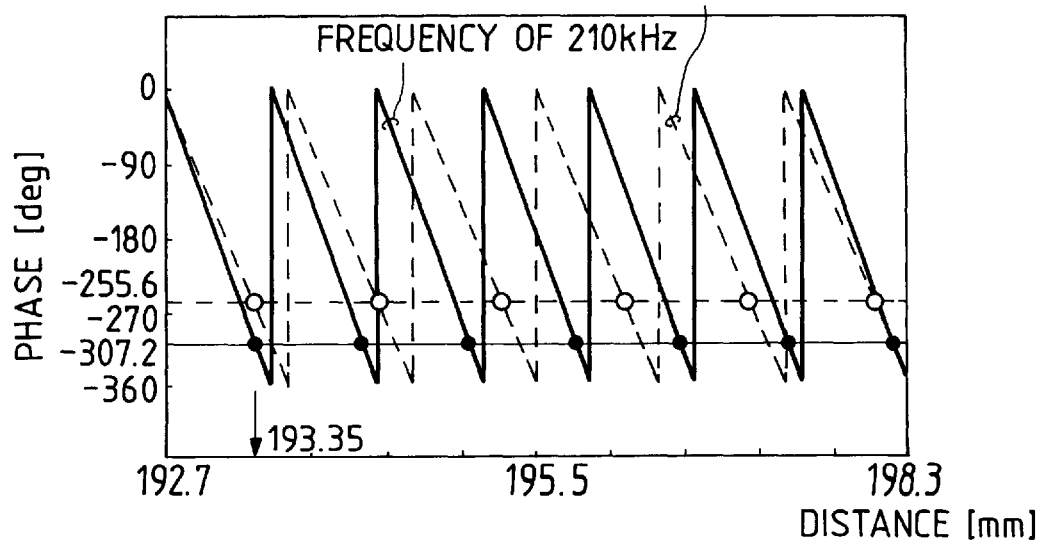
FIG. 60 shows a diagram showing a relationship between a phase and distance in the experiment on the 30th embodiment of the present invention.

FIG. 60 shows a relationship between phase and distance in the #34 portion. As shown, the phases $\theta_1$ and $\theta_2$ were −307.2° and −255.60°. In FIG. 60, the combination of the black circle and the white circle of which the difference is smallest is detected and their average value is used as a coincident point. As a result, in the #34 portion, Lo=193.35 mm.

In the #33 portion, the coincident point was obtained in a similar way. It was 187.68 mm as the result of subtracting the period Lr from 193.35 mm. These values are depicted with arrows applied thereto in FIG. 59. As seen from FIG. 59, at the arrow position in the #33 portion, no echo is received. Therefore, the #34 portion is true and the distance Lo is 193.35 mm.

Various embodiments of the present invention have been described independently. If one embodiment is applied to other embodiments, the useful effects of those embodiments are additive.

Various embodiments of the present invention have been described independently. If one embodiment is applied to other embodiments, the useful effects of those embodiments are additive.

The present invention is applicable to an ultrasonic distance measuring device of the type in which an array probe is used and the ultrasonic beam is electronically moved for scan. The pulse compression method is disclosed in Published Unexamined Japanese Patent Application Nos. Hei. 2-226065, 4-289453, 4-127054, 3-162667, 3-138563, 4-9656, 4-9657, 4-9658, This pulse compression method may be applied to the present invention in a manner that the first transmission signal given by the equation (1) in the present invention and the second transmission signal given by the equation corresponding to the equation (1), not shown, may be used for the fundamental signal in those publications. In this case, S/N performance is remarkably improved.

Probing an article buried in the underground is enumerated for one of the applications of the present invention. In the underground, attenuation of the ultrasonic wave is great. To cope with this, ultrasonic wave of low frequency, 100 Hz, at which the attenuation is relatively small must be used. Where the low frequency is used, the wavelength is long and the resolution is deteriorated in the conventional device. On the other hand, the ultrasonic distance measuring device of the present invention does not depend on the wavelength in its measuring. In this respect, the present invention is very useful when it is applied to the ultrasonic wave propagating medium suffering from large attenuation, such as underground.

While the present invention has been described using the devices using the ultrasonic wave, the invention may be applied to any type of device using sonic wave, elastic wave, electromagnetic wave or the like. In the above-mentioned embodiments, the object to which the transmission signal is projected is a specific object, such as an object to be detected. However, it is not limited to such a physical member, but may be something which provides a reflecting wave in response to the transmission signal received. For example, an electric field or a magnetic field may be used. When an electromagnetic wave as a transmission signal is applied to the magnetic field or the electric field, and reflected by it. In this case, the distance to or the shape of the magnetic field or the electric field can be measured. Accordingly, the object to which the transmission signal is directed includes not only solid but also fluid, gas, or the like.

While the present invention has been described using the device for detecting the distance to and the shape of the object, it is evident that the invention is applicable for detecting presence or absence of an object.

Another application of the invention is an inspection of building structures. Concrete used the building structure greatly attenuates ultrasonic wave. The frequency of 1 MHz or lower at which the ultrasonic wave attenuation is small must be used. Where such a low frequency is used, the wavelength is long and the resolution is deteriorated in the conventional device. The ultrasonic distance measuring device of the present invention does not depend on the wavelength in its measuring. In this respect, the present invention is very useful when it is applied to the ultrasonic wave propagating medium suffering from large attenuation, such as concrete.

Besides, in the above-mentioned embodiments, a physical quantity of an object is detected on the basis of a reflection signal from the object as a receiving signal. The detecting method and the detecting apparatus according to the present invention are also applicable to detect a physical quantity of an object on the basis of the signals that penetrate and propagate through the object as a receiving signal received by a receiving means different from a transmitting means.

In the present invention, a first candidate of physical quantity on a detected object by a first frequency is derived on the basis of a first reflecting signal of the first frequency, a second candidate of physical quantity on a detected object by a second frequency is derived on the basis of a second reflecting signal of the second frequency, and a third candidate of physical quantity on a detected object by the first and the second frequency is derived on the basis of the first and the second candidate. Therefore, the physical quantity of the detected object can be detected at high accuracy.

What is claimed is:

1. A method for detecting a measurable quantity of an object, comprising the steps of:

transmitting a first burst signal of a first frequency to the object to be detected;

transmitting a second burst signal of a second frequency, which is different from the first frequency, to the object;

receiving a first receiving signal, which corresponds to the first burst signal, from the object;

receiving a second receiving signal, which corresponds to the second burst signal, from the object;

deriving a first candidate of the measurable quantity of the object on the basis of the first receiving signal;

deriving a second candidate of the measurable quantity of the object on the basis of the second receiving signal; and deriving a third candidate of the measurable quantity of the object by selecting one of the first candidate and the second candidate wherein said first candidate deriving step derives a finite number of first candidates of physical quantity of the object by the first frequency on the basis of the phase of the first receiving signal, and said second candidate deriving step derives a finite number of second candidates of physical quantity of the object by the second frequency on the basis of the phase of the second receiving signal.

2. The method according to claim 1, wherein the step of deriving a first candidate includes deriving a finite number of first candidates of the measurable quantity of the object on the basis of first waveform information of the first receiving signal, the step of deriving a second candidate includes deriving a finite number of second candidates of the measurable quantity of the object on the basis of second waveform information of the second receiving signal, and the step of deriving a third candidate includes deriving a finite number of third candidates of the measurable quantity of the object.

3. The detecting method according to claim 1, further comprising the step of:

selecting a specific candidate from among said third candidates derived by said third candidate deriving step and determining the specific candidate as a physical quantity of the object.

4. The method according to claim 3, further comprising:

a step of determining a group where the third candidate corresponding to the true measurable quantity of the object is determined, the third candidate, corresponding to the true measurable quantity of the object, being a member of the finite number of first candidates and of the finite number of second candidates, which are periodically derived at periods that are determined by the first and the second frequency and a propagating speed of the first and second burst signal, respectively, and a selecting/determining step which further includes the steps of:

selecting a specific candidate from among the third candidates on the basis of the determining result of the step of determining a group where a candidate corresponding to the true measurable quantity of the object is determined; and determining that the specific candidate is the true measurable quantity of the object.

5. The method according to claim 1, further comprising:
a step of determining a group where the third candidate that corresponds to a true measurable quantity of the object is determined, the third candidate corresponding to the true measurable quantity of the object being a member of a group of first candidates and a group of second candidates, which are periodically derived at periods determined by the first and the second frequency and a propagating speed of the first and second burst signals, respectively; and
wherein the third candidate is determined by the step of determining.

6. The method according to claim 5, wherein
the step of determining a group determines a candidate-contained group where the third candidate corresponding to the true measurable quantity of the object is determined on the basis of one of the first and the second receiving signal.

7. The method according to claim 5, wherein
the step of determining a group determines a candidate-contained group on the basis of a group determination receiving signal different from the first and the second receiving signal.

8. The method according to claim 7, wherein
the step of determining a group determines the candidate-contained group on the basis of the group determination receiving signal having a signal waveform continuing duration that is shorter than those of the first and the second receiving signal.

9. The method according to claim 7, wherein the step of determining the group determines a candidate-contained group on the basis of the group determination receiving signal having a rising waveform steeper than the first and the second receiving signal.

10. The method according to claim 8, or 9, wherein
the step of determining a group determines the candidate-contained group on the basis of the group determination receiving signal corresponding to a group determination transmitting signal having an impulse-like waveform.

11. The method according to claim 5, wherein the step of determining a group determines a candidate-contained group on the basis of one of an amplitude value and a waveform rising point of one of the first or second receiving signals and any of the envelopes of the first and second receiving signals .

12. An apparatus for detecting a measurable quantity of an object, the apparatus comprising:
a first transmission means for transmitting a first burst signal of a first frequency to the object to be detected;
a second transmission means for transmitting a second burst signal of a second frequency, which is different from the first frequency, to the object;
a first receiving means for receiving a first receiving signal, which corresponds to the first burst signal, from the object;
a second receiving means for receiving a second receiving signal, which corresponds to the second burst signal, from the object;
a first candidate deriving means for deriving a first candidate of a measurable quantity of the object on the basis of the first receiving signal;
a second candidate deriving means for deriving a second candidate of the measurable quantity of the object on the basis of the second receiving signal; and
a third candidate deriving means for deriving a third candidate of the measurable quantity of the object by selecting one of the first candidate and the second candidate wherein
said first candidate deriving means derives a finite number of first candidates of physical quantity of the object by the first frequency on the basis of the phase of the first receiving signal, and
said second candidate deriving means derives a finite number of second candidates of physical quantity of the object by the second frequency on the basis of the phase of the second receiving signal.

13. The apparatus according to claim 12, wherein
said first candidate deriving means derives a finite number of first candidates of the measurable quantity of the object on the basis of first waveform information of the first receiving signal,
said second candidate deriving means derives a finite number of second candidates of the measurable quantity of the object on the basis of second waveform information of the second receiving signal, and
said third candidate deriving means derives a finite number of third candidates of the measurable quantity of the object.

14. detecting device according to claim 12 or 13, further comprising:
a selecting/determining means for selecting a specific candidate from among said third candidates derived by said third candidate deriving means and determining the specific candidate as a physical quantity of the object.

15. The apparatus according to claim 14, further comprising:
means for determining a group where the third candidate corresponding to the true measurable quantity of the object is determined, the third candidate corresponding to the true measurable quantity of the object being a member of a group of the finite number of first candidates and a group of the finite number of second candidates, which are periodically derived at periods that are determined by the first and the second frequency and a propagating speed of the first and second burst signals, respectively, and
said selecting/determining means selects a specific candidate from among the third candidates on the basis of the determining result of the means of determining the group where a candidate corresponding to the true measurable quantity of the object is present, and determines that the specific candidate is a measurable quantity of the object.

16. The apparatus according to claim 12, further comprising:
a determining means for determining a group where the third candidate that corresponds to a true measurable quantity of the object is determined, the candidate corresponding to the true measurable quantity of the object being a member of a group of first candidates and a group of second candidates, which are periodically derived at periods determined by the first and the second frequency and a propagating speed of the first and second burst signals, respectively, and
wherein the third candidate is determined by the group determining means.

17. The apparatus according to claim 16, wherein said group determining means determines a candidate-contained group on the basis of one of the first and the second receiving signal.

18. The apparatus according to claim 16, wherein said group determining means determines a candidate-contained group on the basis of a group determination receiving signal different from the first and the second receiving signal.

19. The apparatus according to claim 18, wherein said group determining means determines the candidate-contained group on the basis of a group determination receiving signal of which a signal waveform continuing duration is shorter than those of the first and the second receiving signal.

20. The apparatus according to claim 18, wherein said means for determining a group determines the candidate-contained group on the basis of a group determination receiving signal having a rising waveform steeper than the first and the second receiving signal.

21. The apparatus according to claim 19, or 20, wherein said means for determining a group determines the candidate-contained group on the basis of a group determination receiving signal corresponding to a group determination transmitting signal of impulse-like waveform.

22. The apparatus according to claim 16, wherein said group determining means determines the candidate-contained group on the basis of one of an amplitude value and a waveform rising point of one of the first or second receiving signals and any of the envelopes of the first and second receiving signals.

* * * * *